US008455640B2

(12) United States Patent
Reddy et al.

(10) Patent No.: US 8,455,640 B2
(45) Date of Patent: Jun. 4, 2013

(54) PROCESS FOR STATINS AND ITS PHARMACEUTICALLY ACCEPTABLE SALTS THEREOF

(75) Inventors: Manne Satyanarayana Reddy, Hyderabad (IN); Srinivasan Thirumalai Rajan, Hyderabad (IN); Maramreddy Sahadeva Reddy, Hyderabad (IN)

(73) Assignee: MSN Laboratories Limited, Hyderabad, Andhra Pradesh (IN)

( * ) Notice: Subject to any disclaimer, the term of this patent is extended or adjusted under 35 U.S.C. 154(b) by 1085 days.

(21) Appl. No.: 12/226,932

(22) PCT Filed: Apr. 30, 2007

(86) PCT No.: PCT/IN2007/000172
§ 371 (c)(1),
(2), (4) Date: Feb. 20, 2009

(87) PCT Pub. No.: WO2007/125547
PCT Pub. Date: Nov. 8, 2007

(65) Prior Publication Data
US 2009/0275752 A1    Nov. 5, 2009

(30) Foreign Application Priority Data

May 3, 2006   (IN) ............................ 805/CHE/2006
Mar. 26, 2007 (IN) ............................ 606/CHE/2007

(51) Int. Cl.
*C07D 239/42* (2006.01)
*C07D 235/04* (2006.01)

(52) U.S. Cl.
USPC ..................... 544/330; 544/332; 548/304.4

(58) Field of Classification Search
USPC .................................. 544/330, 332
See application file for complete search history.

(56) References Cited

U.S. PATENT DOCUMENTS

| | | | |
|---|---|---|---|
| 4,739,073 A | 4/1988 | Kathawala | |
| 4,970,313 A | 11/1990 | Wess et al. | |
| 4,977,279 A | 12/1990 | Wess et al. | |
| 5,260,440 A | 11/1993 | Hirai et al. | |
| 5,273,995 A | 12/1993 | Roth | |
| 5,354,772 A | 10/1994 | Kathawala | |
| 5,753,675 A | 5/1998 | Wattanasin | |
| 5,763,675 A | 6/1998 | Levin | |
| 5,856,336 A | 1/1999 | Fujikawa et al. | |
| 6,316,460 B1 | 11/2001 | Creekmore et al. | |
| 6,627,636 B2 | 9/2003 | Robl | |
| 6,835,838 B2 | 12/2004 | Chen et al. | |
| 6,841,554 B2 | 1/2005 | Taylor et al. | |
| 6,844,437 B1 | 1/2005 | Taylor et al. | |
| 6,875,867 B2* | 4/2005 | Brodfuehrer et al. | 540/577 |
| 7,312,329 B2* | 12/2007 | Joshi et al. | 544/243 |
| 7,371,865 B2 | 5/2008 | Acemoglu et al. | |
| 2004/0049036 A1 | 3/2004 | Taylor et al. | |
| 2004/0176401 A1 | 9/2004 | Matsushita et al. | |
| 2005/0080134 A1 | 4/2005 | Niddam-Hildesheim et al. | |
| 2005/0124639 A1 | 6/2005 | Joshi et al. | |
| 2005/0209259 A1 | 9/2005 | Huang | |
| 2006/0004200 A1 | 1/2006 | Gudipati et al. | |
| 2009/0054450 A1* | 2/2009 | Currie et al. | 514/252.19 |
| 2010/0056783 A1 | 3/2010 | Satyanarayana Reddy et al. | |
| 2011/0160225 A1* | 6/2011 | Currie et al. | 514/254.05 |

FOREIGN PATENT DOCUMENTS

| | | |
|---|---|---|
| CH | 101386592 A | 3/2009 |
| CN | 1821242 A * | 8/2006 |
| EP | 0 304 063 B1 | 11/1994 |
| EP | 1 099 694 B1 | 8/2005 |
| JP | 6041114 A | 5/1994 |
| WO | WO 95/11898 | 5/1995 |
| WO | WO 95/13283 | 5/1995 |
| WO | WO 97/19917 | 6/1997 |
| WO | WO 98/32751 | 7/1998 |
| WO | WO 99/11258 | 3/1999 |
| WO | WO 99/45003 | 9/1999 |
| WO | WO 01/60804 A1 | 8/2001 |
| WO | WO 02/09697 A1 | 2/2002 |
| WO | WO 02/092570 A1 | 11/2002 |
| WO | WO 02/094804 A1 | 11/2002 |
| WO | WO 03/006439 A1 | 1/2003 |
| WO | WO 03/016317 A1 | 2/2003 |
| WO | WO 03/045935 A1 | 6/2003 |
| WO | WO 03/070717 A1 | 8/2003 |
| WO | WO 03/097614 A2 | 11/2003 |
| WO | WO 2004/014872 A1 | 2/2004 |
| WO | WO 2004/108691 A1 | 12/2004 |
| WO | WO 2005/033083 A1 | 4/2005 |
| WO | WO 2005/040134 A1 | 5/2005 |
| WO | WO 2005/042522 A1 | 5/2005 |
| WO | WO 2005/054207 A1 | 6/2005 |

(Continued)

OTHER PUBLICATIONS

CN 1821242—-MachineTransaltion From Espacenet, Aug. 23, 2006.*
International Preliminary Report on Patentability from counterpart International Application No. PCT/IN2007/000459, dated Aug. 4, 2010.
Written Opinion of the International Searching Authority from counterpart International Application No. PCT/IN2007/000459, dated Dec. 3, 2009.
International Search Report for International Application No. PCT/IN2007/000459, dated Dec. 3, 2009.
Author unknown, "Process for the preparation of 2, 2-dimethyl-1, 2, 3, 7, 8, 8a-hexahydro-3, 7-dimethyl-8-[2-tetrahydro-4-hydroxy-6-oxo-2H-pyran-2-yl)-ethyl]-1-napthalenyl ester and intermediates thereof", IP.com Journal, vol. 6(10A), 2 (No. IPCOM000140631D) compounds of formula IV (Sep. 17, 2006).

(Continued)

Primary Examiner — Venkataraman Balasubramanian
(74) Attorney, Agent, or Firm — Hamilton, Brook, Smith & Reynolds, P.C.

(57) ABSTRACT

Novel process for statins and its pharmaceutically acceptable salts thereof represented by general formula (I).

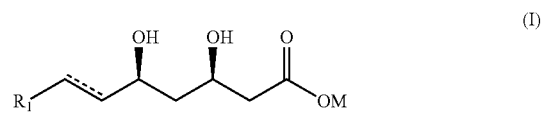

(I)

10 Claims, 2 Drawing Sheets

FOREIGN PATENT DOCUMENTS

| WO | WO 2005/077916 A1 | 8/2005 |
|---|---|---|
| WO | WO 2006/035277 A2 | 4/2006 |
| WO | WO 2006/079611 A1 | 8/2006 |
| WO | WO 2006/136407 A1 | 12/2006 |
| WO | WO 2007/000121 A1 | 1/2007 |
| WO | WO 2007000121 A1 * | 1/2007 |
| WO | WO 2007/040940 A1 | 4/2007 |
| WO | WO 2007/041666 A1 | 4/2007 |
| WO | WO 2007/052309 A2 | 5/2007 |
| WO | WO 2007/086082 A2 | 8/2007 |
| WO | WO 2007/086082 A3 | 8/2007 |
| WO | WO 2007/100351 A2 | 9/2007 |
| WO | WO 2007/125547 A2 | 11/2007 |
| WO | WO 2007/132482 A2 | 11/2007 |
| WO | WO 2007/132482 A3 | 11/2007 |
| WO | WO 2008/044243 A2 | 4/2008 |

OTHER PUBLICATIONS

Patel, D.S., et al., "Process for preparation of 2,2-dimethylbutyric acid 8-ester of [1,2,6,7,8,8a(R)-hexahydro-2(S),6(R)-dimethyl-1(S)-naphthylethyl] tetrahydro-4-hydroxy-2H-pyran-2-one from broth containing [1,2,6,7,8,8a(R)-hexahydro-2(S),6(R)dimethyl-8(S)methyl-1-oxobutoxy-1-naphthyl]-3(R),5 (R)dihydroxyheptanoic acid", (abstract) Database CA [Online] Chemcial Abstracts Service Columbus, Ohio, US; Retrieved from STN International, Columbus, Ohio, USA. Accession No. 148:403004 RN 1015249-88-3 (2007).

Brousseau, M.E., et al., "Structure and mechanism of action of HMG-CoA reductase inhibitors", The British Library—"The World's Knowledge", pp. 19-34, ed. by Gerd Schmitz and Michael Torzewski, Birkhauser (2002).

International Search Report for PCT/IN2007/000172, dated Jan. 18, 2008.

International Preliminary Report on Patentability from counterpart International Application No. PCT/IN2007/000172, dated Jun. 16, 2008.

Written Opinion of the International Preliminary Examining Authority from counterpart International Application No. PCT/IN2007/000172, dated Jan. 18, 2008.

Miyachi, N., et al., "A Novel Synthetic Method of HMG-CoA Reductase Inhibitor NK-104 Via a Hydroboration-Cross Coupling Sequence", *Tetrahedron Letters*, 34(51):8267-8270 (1993).

Wess, G., et al., "Stereoselective Synthesis of HR 780 A New Highly Potent HMG-COA Reductase inhibitor", *Tetrahedron Letters*, 31(18):2545-2548 (1990).

Takahashi, Kyoko, et al., "Synthesis of an Artificial HMG-CoA Reductase Inhibitor NK-104 via a Hydrosilylation—Cross-Coupling Reaction", *Bull. Chem. Soc. Jpn.*, 68:2649-2656 (1995).

International Search Report for International Application No. PCT/IN2010/000029, titled: "Processes for Preparing Pitavastatin, Intermediates and Pharmaceutically Acceptable Salts Thereof", dated Aug. 26, 2010.

Written Opinion of the International Searching Authority for International Application No. PCT/IN2010/000029, titled "Processes for Preparing Pitavastatin, Intermediates and Pharmaceutically Acceptable Salts Thereof", dated Aug. 26, 2010.

International Preliminary Report on Patentability for International Application No. PCT/IN2010/000029, titled "Processes for Preparing Pitavastatin, Intermediates and Pharmaceutically Acceptable Salts Thereof", dated Jul. 19, 2011.

Cai, Zheng-yan et al., "Synthesis of Pitavastatin Calcium", *Chinese Journal of Pharmaceuticals*, 38(3): 177-182 (2007).

Johnson, Douglas S., "The Art of Drug Synthesis", *Synthesis of Pitavastatin (Livalo®)*, pp. 177-179, ISBN: 15978-0-471-75215-8 (2007).

Final Office Action mailed Sep. 24, 2012 for U.S. Appl. No. 12/531,386, titled: "Novel Process for the Preparation of Statins and Their Pharmaceutically Acceptable Salts Thereof".

Non-Final Office Action mailed Apr. 24, 2012 for U.S. Appl. No. 12/531,386, titled: "Novel Process for the Preparation of Statins and Their Pharmaceutically Acceptable Salts Thereof".

* cited by examiner

PROCESS FOR STATINS AND ITS PHARMACEUTICALLY ACCEPTABLE SALTS THEREOF

RELATED APPLICATIONS

This application is the U.S. National Stage of International Application No. PCT/IN2007/000172, filed Apr. 30, 2007, published in English, and claims priority under 35 U.S.C. §119 or 365 to Indian Application No. 805/CHE/2006, filed May 3, 2006 and to Indian Application No. 606/CHE/2007 filed Mar. 26, 2007, all of which are incorporated herein by reference.

FIELD OF THE INVENTION

The present invention relates to one-pot synthesis for the preparation of statins and its pharmaceutically acceptable salts thereof represented by the general formula-1

Formula-1

Wherein R is a hydrophobic anchor or residue of an HMG CoA reductase inhibitor and may for example be Formula-A Formula-B Formula-C Wherein M is H, Na$^+$, K$^+$, Mg$^{+2}$, Ca$^{+2}$ Herein after the above compounds of formula A, B and C are referred as 'R'.

The present invention also relates to a novel process for the preparation of olefinic chiral dihydroxy acid and its pharmaceutically acceptable salts HMG CoA reductase inhibitors of general formula-2.

Formula-2

Wherein $R_1$ is a hydrophobic anchor or residue of an HMG CoA reductase inhibitor and may for example be Formula-a Formula-b Formula-c

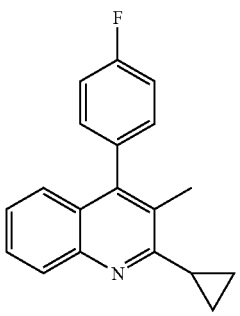

Formula-d

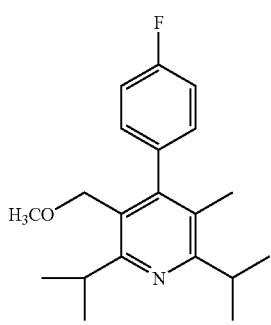

Formula-e

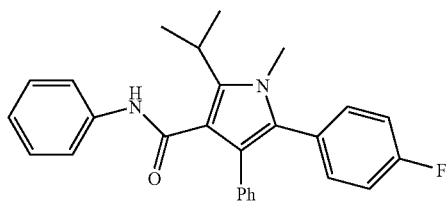

Formula-f

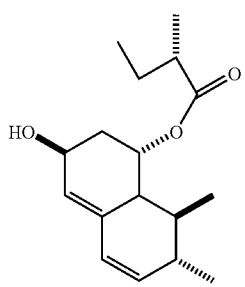

Formula-g

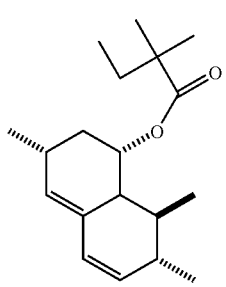

Formula-h

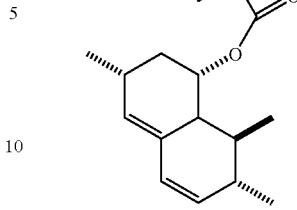

wherein '⇌' denotes single or double bond and M is H, Na⁺, K⁺, Mg⁺², Ca⁺²

Herein after the above compounds of formula (a), (b), (c), (d), (e), (f), (g) and (h) are referred as 'R₁'

The compounds of the present invention inhibit the HMG-CoA reductase, which plays a main role in the synthesis of cholesterol, and subsequently they suppress the biosynthesis of cholesterol. Therefore, they are useful in the treatment of hypercholesterolemia, hyperlipoproteinemia, and atherosclerosis.

SUMMARY OF THE INVENTION

The present invention relates to one-pot synthesis for the preparation of statins and its pharmaceutically acceptable salts thereof represented by the general formula-1.

Formula-1

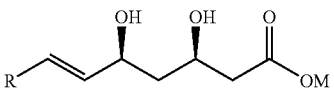

Wherein M is H, Na⁺, K⁺, Mg⁺², Ca⁺² and R is defined as above.

The present invention also relates to a novel process for the preparation of olefinic chiral dihydroxy acid and its pharmaceutically acceptable salts HMG CoA Reductase inhibitors of general formula-2

Formula-2

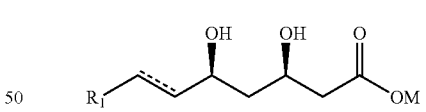

wherein '⇌' denotes single or double bond and M is H, Na⁺, K⁺, Mg⁺², Ca⁺², R₁ is defined as above.

The present invention is directed to the synthesis of chiral dihydroxy acid HMG CoA reductase inhibitors (statins) of general formula-1 and formula-2, preferably via sulfide, sulfoxide and sulfone intermediates which is used in preparing a dihydroxy acid HMG CoA reductase inhibitor or lactone thereof.

In one aspect of the present invention is to provide one-pot synthesis for the preparation of statin compounds of general formula-1.

In another aspect of the process of the invention, a Julia-Modified olefination reaction is employed wherein the sulfone intermediate is reacted with carboxylaldehyde to form the desired olefin which is to be isolated in high yield and optical purity which may be converted to the final HMG CoA reductase inhibitor of general formula-2.

BACKGROUND OF THE INVENTION

Rosuvastatin and process for its preparation is disclosed in U.S. Pat. No. 5,260,440 incorporated herein by reference. The process disclosed therein involves four distinct chemical steps and the generation of the phosphorane side chain requires expensive reagents and the process is both uneconomical and time consuming, and statin compounds preparation through wittig reaction leads to the formation of 'Z' isomer approximately around 20% as well as poor solubility of calcium salt of rosuvastatin has been observed in an aqueous methanol with this process, which is due to the formation of sodium chloride byproducts. This is a major drawback in the synthesis of calcium salt of rosuvastatin, hence is not suitable for commercial production.

Atorvastatin calcium and process for its preparation is disclosed in U.S. Pat. No. 5,273,995 incorporated herein by reference, discloses the enantiomer having the R form of the ring-opened acid of trans-5-(4-fluorophenyl)-2-(1-methylethyl)-N-4-diphenyl-1-[(2-tetrahydro-4-hydroxy-6-oxo-2H-pyran-2-yl)ethyl]-1H-pyrrole-3-carboxamide. i.e., [R—(R*, R*)]-2-(4-fluorophenyl)-β,δ-dihydroxy-5-(1-methylethyl)-3-phenyl-4-[(phenylamineo) carbonyl]-1H-pyrrole-1-heptanoic acid.

Fluvastatin sodium and process for its preparation is disclosed in U.S. Pat. No. 4,739,073 incorporated herein by reference, discloses fluvastatin as a racemate and its pharmaceutically acceptable salts especially sodium salt. This patent also discloses process for the preparation of fluvastatin, which involves treating (E)-3-[3'-(4'fluorophenyl)-1'-(1''-methylethyl)indol-2-yl)-2-propenal with methyl acetoacetate in presence of a strong base like n-butyl lithium and sodium hydride in tetrahydrofuran to get Methyl-(±)-(E)-7-[3'-(4''-fluorophenyl)-1'-(1''-methylethyl)-indol-2'-yl]-5-hydroxiy-3-oxo-hept-6-enoate which is further reacted with triethyl borane, tetrahydrofuran and sodium borohydride to get (±)-Erythro-7-(4''-Fluorophenyl)-1'-(1''-methylethyl)-indol-2'-yl]-3,5-dihydroxyhept-6-enoate, methyl ester followed by treated with anhydrous methanol to get the methyl(±)-erythro-(E)-3,5-dihydroxy-7-[3'-(4''-fluorophenyl)-1'-(1''-methylethyl)indol-2'-yl]hept-6-enoate(diol ester) which is purified by the column chromatography. The diol ester compound is hydrolysed with aqueous sodium hydroxide solution to get the fluvastatin sodium.

Pitavastatin and process for its preparation is disclosed in EP patent 304063 and EP 1099694 and in the publication by N. Miyachi et al. in Tetrahedron Letters 1993, Vol. 34, page no. 8267-8270 and by K. Takahashi et al. in Bull. Chem. Soc. Jpn. 1995, Vol. 68, 2649-2656. These publications describe the synthesis of Pitavastatin in great detail.

Our earlier Indian patent application 782/CHE/2005 published in Indian patent Journal on 18th Aug. 2006 incorporated herein by reference, discloses a novel process for the preparation of rosuvastatin calcium. The said patent also discloses following organic amine salt of rosuvastatin, cyclic amines such as cyclopropyl amine, cyclo pentyl amine, cyclo hexyl amine, dicyclohexyl amine, pyrrolidine or morpholine or alkylamines such as isopropyl amine, diisopropyl amine, phenyl propyl amine, tertiary butyl amine and its analogues. It further discloses the purification of organic amine salts in acetone, acetonitrile or mixture of acetonitrile and isopropyl alcohol.

Tetrahedron Letters, Vol. 31, No. 18, pp 2545-2548, 1990 incorporated herein by reference, discloses stereo selective synthesis of HMG-COA reductase inhibitors through lactone intermediate i.e., corresponding protected ester compound on reaction with trifluoroacetic acid. The said journal discloses the pyridine derivative compound as HMG-COA reductase inhibitor and disclosed various synthetic processes (i.e., by wittig and wittig homer reaction), The said journal also discloses a process for the preparation of aldehyde side chain of HMG-CoA reductase inhibitors.

U.S. Pat. No. 4,977,279 incorporated herein by reference, this patent discloses derivatives of 3-demethylmevalonic acid. This patent also teaches the process for the preparation of pyridine and pyrimidine derivatives of demethylmevalonic acid.

U.S. Pat. No. 4,970,313 incorporated herein by reference, discloses process for the preparation of optically active 3-demethylmevalonic acid derivatives via β-hydroxy lactone and also disclosed the protected aldehyde side chain of Statin compounds.

The alternate method for the preparation of olefinic compounds is Julia classical olefination, Julia modified olefination, Julia modified olefination process for the preparation of HMG CoA Reductase inhibitors, is disclosed and claimed in U.S. Pat. No. 6,875,867 incorporated herein by reference, in this patent chiral diol sulfone (aliphatic chain of statins) intermediates used for the preparation of HMG CoA reductase inhibitors, the disclosed chiral diol sulfones are not stable and low yields were observed when using aliphatic chiral diol sulfones when compare to aromatic sulfone derivatives.

International publication WO 2001/60804 incorporated herein by reference, discloses a process for the preparation of amorphous form of rosuvastatin calcium from amine salt which gives high pure rosuvastatin calcium. The amine salt can be recrystallized to get highest purity. The said patent also discloses a process for the preparation of amine salt from an acid.

International publication WO 2004/014872 incorporated herein by reference, discloses a process for the preparation of calcium salt of rosuvastatin. The process comprises, mixing of calcium chloride with a solution of water soluble salt of rosuvastatin like sodium salt, methylamine salt, tris salt and ammonium salt wherein the process parameters are selected to give a product which demonstrates improved efficiency of filtration.

International publication WO2004/108691 incorporated herein by reference, discloses a process for an improved production of rosuvastatin calcium salt which discloses the usage of calcium chloride, calcium bromide and calcium acetate as a calcium source for the preparation of rosuvastatin calcium.

International publication WO 2005/042522 incorporated herein by reference, the said patent claims crystalline form of dihydroxy and olefin compound of rosuvastatin ester.

International publication WO 2005/054207 incorporated herein by reference, discloses an alternate process for the preparation of rosuvastatin and its intermediates via wittig reagents. The process involved the condensation of wittig reagent like triphenyl[4-(4-fluorophenyl)-6-isopropyl-2-[methyl(methylsulfonyl)amino]pyrimidin-5-ylmethyl]phosphonium bromide or other reagent with aldehyde side chain compound tert-butyl2-[(4R,6S)-6-formyl-2,2-dimethyl-1,3-dixan-4-yl}acetate in a suitable solvent and in presence of a base to give tertiarybutyl ester compound of rosuvastatin which is further converted into free acid then to calcium salt by contacting calcium source. This process suffers from quality aspects as Z isomer formation is high (i.e., approximately 20%) in witting reactions.

International publication WO 2005/077916 incorporated herein by reference, discloses crystalline cyclohexyl ammonium, diisopropyl ammonium, isopropyl ammonium, dicyclohexyl ammonium(S)-(+)-methylbenzyl ammonium salts of rosuvastatin and process for their preparation. The said patent also discloses process for the preparation of amorphous rosuvastatin calcium from generic amine salt of rosuvastatin and the PXRD pattern of amorphous form of rosuvastatin calcium.

International publication WO 2006/035277 incorporated herein by reference, discloses a process for the preparation of amorphous form of rosuvastatin calcium and novel crystalline form A of rosuvastatin calcium and also disclosed the PXRD pattern of both crystalline and amorphous form of rosuvastatin calcium salt.

International publication WO 2006/079611 incorporated herein by reference, discloses a novel crystalline form B and C of rosuvastatin calcium salt hydrates and process for their preparation. The disclosed PXRD pattern of the Form C is similar to the disclosed amorphous form of rosuvastatin calcium.

International publication WO 2006/136407 incorporated herein by reference, disclosed a pure amorphous form of rosuvastatin calcium having HPLC purity more than 99.9% and free from any traces of alkali metal impurities. The said patent also discloses process for the preparation of amorphous rosuvastatin calcium, which comprises of reacting the tertiary butyl ester of rosuvastatin with organic amine salt to get pure amorphous rosuvastatin calcium. The international publication WO 2001/60804 is also disclosed process for the preparation of pure amorphous rosuvastatin calcium from organic amine salt compound.

International publication WO 2007/000121 incorporated herein by reference, discloses a process for the preparation of hemi-calcium salt of rosuvastatin in crystalline or amorphous solid state. The process comprises of hydrolyzing the alkyl ester or amides of rosuvastatin and converting the obtained alkali salt into calcium salt of rosuvastatin by reacting with suitable calcium source in aqueous medium followed by extracting the crude rosuvastatin calcium into a solvent partially miscible with water, washing with water and isolating by cooling and filtration or by adding anti-solvent and filtration or spray drying into the stream of inert gas.

International publication WO 2007/040940 incorporated herein by reference, discloses a process for the preparation of diasteriomerically pure rosuvastatin and intermediates.

International publication WO 2007/041666 incorporated herein by reference, discloses a process for the preparation of rosuvastatin calcium by employing witting homer reaction.

It is, therefore, desirable to provide an efficient process for the preparation of statins which improves the economics by employing less expensive reagents and is more productive compare to the known processes.

The present invention provides a novel and advantageous process for the preparation of calcium salt of statins which solves solubility problem of the compound in an aqueous methanol and gives free flow solid of calcium salt. The present invention uses calcium acetate instead of calcium chloride so the byproduct is sodium acetate, which is highly soluble in water. So the obtained compound is freely soluble in methanol.

The present invention provides a process which involves less number of steps, without isolation of intermediate, eco-friendly, easy to scale-up and commercially viable for the preparation of statins and its pharmaceutically acceptable salts thereof.

Disadvantages of the Prior Art Processes:
Usage of hazardous reagents like phosphorous trihalides or phosphorous oxyhalides.
Usage of strong base like LDA/n-BuLi followed by usage of Na/Hg in Julia classical olefination reactions, which are highly pyrophoric in nature, hence those are not recommended for commercial scale up.
Usage of strong base like LDA/n-BuLi in Julia modified olefination reactions, which are highly pyrophoric in nature, hence those are not recommended for commercial scale up.
Chiral diol sulfone compounds which are prepared as per the procedure given in U.S. Pat. No. 6,875,867 are unstable intermediates.
Poor solubility of calcium salt compound of formula-1 in an aqueous methanol.
Z isomer content is high in the rosuvastatin calcium prepared as per the prior art.

BRIEF DESCRIPTION OF THE INVENTION

In accordance with the present invention, a process is provided for preparing chiral dihydroxy acid HMG CoA reductase inhibitors which are useful as anti-cholesterol agents as described hereinafter.

The present invention provides a novel process for the preparation of statins and its pharmaceutically acceptable salts compound of general formula-1 and general formula-2

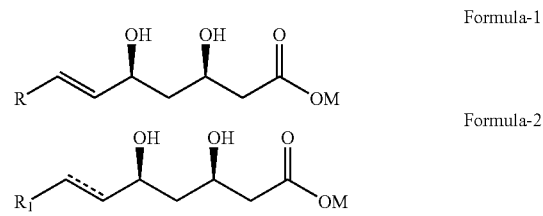

wherein '⇌' denotes single or double bond and M is H, Na$^+$, K$^+$, Mg$^{+2}$, Ca$^{+2}$ and R, R$_1$ is defined as above.

The first aspect of the present invention is to provide one-pot synthesis for the preparation of statins and its pharmaceutically acceptable salts represented by general formula-1, which comprises of the following steps
  a) Reacting the sulfone compound of general formula-3 with an aldehyde compound of formula-4 in presence of a suitable alkali base in a suitable solvent to give condensed product, which in-situ reaction with a suitable acid in a suitable aqueous solvent followed by basic hydrolysis of the obtained product in suitable aqueous solvent then treatment with suitable organic amine in a suitable solvent gives organic amine compound of general formula-5, followed by purifying in a suitable solvents gives the pure organic amine compound of general formula-5,
  b) Converting the organic amine compound of general formula-5 into its pharmaceutically acceptable salt of general formula-1 by treating the organic amine compound of general formula-5 with an alkali base, optionally isolating the corresponding alkali salt compound of general formula-6 followed by treating with alkali or alkaline earth metal salts in a suitable solvent.

The second aspect of the present invention is to provide one-pot synthesis for the preparation of statins and its pharmaceutically acceptable salts represented by general formula-1, which comprises of the following steps a) Reacting sulfone compound of general formula-3 with an amide compound of general formula-7 in presence of an alkali and alkaline earth metal bases in a suitable polar aprotic solvent to provide compound of general formula-8, which in-situ reacting with suitable acid to form diol compound of general formula-9, which upon treating with base such as an alkali metal hydroxide to form corresponding alkali metal salt then further treating with an organic amine base to give organic amine compound of general formula-5, b) Converting the organic amine compound of general formula-5 into its pharmaceutically acceptable salt of general formula-1 by treating the organic amine compound of general formula-5 with an alkali base, optionally isolating the corresponding alkali salt compound of general formula-6 followed by treating with alkali or alkaline earth metal salts in a suitable solvent.

The third aspect of the present invention is to provide one-pot synthesis for the preparation of statins and its pharmaceutically acceptable salts represented by general formula-1, which comprises of the following steps a) Reacting the sulfone compound of general formula-3 with an aldehyde compound of formula-4 in presence of an alkali and alkaline earth metal bases in a suitable solvent to provide the condensed compound, which in-situ reacting with suitable acid to give the lactone compound which is further reacting with suitable organic amine to give an amide compound of general formula-10, b) Reacting the amide compound of general formula-10 with suitable base followed by reacting with suitable organic amine to give an organic amine compound of general formula-5, c) Converting the organic amine compound of general formula-5 into its pharmaceutically acceptable salt of general formula-1 by treating the organic amine compound of general formula-5 with an alkali base, optionally isolating the corresponding alkali salt compound of general formula-6 followed by treating with alkali or alkaline earth metal salts in a suitable solvent.

The fourth aspect of the present invention is to provide one-pot synthesis for the preparation of statins and its pharmaceutically acceptable salts represented by general formula-1, which comprises of the following steps a) Reacting sulfone compound of general formula-3 with an aldehyde compound of formula-4 in presence of an alkali and alkaline earth metal bases in a suitable polar aprotic solvent to provide a compound of general formula-11, which in-situ reacting with suitable acid to form diol compound of general formula-12, which upon treating with a base such as an alkali metal hydroxide to form corresponding alkali metal salt then further treating with an organic amine base to give organic amine compound of general formula-5, b) Converting the organic amine compound of general formula-5 into its pharmaceutically acceptable salt of general formula-1 by treating the organic amine compound of general formula-5 with an alkali base, optionally isolating the alkali salt of corresponding compound of general Formula-6 followed by treating with corresponding alkali or alkaline earth metal salts in a suitable solvent.

The fifth aspect of the present invention is to provide a novel process for the preparation of olefin dihydroxy compound of general formula-2 via a Julia-Modified olefination, which comprises of the following steps a) Reacting the sulfone compound of general formula-13 with an aldehyde compound of general formula-14 in presence of an alkali and alkaline earth metal bases in a suitable polar aprotic solvent to provide olefin compound of general formula-15, b) The olefin compound of general formula-15 may be used to form a dihydroxy acid (or lactam thereof) HMG CoA reductase inhibitor by subjecting the olefin compound of formula-15 to acidic conditions to remove the acetonide and form diol compound, which upon treating with a base such as an alkali metal hydroxide to form the corresponding alkali metal salt then further treating with an organic amine base to form corresponding organic amine compound of general formula-16, c) Converting the organic amine compound of general formula-16 into free acid compound of formula-21 by treating the organic amine compound of general formula-6 with an acid to give an acid compound of formula-21, d) The alkenyl double bond in acid compound of formula-21 may be hydrogenated ($H_2$/Pd/C) to provide the saturated alkyl acid compound of formula-22, e) Converting the dihydroxy acid compound or its organic amine salt into its pharmaceutically acceptable salts of the general formula-2 by treating the organic amine compound of general formula-16 or acid compound of general formula-21 with an alkali base followed by treating with corresponding alkali or alkaline earth metal salts in a suitable solvent.

The lactone compound of formula-23 may be prepared

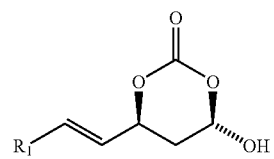

Formula-23 by treating the olefin compound of formula-15 under acid conditions (for example, TFA, HCl) to effect conversion to lactone compound of formula-23. The saturated derivative of lactone compound of formula-23 may be obtained by catalytic (Pd/C, Pt/C, Pd(OH)$_2$) hydrogenation of compound of formula-23 to compound of formula-24.

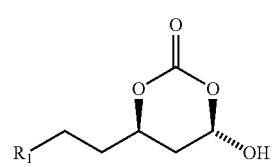

Formula-24

Lactone compounds of formula-23 and formula-24 may be converted to the corresponding diol compounds by saponification of formula-23 and formula-24 with aqueous base to form corresponding alkali salt compounds of formula-25 and formula-26

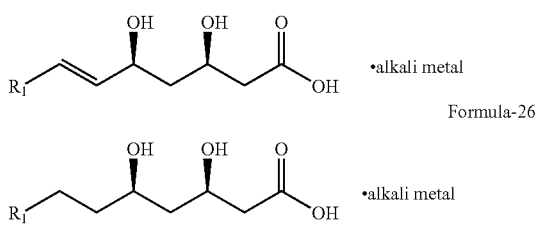

Formula-25

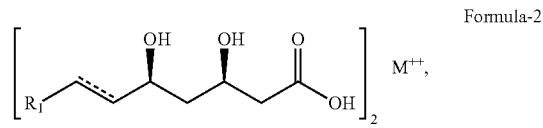

Formula-26

The sixth aspect of the present invention is to provide a novel process for the preparation of olefin dihydroxy compound of general formula-2 is provided via a Julia-Modified olefination, which comprises of the following steps a) Reacting a sulfoxide compound of general formula-17 with an aldehyde compound of general formula-14 in presence of an alkali and alkaline earth metal bases in a suitable polar aprotic solvent to provide olefin compound of general formula-15, b) The olefin compound of general formula-15 may be used to form a dihydroxy acid (or lactam thereof) HMG CoA reductase inhibitor by subjecting olefin compound of general formula-15 to acidic conditions to remove the acetonide and form diol compound, which upon treating with a base such as an alkali metal hydroxide to form corresponding alkali metal salt then further treating with an organic amine base to form corresponding organic amine compound of general formula-16, c) Converting the organic amine compound of general formula-16 into free acid compound of formula-21 by treating the organic amine compound of general formula-16 with an acid to give an acid compound of formula-21, d) The alkenyl double bond in acid compound of formula-21 may be hydrogenated ($H_2$/Pd/C) to provide the saturated alkyl acid compound of formula-22, e) Converting the dihydroxy acid compound or its organic amine salt into its pharmaceutically acceptable salts of general formula-2 by treating the organic amine compound of general formula-16 or an acid compound of general formula-21 with an alkali base followed by treating with corresponding alkali or alkaline earth metal salts in a suitable solvent.

The seventh aspect of the present invention is to provide a novel process for preparing a novel sulfone and sulfoxide compounds having general Formula-13 and general formula-17, which comprises of the following steps a) Reacting a compound of general formula-18 with a thiol compound of general formula-19 in presence of a suitable base with or without a suitable solvent to provide a novel sulfide compound of general formula-20, b) And oxidizing the sulfide compound of formula-20 with an oxidizing agent in presence of an appropriate catalyst in a suitable solvent, to provide a novel sulfone compound of general Formula-13 and sulfoxide compound of formula-17 can be prepared by controlled oxidation of sulfide.

The eighth aspect of the present invention is to provide a novel process for the preparation of calcium salt of statins compounds of general formaula-1 and compound of general formula-2, which comprises of the following steps.

a) Converting the organic amine salt compound of general formula-5 or general formula-16 into its corresponding alkali salt by treating with alkali base;

b) Setting the reaction mixture pH to 8.0 to 9.2 by evaporating the solvent containing organic amine under nitrogen atmosphere followed by extraction or by extracting the organic amine with a suitable solvent or by adding an acid, c) Adding the aqueous phase of the reaction mixture to a calcium source to give free flow calcium salt compound of general formula-1 or general formula-2.

Formula-2

Wherein M is Calcium and $R_1$ is defined as above

In addition, in accordance with the present invention, the following intermediates prepared by the process of the invention are novel compounds;

1. Sulfide compounds of general formula-20

Formula-20

Wherein $R_1$ is as defined above and is linked to sulphur atom with a methylene group and $R_2$ is as defined above.

2. Sulfone compounds of general Formula-13

Formula-13

Wherein $R_1$ is as defined above which is linked to sulphur atom with a methylene group (—$CH_2$—) and $R_2$ is as defined above.

3. Sulfoxide compounds of general formula-13

Formula-17

Wherein $R_1$ is as defined above which is linked to sulphur atom with a methylene group (—$CH_2$—) and $R_2$ is as defined above.

ADVANTAGES OF THE PRESENT INVENTION

No pyrophoric reagents used in present invention.
Usage of simple bases like potassium carbonate, sodium carbonate instead of using LDA/n-BuLi/LiHMDS/NaHMDS.
Sulfone compounds which are prepared as per the present invention are stable,
Yields are above 80% for all stages of the present invention.
Calcium salt compound of formula (1a) is freely soluble in an aqueous methanol,
Calcium slat compounds of statins prepared by the present invention are free flow solids.
Provides One-pot process for the preparation of statins
Provides a novel process using a novel amide intermediates
Z isomer impurity level is nil in rosuvastatin calcium obtained by the present invention
The present invention is simple and cost effective.

DETAILED DESCRIPTION OF THE INVENTION

Figure 1:
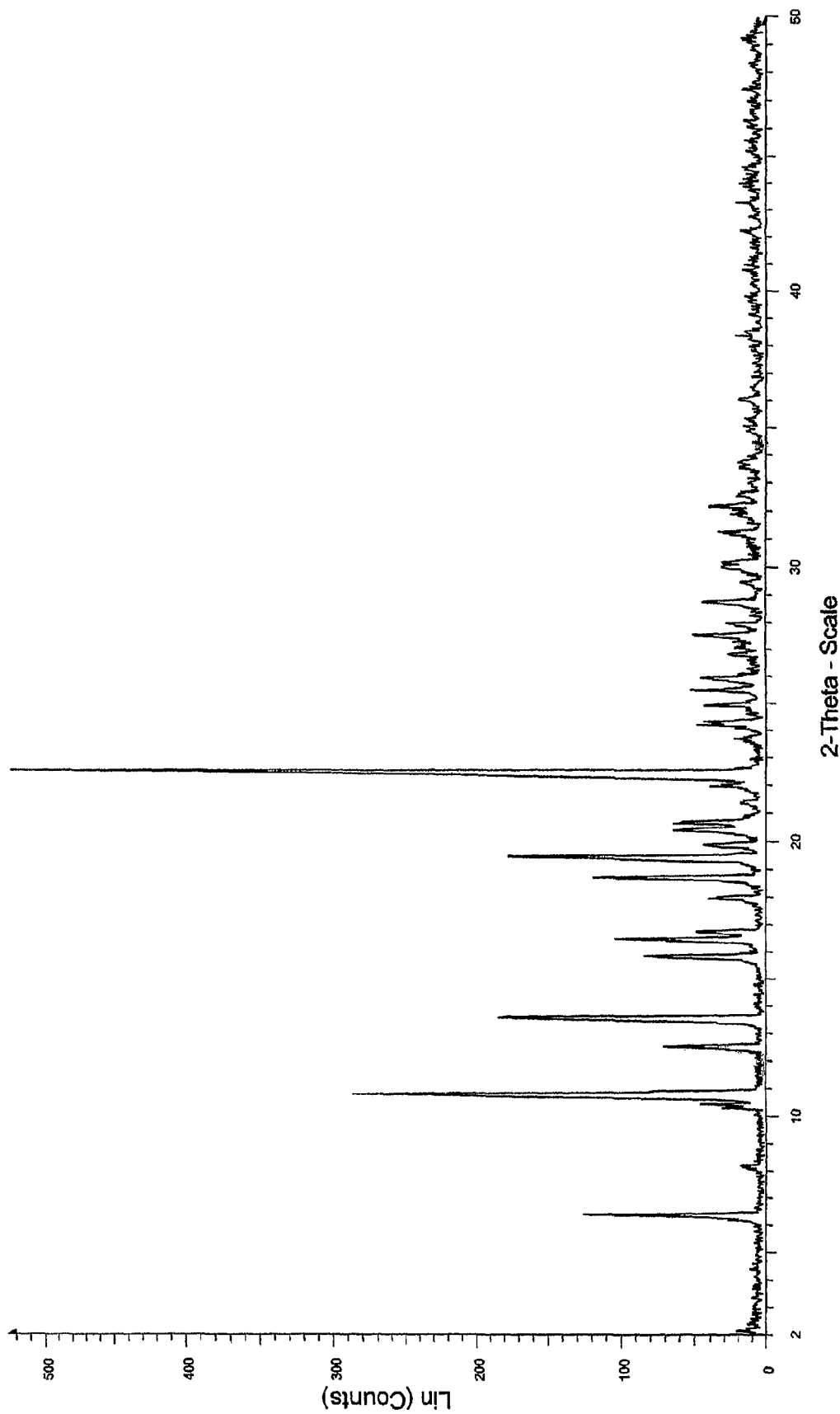
FIG. 1: Illustrates the powder X-ray diffraction pattern of rosuvastatin tertiarybutyl amine
Figure 2:
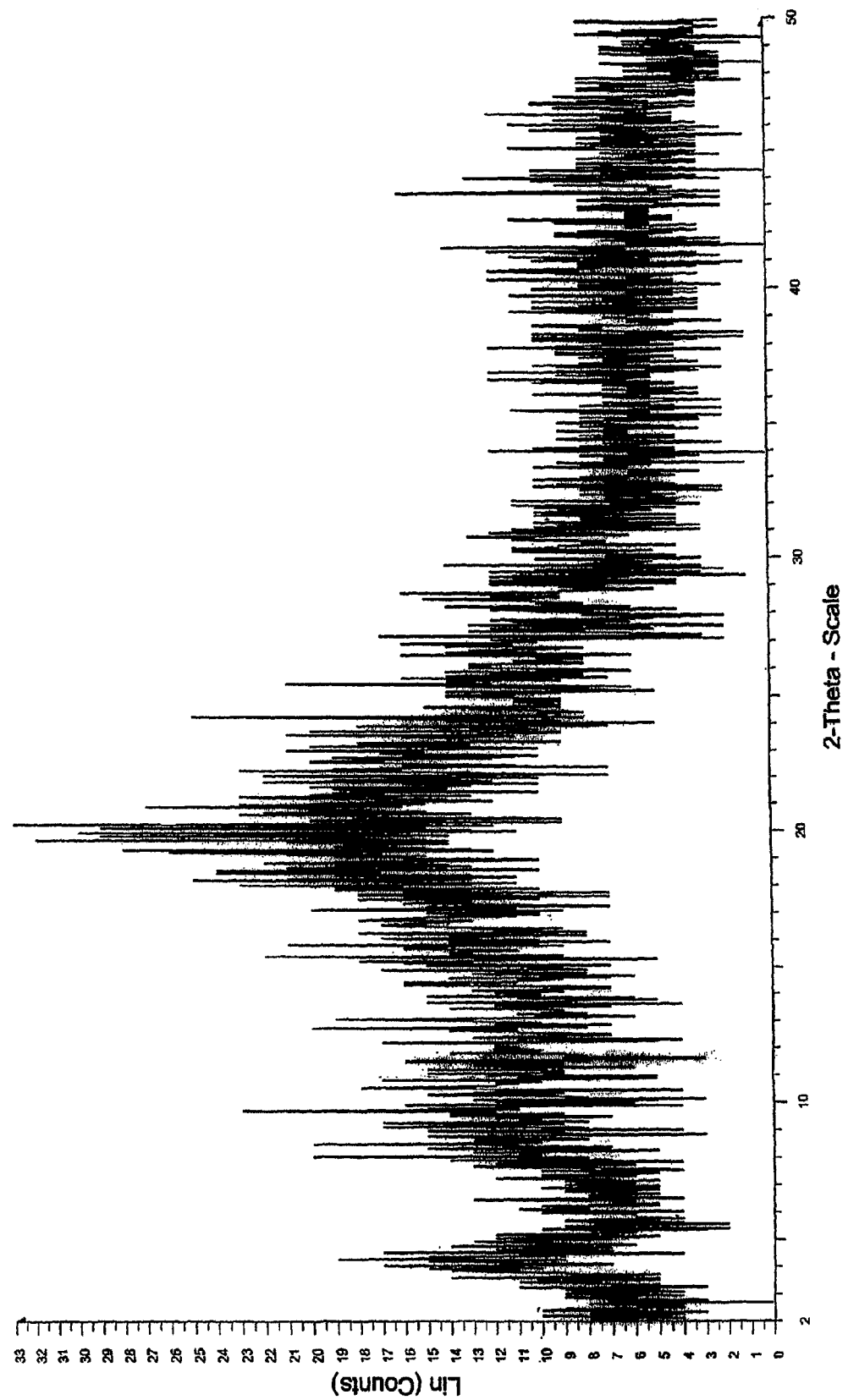
FIG. 2: Illustrates the powder X-ray diffraction pattern of amorphous rosuvastatin calcium.

In accordance with the present invention, novel process is provided for the preparation of chiral dihydroxy acid HMG CoA reductase inhibitors which are useful as anti-cholesterol agents as described hereinafter.

The present invention provides a novel process for the preparation of statins and its pharmaceutically acceptable salts compounds of general formula-1 and general formula-2,

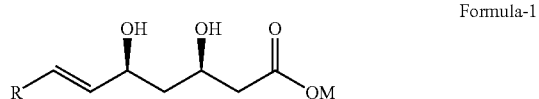

Formula-1

Wherein R is a hydrophobic anchor or residue of an HMG CoA reductase inhibitor and may for example be

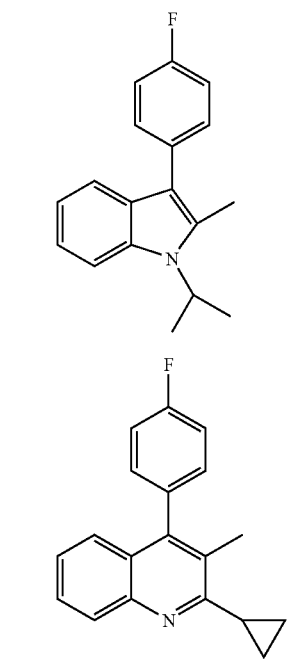

Formula-A

Formula-B

Formula-C

Wherein M is H, Na$^+$, K$^+$, Mg$^{+2}$, Ca$^{+2}$

Herein after the above compounds of formula A, B and C are referred as 'R',

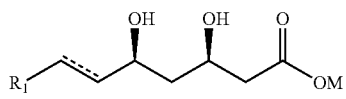

Formula-2

Wherein $R_1$ is a hydrophobic anchor or residue of an HMG CoA reductase inhibitor and may for example be

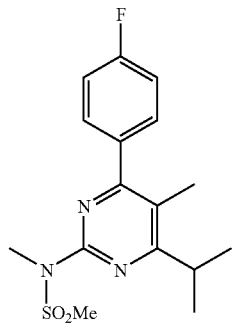

Formula-a

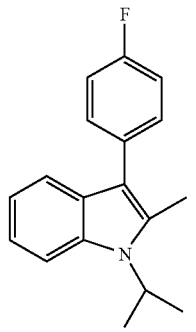

Formula-b

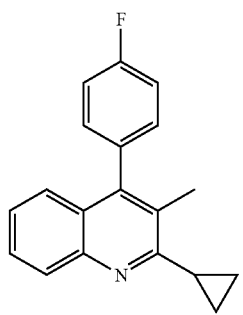

Formula-c

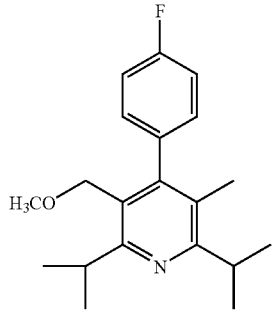

Formula-d

-continued

Formula-e

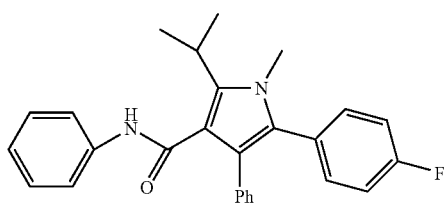

Formula-f

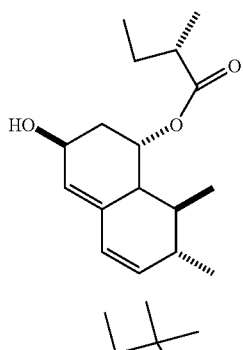

Formula-g

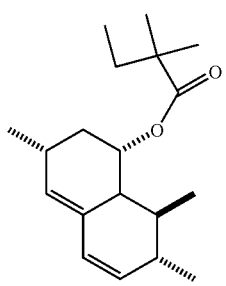

Formula-h

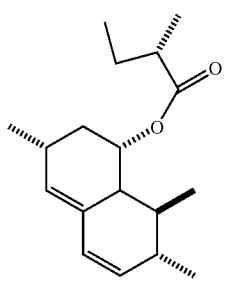

wherein "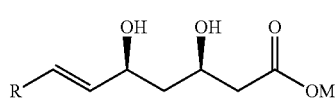" denotes single or double bond and M is H, $Na^+$, $K^+$, $Mg^{+2}$, $Ca^{+2}$ Herein after the above compounds of formula (a),(b),(c),(d),(e),(i),(g) and (h) are referred as '$R_1$'.

The first aspect of the present invention is to provide one-pot synthesis for the preparation of statins and its pharmaceutically acceptable salts thereof represented by the general formula-1, Formula-1

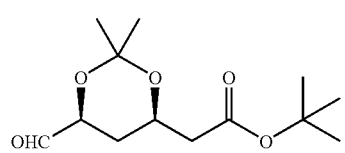

wherein M is H, $Na^+$, $K^+$, $Mg^{+2}$, $Ca^{+2}$ and R is defined as above

Which comprises of the following steps
a) Reacting the sulfone compound of general formula-3

Formula-3

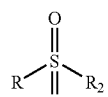

Wherein R is defined as above which is linked to sulphur atom with a methylene group (—$CH_2$—) and $R_2$ is i

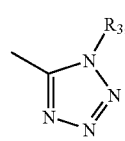

j

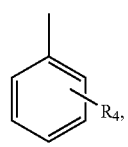

k

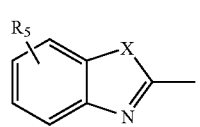

Wherein
$R_3$ is alkyl, aryl, arylalkyl or cycloalkyl,
$R_4$ is H, alkyl, aryl, arylalkyl, $CF_3$, halo or $NO_2$
$R_5$ is H, alkyl, alkaoxy, haloalkyl, monohaloalkyloxy, dihaloalkyloxy
And
X is O, N—H, N-alkyl or S;
with an aldehyde compound of formula-4

Formula-4

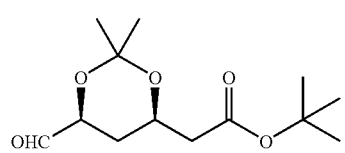

in presence of an alkali and alkaline earth metal bases such as sodium hydroxide, potassium hydroxide, potassium carbonate, sodium carbonate, lithium carbonate, and cesium carbonate preferably potassium carbonate in a suitable polar aprotic solvent like dimethylformamide, dimethylsulfoxide, dimethyl acetamide and/or toluene and/or mixtures thereof, preferably dimethyl sulfoxide gives condensed product, which in-situ reacting with trifluoroacetic acid in a suitable solvent like aqueous acetonitrile followed by basic hydrolysis of the obtained product in aqueous acetonitrile which is further reacting with suitable organic amine base in a suitable solvent to give the organic amine compound of general Formula-5 followed by the purification in a suitable alcohol solvents like methanol, ethanol and isopropyl alcohol and/or acetonitrile and/or mixtures thereof to give pure organic amine compound of general formula-5, Formula-5

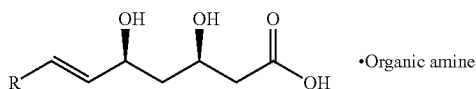

Organic amine selected from methyl amine, ethyl amine, tertiarybutyl amine, diisopropyl amine, dicyclohexyl amine, isobutyl amine, n-butylamine, (+/−) 2-butyl amine, phenyl ethyl amine, morpholine and pyrrolidine, b) Converting the corresponding organic amine compound of general formula-5 into its pharmaceutically acceptable salts of general formula-1 by treating the organic amine salt compound of general formula-5 with an alkali base such as sodium hydroxide, potassium hydroxide and lithium hydroxide and setting the pH of the reaction mixture to 9.1 by extracting the organic amine salt compound of general formula-5 with tertiary butyl acetate or by direct distillation of the reaction mixture, c) Optionally isolating the alkali, salt of corresponding compound of general formula-6, Formula-6

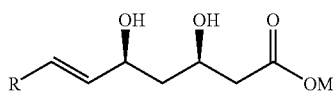

wherein M is Na$^+$, K$^+$, d) Adding the aqueous phase of the reaction mixture or an aqueous solution of isolated alkali salt compound of general formula-6 to a solution of calcium chloride or calcium acetate in a suitable solvent such as water.

The second aspect of the present invention is to provide a one-pot synthesis for the preparation of statins and its pharmaceutically acceptable salts thereof represented by general formula-1

Formula-1

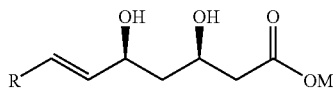

wherein M is H, Na$^+$, K$^+$, Mg$^{+2}$, Ca$^{+2}$ and R is defined as above

Which comprises of the following steps a) Reacting the sulfone compound of general formula-3

Formula-3

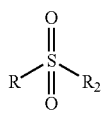

Wherein R is defined as above which is linked to sulphur atom with a methylene group (—CH$_2$—) and R$_2$ is defined as above with an amide compound of general formula-7

Formula-7

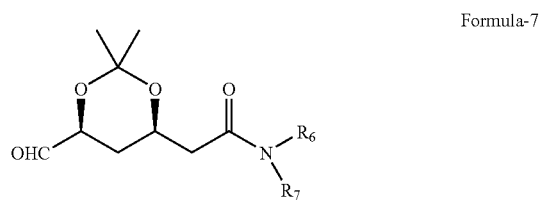

Wherein R$_6$ and R$_7$ are C$_1$-C$_{10}$ straight or branched chain alkyl or cycloalkyl or cycloalkyl with one heteroatom, in presence of an alkali and alkaline earth metal bases such as sodium hydroxide, potassium hydroxide, potassium carbonate, sodium carbonate, lithium carbonate, and cesium carbonate preferably potassium carbonate in a suitable polar aprotic solvent like dimethylformamide, dimethylsulfoxide, dimethylacetamide or mixtures thereof, preferably dimethyl sulfoxide to provide the compound of general formula-8, Formula-8

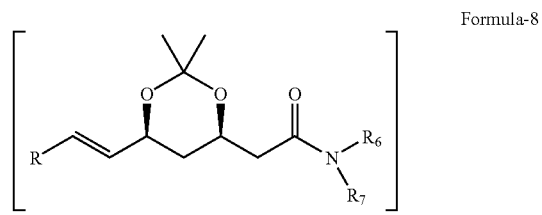

which in-situ reacting with suitable acid such as hydrochloric acid, acetic acid, sulfuric acid in a suitable solvent to give the diol compound of general formula-9, Formula-9

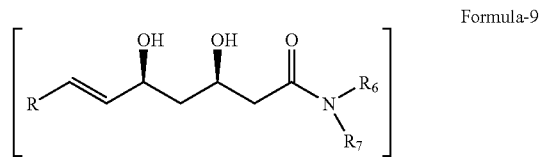

which upon treating with an alkali base such as sodium hydroxide, potassium hydroxide and lithium hydroxide to form the corresponding alkali salt then further treating with suitable organic amine base to give organic amine compound of general formula-5, Formula-5

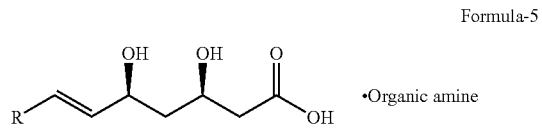

Organic amine selected from methyl amine, ethyl amine, tertiarybutyl amine, diisopropyl amine, dicyclohexyl amine, isobutyl amine, n-butylamine, (+/−) 2-butyl amine, phenyl ethyl amine, morpholine and pyrrolidine, b) Converting the corresponding organic amine compound of general formula-5 into its pharmaceutically acceptable salts of general formula-1 by treating the organic amine compound of general Formula-5 with an alkali base such as sodium hydroxide, potassium hydroxide and lithium, hydroxide and setting the pH of the reaction mixture to 9.1 by extracting the organic amine salt compound of general Formula-5 with tertiary butyl acetate or by direct distillation of the reaction mixture, c) Optionally isolating the corresponding alkali salt compound of general formula-6,

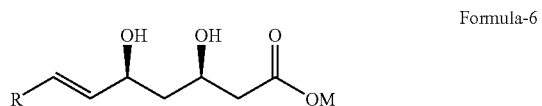

Formula-6 wherein M is $Na^+$, $K^+$ e) Adding the aqueous phase of the reaction mixture or an aqueous solution of isolated alkali salt compound of general formula-6 to a solution of calcium chloride or calcium acetate in a suitable solvent such as water.

The third aspect of the present invention is to provide one-pot synthesis for the preparation of statins and its pharmaceutically acceptable salts thereof represented by general formula-1

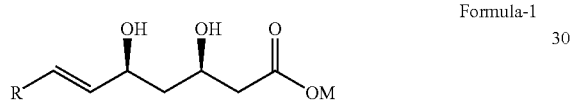

Formula-1 wherein R is defined as above and M is H, $Na^+,K^+,Mg^+,Ca^{+2}$
Which comprises of the following steps a) Reacting the sulfone compound of general formula-3

Formula-3

Wherein R is defined as above which is linked to sulphur atom with a methylene group (—$CH_2$—) and $R_2$ is defined as above With an aldehyde compound of formula-4

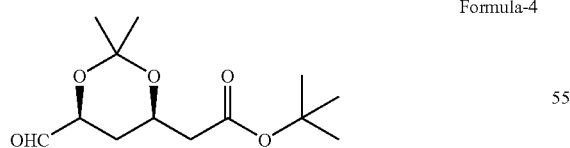

Formula-4 in presence of an alkali and alkaline earth metal bases such as sodium hydroxide, potassium hydroxide, potassium carbonate, sodium carbonate, lithium carbonate, and cesium carbonate preferably potassium carbonate in a suitable polar aprotic solvent like dimethylformamide, dimethylsulfoxide, dimethyl acetamide or mixtures thereof, preferably dimethyl sulfoxide to provide condensed compound, which in-situ reacting with trifluoroacetic acid to give the lactone compound, which is further reacting with suitable organic amine to give an amide compound of general formula-10

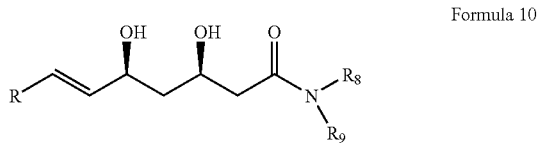

Formula 10

Wherein $R_8$ and $R_9$ are $C_1$-$C_{10}$ straight or branched chain alkyl or cycloalkyl or cycloalkyl with one heteroatom, b) Reacting the amide compound of general formula-10 with an alkali base such as sodium hydroxide, potassium hydroxide and lithium hydroxide followed by treating with suitable organic amine base to give organic amine compound of general formula-5,

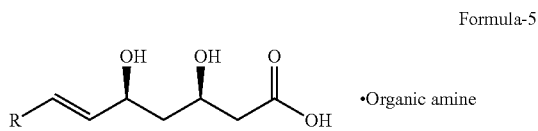

Formula-5

Organic amine selected from methyl amine, ethyl amine, tertiarybutyl amine, diisopropyl amine, dicyclohexyl amine, isobutyl amine, n-butylamine, (+/−) 2-butyl amine, morpholine and pyrrolidine, c) Converting the corresponding organic amine compound of general formula-5 into its pharmaceutically acceptable salts of general formula-1 by treating the organic amine salt compound of general formula-5 with an alkali base such as sodium hydroxide, potassium hydroxide and lithium hydroxide and setting the pH of the reaction mixture to 9.1 by extracting the organic amine salt compound of general Formula-5 with tertiary butyl acetate or by direct distillation of the reaction mixture, d) Optionally isolating the corresponding alkali salt compound of general formula-6,

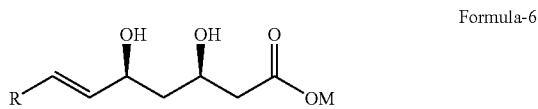

Formula-6 wherein M is $Nat$, $K^+$ f) Adding the aqueous phase of the reaction mixture or an aqueous solution of isolated alkali salt compound of general Formula-6 to a solution of calcium chloride or calcium acetate in a suitable solvent such as water.

The fourth aspect of the present invention is to provide one-pot synthesis for the preparation of statins and its pharmaceutically acceptable salts thereof represented by general formula-1,

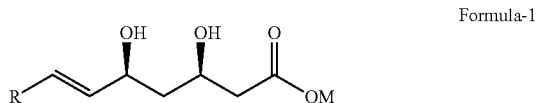

Formula-1 wherein M is H, $Na^+,K^+,Mg^{+2},Ca^{+2}$ and R is defined as above

Which comprises of the following steps
a) Reacting the sulfone compound of general formula-3

Formula-3

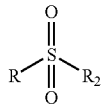

Wherein R is defined above which is linked to sulphur atom with a methylene group (—CH$_2$—) and R$_2$ is defined as above
with an aldehyde compound of Formula-4

Formula-4

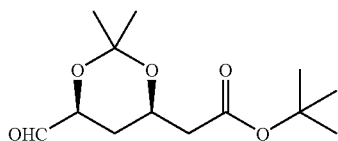

in presence of an alkali and alkaline earth metal bases such as sodium hydroxide, potassium hydroxide, potassium carbonate, sodium carbonate, lithium carbonate, and cesium carbonate preferably potassium carbonate in a suitable polar aprotic solvent like dimethylformamide, dimethylsulfoxide, dimethylacetamide or mixtures thereof, preferably dimethyl sulfoxide to provide the compound of general formula-11, Formula-11

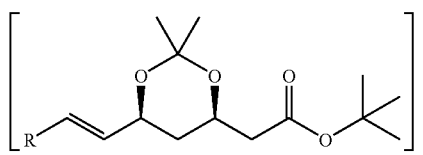

which in-situ reacting with suitable acid such as hydrochloric acid, acetic acid, sulfuric acid in a suitable solvent to give the diol compound of general formula-12, Formula-12

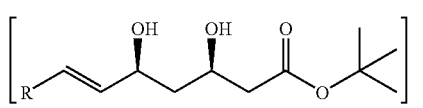

which upon treating with an alkali base such as sodium hydroxide, potassium hydroxide and lithium hydroxide to form the corresponding alkali base salt then further treating with an suitable organic amine base to give organic amine compound of general formula-5, Formula-5

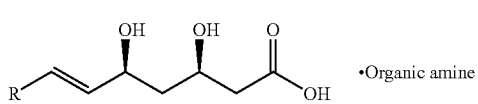

Organic amine selected from methyl amine, ethyl amine, tertiarybutyl amine, diisopropyl amine, dicyclohexyl amine, isobutyl amine, n-butylamine, (+/−) 2-butyl amine, phenyl ethyl amine, morpholine and pyrrolidine.

b) Converting the corresponding organic amine compound of general formula-5 into its pharmaceutically acceptable salts of general formula-1 by treating the organic amine compound of general formula-5 with an alkali base such as sodium hydroxide, potassium hydroxide and lithium hydroxide and setting the pH of the reaction mixture to 9.1 by extracting the organic amine salt compound of general formula-5 with tertiary butyl acetate or by direct distillation of the reaction mixture, c) Optionally isolating the corresponding alkali salt compound of general formula-6, Formula-6

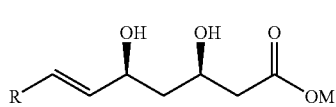

wherein M is Na$^+$, K$^+$ d) Adding the aqueous phase of the reaction mixture or an aqueous solution of isolated alkali salt compound of general formula-6 to a solution of calcium chloride or calcium acetate in a suitable solvent such as water.

The fifth aspect of the present invention is to provide a novel process for the preparation of olefinic dihydroxy compound of general formula-2 via a Julia-Modified olefination, which comprises of the following steps a) Reacting a sulfone compound of general formula-13

Formula-13

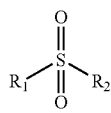

Wherein R$_1$ is defined as above which is linked to sulphur atom with a methylene group (—CH$_2$—) and R$_2$ is i

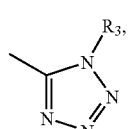

j

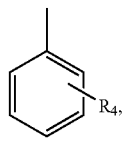

k

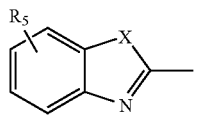

Wherein

R₃ is alkyl, aryl, arylalkyl or cycloalkyl,

R₄ is H, alkyl, aryl, arylalkyl, CF₃, halo or NO₂

R₅ is H, alkyl, alkaoxy, haloalkyl, monohaloalkyloxy, dihaloalkyloxy

And

X is O,N—H,N-alkyl or S;

Herein after the above compounds of general formula (i), (j) and (k) are referred as 'R₂' with an aldehyde compound of general formula-14

Formula-14

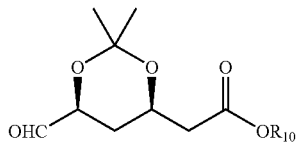

wherein R₁₀ is alkyl,cycloalkyl,arylalkyl,aryl or carbonylbenzyloxy (cbz), preferably alkyl, more preferably tertiary butyl, in presence of an alkali and alkaline earth metal bases such as sodium hydroxide, potassium hydroxide, potassium carbonate, sodium carbonate, lithium carbonate, and cesium carbonate preferably cesium carbonate in a suitable polar aprotic solvent like dimethylformamide, dimethylsulfoxide, dimethylacetamide or mixtures thereof, preferably dimethyl sulfoxide to provide olefin compound of general formula-15, Formula-15

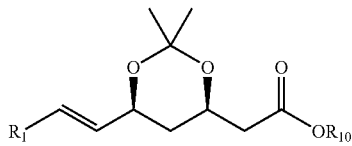

b) The olefin compound of general formula-15 may be used to form a dihydroxy acid HMG CoA reductase inhibitor by subjecting olefin compound of formula-15 to acidic conditions such as using hydrochloric acid, acetic acid, sulfuric acid to remove the acetonide and form diol compound, which upon treating with an alkali base such as sodium hydroxide to form the corresponding sodium salt then further treating with suitable organic amine base to give organic amine compound of formula-16, Formula-16

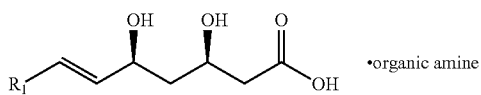

Organic amine selected from methyl amine, ethyl amine, tertiarybutyl amine, diisopropyl amine, dicyclohexyl amine, isobutyl amine, n-butylamine, (+/−) 2-butyl amine, phenyl ethyl amine, morpholine and pyrrolidine, c) Converting the corresponding organic amine compound of general formula-16 into its pharmaceutically acceptable salts of general formula-2 by treating the organic amine compound of general formula-16 with an alkali base such as sodium hydroxide followed by treating with corresponding alkali or alkaline earth metal salts like calcium chloride, calcium acetate, sodium hydroxide, potassium hydroxide in a suitable solvent such as water.

Formula-2

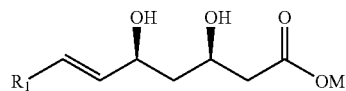

wherein M is H, Na⁺, K⁺, Mg⁺², Ca⁺² and R₁ is defined as above.

The sixth aspect of the present invention is to provide a novel process for the preparation of olefin dihydroxy compound of formula-2 via a Julia-Modified olefination, which comprises of the following steps, a) Reacting sulfoxide compound of general formula-17

Formula-17

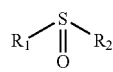

with an aldehyde compound of general Formula-14

Formula-14

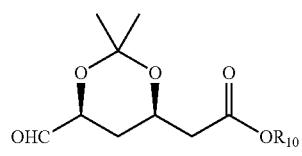

wherein R₁₀ is alkyl,cycloalkyl,arylalkyl,aryl or carbonylbenzyloxy (cbz), preferably alkyl, more preferably tertiary butyl, in presence of strong base like amide bases such as sodium bis(trimethyl silyl) amide, potassium bis(trimethyl silyl) amide, lithium bis(trimethyl silyl) amide in a suitable polar aprotic solvents like dimethylformamide, dimethylsulfoxide, dimethylacetamide or mixtures thereof, preferably dimethyl sulfoxide to provide olefin compound of general formula-15, Formula-15

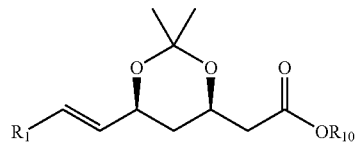

b) The olefin compound of general formula-15 may be used to form a dihydroxy acid HMG CoA reductase inhibitor by subjecting olefin compound of general formula-15 to acidic conditions such as using hydrochloric acid, sulfuric acid, acetic acid to remove the acetonide and form diol compound, which upon treating with an alkali base such as sodium hydroxide to form the corresponding sodium salt then further treating with suitable organic amine base compound to give the organic amine compound of general formula-16,

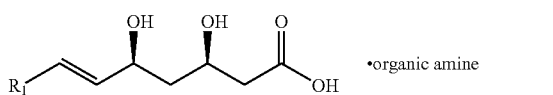

Formula-16

·organic amine

Organic amine selected from methyl amine, ethyl amine, tertiarybutyl amine, diisopropyl amine, dicyclohexyl amine, isobutyl amine, n-butylamine, (+/−) 2-butyl amine, phenyl ethyl amine, morpholine and pyrrolidine, c) Converting the corresponding organic amine compound of general formula-16 into its pharmaceutically acceptable salts of general formula-2 by treating the organic amine compound of general formula-16 with an alkali base such as sodium hydroxide followed by treating with corresponding alkali or alkaline earth metal salts like calcium chloride, calcium acetate, sodium hydroxide in a suitable solvent such as water.

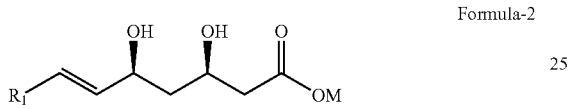

Formula-2 where M is H, $Na^+$, $K^+$, $Mg^{+2}$, $Ca^{+2}$ and $R_1$ is defined as above.

The seventh aspect of the present invention is to provide a process for the preparation of a novel sulfone compound of general formula-13 and sulfoxide derivative compound of general formula-17,

Formula-13

Formula-17

Wherein $R_1$ is defined as above which is linked to sulphur atom with a methylene group (—$CH_2$—) and $R_2$ is defined as above, which comprises of the following steps a) Treating a solution of the compound of general formula-18

$R_1$-L    Formula-18

Wherein L is a leaving group such as halogen, trifluoromethanesulfonyloxy, methanesulfonyloxy, preferably halogen, more preferably bromo and $R_1$ is defined as above which is linked to leaving group with a methylene group (—$CH_2$—)

with a thiol compound of general formula-19

$R_2$SH    Formula-19 wherein $R_2$ is defined as above in presence of a suitable base like sodium hydroxide with or without a suitable solvent, a suitable solvent selected from chloro solvents like methylene chloride, chloroform, carbon tetrachloride, keto solvents like acetone, 2-butanone, methyl isobutyl ketone, methyl ethyl ketone, ester solvents like ethyl acetate, methyl acetate, tertiary butyl acetate, polar solvents like dimethyl formamide, dimethyl acetamide, dimethyl sulfoxide, water or mixtures thereof, preferably keto solvents, more preferably acetone to provide a novel sulfide compound of formula-20

Formula-20 wherein $R_1$ is defined as above which is linked to sulphur atom with a methylene group (—$CH_2$—) and $R_2$ are defined as above b) And oxidizing a sulfide compound of formula-20 with an oxidizing agent like metachloro per benzoic acid, sodium hypochlorite, hydrogen peroxide, tertiary butyl hydrogen peroxide, cumene hydro peroxide, preferably hydrogen peroxide in the presence of an appropriate catalyst like ammonium molybdate in a single or biphasic system in a suitable solvent selected from alcoholic solvents like methanol, 2-proponol, ethanol, chloro solvents like methylene chloride, chloroform, carbon tetra chloride or mixture thereof, preferably chloro solvents, more preferably methylene chloride to provide the novel sulfone compound of general formula-13 and a novel sulfoxide compound of formula-17 can be prepared by controlled oxidation of sulfide.

The Eighth aspect of the present invention is to provide a novel, process for the preparation of calcium salt compound of general formula-1 and general formula-2,

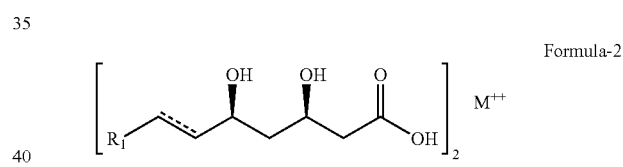

Formula-2

Wherein M is Calcium and $R_1$ is defined as above.

Which comprises of the following steps a) Converting the organic amine salt compound of general formula-5 or Formula-16 into its sodium salt by treating with sodium hydroxide, b) Setting the reaction mixture pH to 8.0 to 9.2 by evaporating the solvent containing organic amine under nitrogen atmosphere followed by extracting the reaction mixture with a suitable solvent such as ester solvents like ethyl acetate, methyl acetate, tertiary butyl acetate or by extracting the organic amine with a suitable solvent like ester solvents ethyl acetate, methyl acetate, tertiary butyl acetate, preferably tertiary butyl acetate to remove organic amine or by adding an acid like hydrochloric acid, c) Adding the aqueous phase of the reaction mixture to a calcium source like calcium chloride or calcium acetate in a suitable solvent like water to give free flow calcium salt compound of general formula-1 or formula-2 respectively.

According to the present invention, a preferred one-pot synthesis is provided for the preparation of rosuvastatin calcium salt compound of formula-1A, which comprises of the following steps a) Reacting the sulfone compound of formula-3A

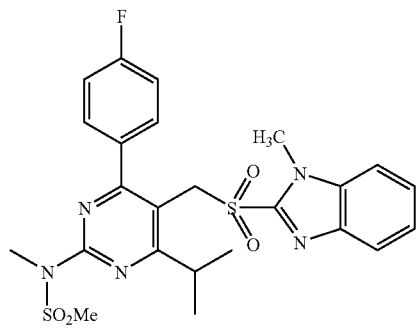

Formula-3A

With an aldehyde compound of formula-4

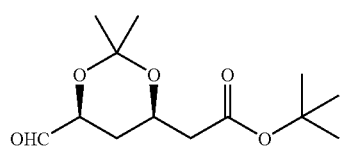

Formula-4 in presence of an alkali and alkaline earth metal bases such as sodium hydroxide, potassium hydroxide, potassium carbonate, sodium carbonate, lithium carbonate, and cesium carbonate preferably potassium carbonate in a suitable polar aprotic solvent like dimethylformamide, dimethylsulfoxide, dimethyl acetamide and/or toluene and/or mixtures thereof, preferably dimethyl sulfoxide gives condensed product, which in-situ reacting with trifluoroacetic acid in a suitable solvent like aqueous acetonitrile followed by basic hydrolysis of the obtained product in aqueous acetonitrile which is further reacting with suitable organic amine base like tertiarybutyl amine in a suitable solvent like acetonitrile to give the rosuvastatin tertiarybutyl amine compound of formula-5A followed by the purification in a suitable alcohol solvents like methanol, ethanol and isopropyl alcohol and/or acetonitrile and/or mixtures thereof preferably in a mixture of acetonitrile and isopropyl alcohol to give pure rosuvastatin tertiarybutyl amine compound of formula-5A, Formula-5A

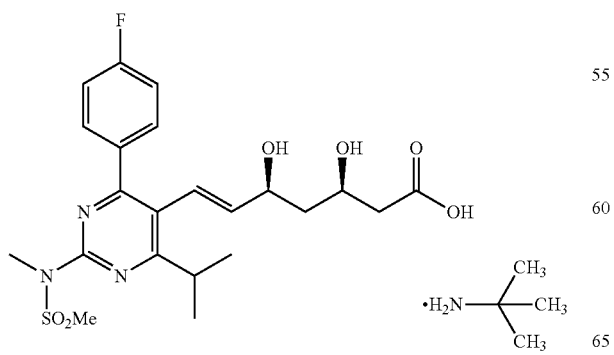

b) Converting the rosuvastatin tertiarybutyl amine compound of formula-5A into its calcium salt compound of formula-1A by treating the tertiarybutyl amine compound of formula-5A with an alkali base such as sodium hydroxide, potassium hydroxide and lithium hydroxide preferably sodium hydroxide or potassium hydroxide and setting the pH of the reaction mixture to 9.1 by extracting the organic amine salt compound of formula-5A with tertiarybutyl acetate or by direct distillation, c) Optionally isolating the corresponding sodium or potassium salt of rosuvastatin compound of formula-6A or 6AA, Formula-6A

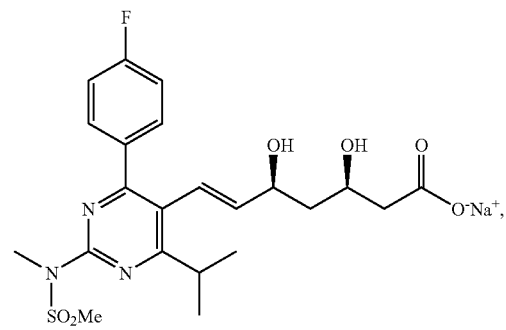

Formula-6AA

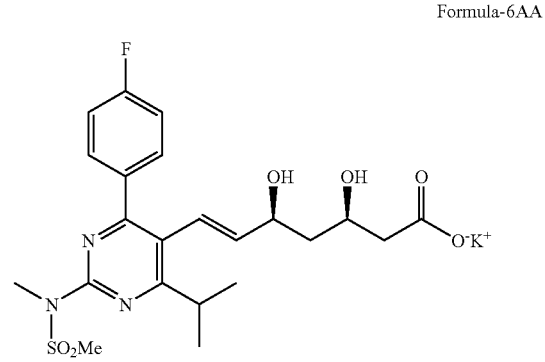

d) Adding the aqueous phase of the reaction mixture or an aqueous solution of rosuvastatin sodium or potassium salt to a solution of calcium chloride or calcium acetate in a suitable solvent such as water.

According to the present invention, a preferred one-pot synthesis is provided for the preparation of rosuvastatin calcium salt compound of formula-1A, which comprises of the following steps a) Reacting the sulfone compound of formula-3A Formula-3A

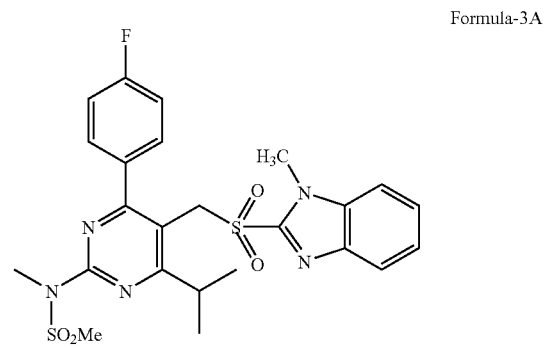 [SMILES: CC(C)c1nc(N(C)S(C)(=O)=O)nc(-c2ccc(F)cc2)c1CS(=O)(=O)c1nc2ccccc2n1C]

With an amide compound of formula-7A

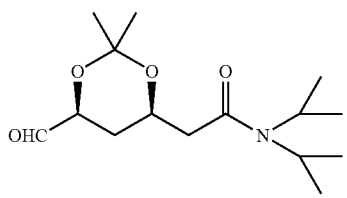
Formula-7A in presence of an alkali and alkaline earth metal bases such as sodium hydroxide, potassium hydroxide, potassium carbonate, sodium carbonate, lithium carbonate, and cesium carbonate preferably potassium carbonate in a suitable polar aprotic solvent like dimethylformamide, dimethylsulfoxide, dimethylacetamide or mixtures thereof, preferably dimethyl sulfoxide to provide the compound of general formula-8A,

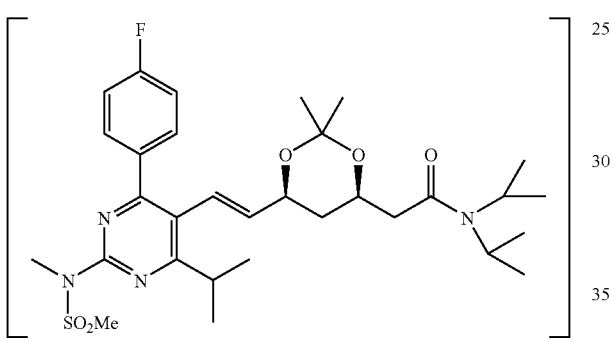
Formula-8A which in-situ reacting with suitable acid such as hydrochloric acid, acetic acid, sulfuric acid in a suitable solvent to give the diol compound of general formula-9A,

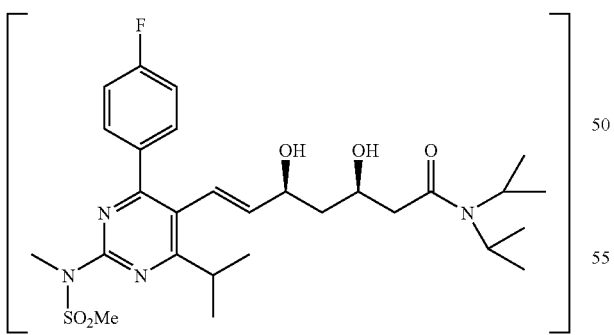
Formula-9A which upon treating with an alkali base such as sodium hydroxide, potassium hydroxide and lithium hydroxide to form the corresponding alkali salt then further treating with an organic amine base like n-butyl amine, isobutyl amine, (+/−) 2-butyl amine, tertiarybutyl amine preferably tertiarybutyl amine to give rosuvastatin tertiarybutyl amine compound of formula-5A,

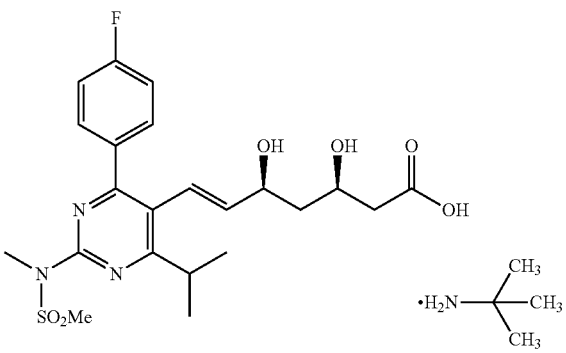
Formula-5A b) Converting rosuvastatin tertiarybutyl amine compound of formula-5A into its rosuvastatin calcium compound of formula-1A by treating the tertiarybutyl amine compound of formula-5A with an alkali base such as sodium hydroxide, potassium hydroxide and lithium hydroxide preferably sodium hydroxide or potassium hydroxide and setting the pH of the reaction mixture to 9.1 by extracting the rosuvastatin tertiarybutyl amine salt compound of formula-5A with tertiary butyl acetate or by direct distillation, c) Optionally isolating the corresponding sodium or potassium salt of rosuvastatin compound of formula-6A or 6AA,

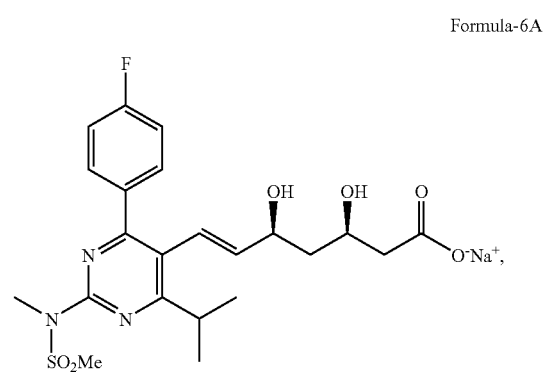 [SMILES: CC(C)c1nc(N(C)S(C)(=O)=O)nc(-c2ccc(F)cc2)c1/C=C/[C@@H](O)C[C@@H](O)CC(=O)N(C(C)C)C(C)C]
Formula-6A

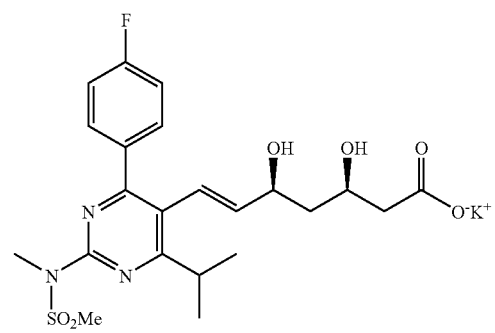
Formula-6AA d) Adding the aqueous phase of the reaction mixture or an aqueous solution of rosuvastatin sodium or potassium salt to a solution of calcium chloride or calcium acetate in a suitable solvent such as water.

According to the present invention, a preferred one-pot synthesis is provided for the preparation of rosuvastatin calcium salt compound of formula-1A

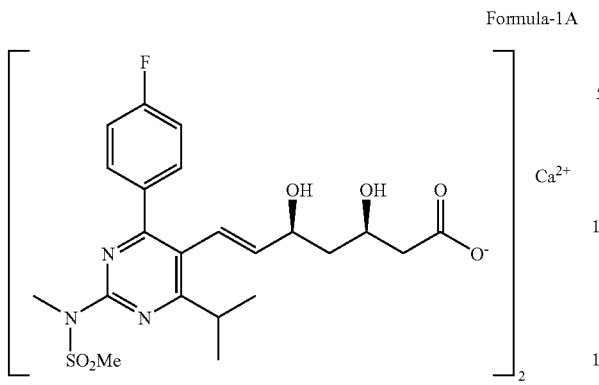

Formula-1A which comprises of the following steps
a) Reacting the sulfone compound of Formula-3A

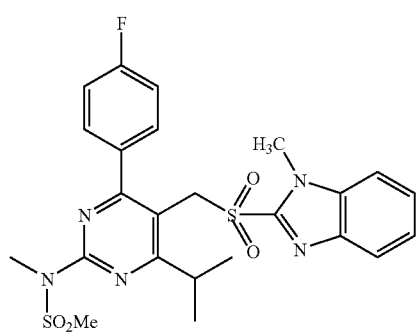

Formula-3A

With an aldehyde compound of formula-4

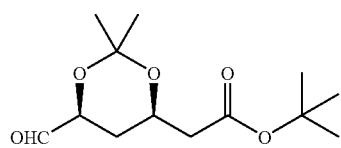

Formula-4 in presence of an alkali and alkaline earth metal bases such as sodium hydroxide, potassium hydroxide, potassium carbonate, sodium carbonate, lithium carbonate, and cesium carbonate preferably potassium carbonate in a suitable polar aprotic solvent like dimethylformamide, dimethylsulfoxide, dimethylacetamide or mixtures thereof, preferably dimethyl sulfoxide to provide condensed compound, which in-situ reacting with trifluoroacetic acid to give the lactone compound, which is further in-situ reacting with diisopropylamine to give the diisopropyl amide compound of formula-10A,

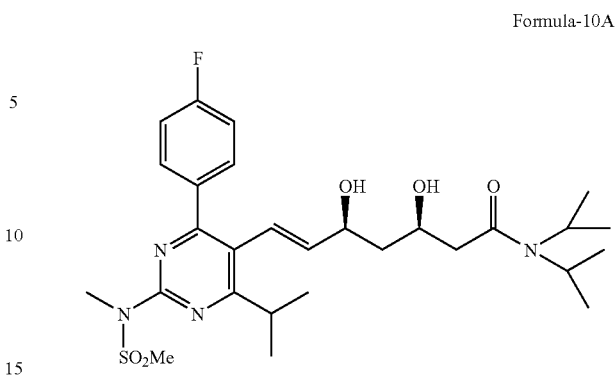

Formula-10A a) Reacting the diisopropyl amide compound of formula-10A with an alkali base such as sodium hydroxide, potassium hydroxide and lithium hydroxide followed by treating with an organic amine base like n-butyl amine, isobutyl amine, (+/−) 2-butyl amine, tertiarybutyl amine, preferably tertiarybutyl amine to give rosuvastatin tertiarybutyl amine compound of formula-5A,

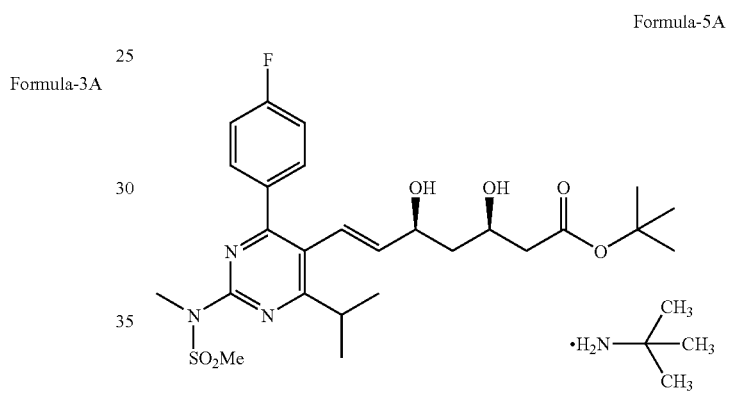

Formula-5A c) Converting the rosuvastatin tertiarybutyl amine compound of formula-5A into rosuvastatin calcium salt compound of formula-1A by treating the rosuvastatin tertiarybutyl amine compound of formula-5A with an alkali base such as sodium hydroxide, potassium hydroxide and lithium hydroxide preferably sodium hydroxide or potassium hydroxide and setting the pH of the reaction mixture to 9.1 by extracting the rosuvastatin tertiarybutyl amine with tertiary butyl acetate or by direct distillation, d) Optionally isolating the corresponding sodium or potassium salt of rosuvastatin compound of formula-6A or 6AA,

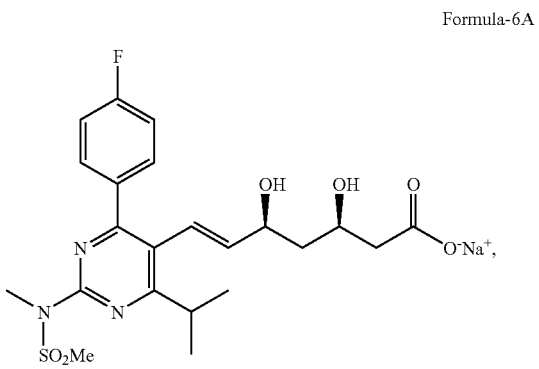

Formula-6A

Formula-6AA

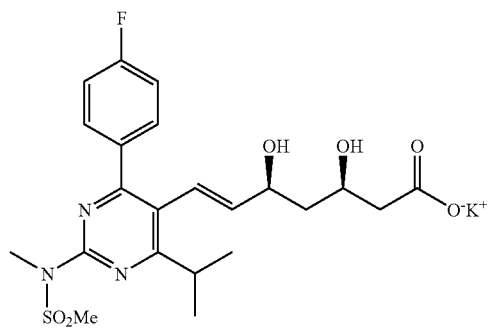

e) Adding the aqueous phase of the reaction mixture or an aqueous solution of rosuvastatin sodium or potassium salt to a solution of calcium chloride or calcium acetate in a suitable solvent such as water.

According to the present invention, a preferred one-pot synthesis is provided for the preparation of rosuvastatin calcium salt compound of formula-1A Formula-1A

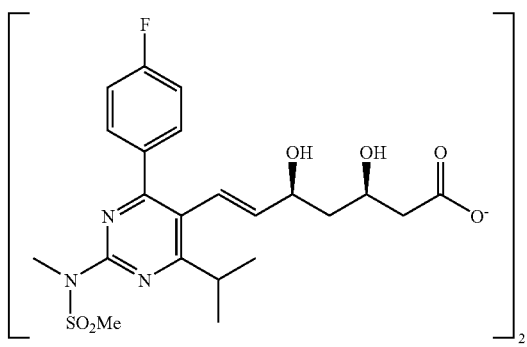

The one-pot synthesis for the preparation of rosuvastatin calcium compound of formula-1A comprises of the following steps a) Reacting the sulfone compound of formula-3A Formula-3A

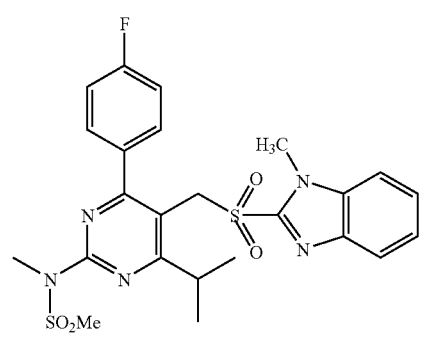

With an aldehyde compound of formula-4

Formula-4

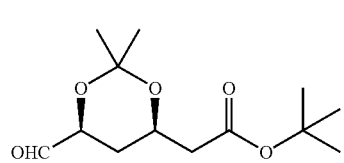

in presence of an alkali and/or alkaline earth metal bases such as sodium hydroxide, potassium hydroxide, potassium carbonate, sodium carbonate, lithium carbonate, and cesium carbonate preferably potassium carbonate in a suitable polar aprotic solvent like dimethylformamide, dimethylsulfoxide, dimethylacetamide or mixtures thereof, preferably dimethyl sulfoxide to provide the compound of formula-11A Formula-11A

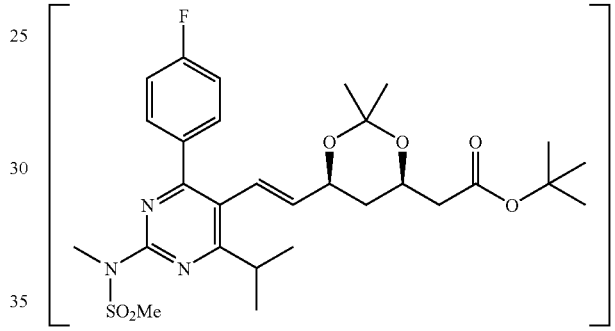

which in-situ reacting with suitable acid such as hydrochloric acid, acetic acid, sulfuric acid in a suitable solvent to give the diol compound of formula-12A, Formula-12A

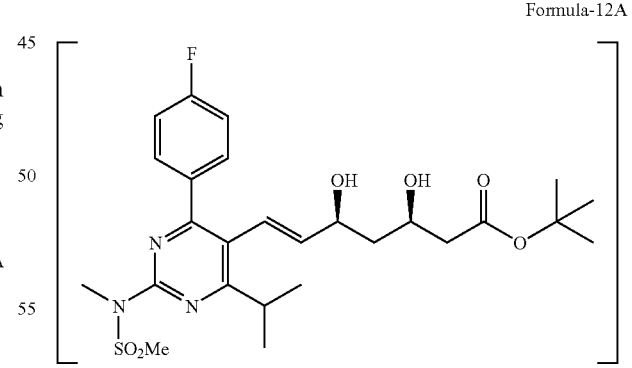

which upon treating with an alkali base such as sodium hydroxide, potassium hydroxide and lithium hydroxide to form the corresponding alkali salt then further treating with an organic amine base like n-butyl amine, isobutyl amine, (+/−) 2-butyl amine, tertiary-butyl amine, preferably tertiarybutyl amine to give rosuvastatin tertiarybutyl amine compound of formula-5A, Formula-5A

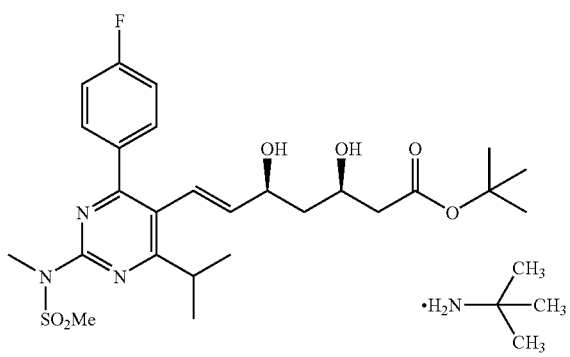

a) Converting the rosuvastatin tertiarybutyl amine compound of formula-5A into rosuvastatin calcium salt compound of formula-1A by treating the rosuvastatin tertiarybutyl amine compound of formula-5A with an alkali base such as sodium hydroxide, potassium hydroxide and lithium hydroxide preferably sodium hydroxide or potassium hydroxide and setting the pH of the reaction mixture to 9.1 by extracting the rosuvastatin tertiarybutyl amine with tertiary butyl acetate or by direct distillation
b) Optionally isolating the corresponding sodium or potassium salt of rosuvastatin compound of Formula-6A or 6AA, Formula-6A

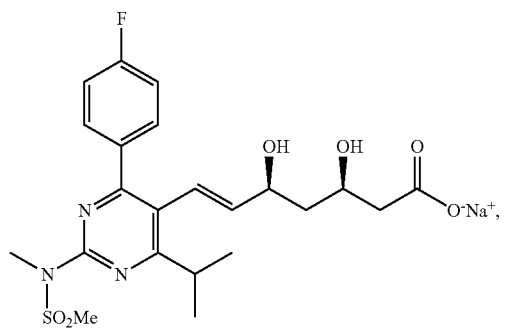

Formula-6AA

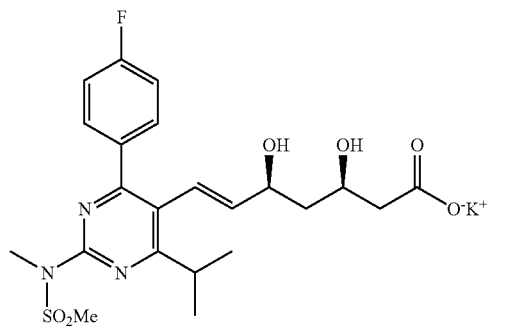

d) Adding the aqueous phase of the reaction mixture or an aqueous solution of rosuvastatin sodium or potassium salt to a solution of calcium chloride or calcium acetate in a suitable solvent such as water. Thus obtained amorphous rosuvastatin calcium compound can be milled and/or micronized to get the desired particle size distribution.

According to the present invention, a preferred process is provided for preparing the preferred olefinic chiral dihydroxy acid and its pharmaceutically acceptable salts compound of formula-2a Formula-2a

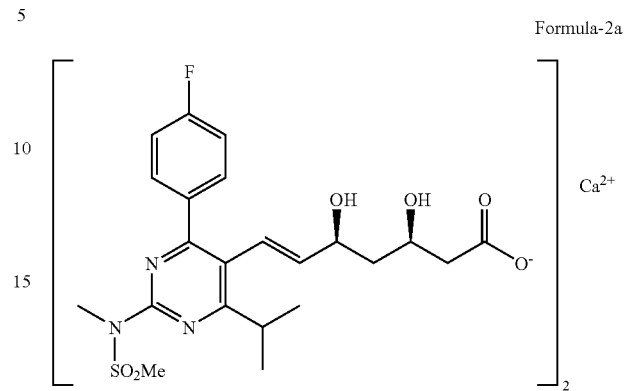

A novel process for the preparation of olefin dihydroxy acid is provided via Julia-Modified olefination which comprises of the following steps
a) Reacting sulfone compound of formula-13a Formula-13a

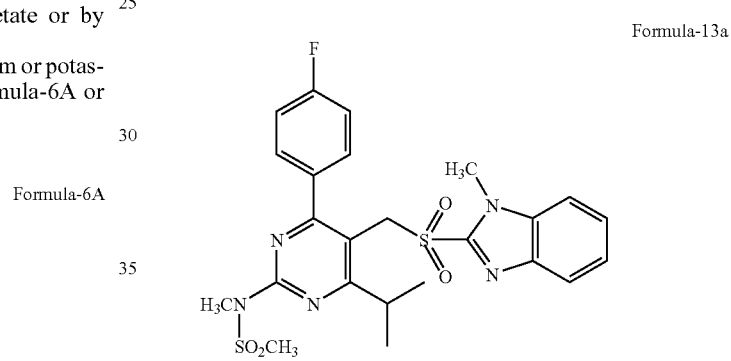

With an aldehyde compound of Formula-14a

Formula-14a in the presence of cesium carbonate or potassium carbonate in dimethyl sulfoxide to provide olefin compound of general formula-15a Formula-15a b) The olefin compound of general formula-15a may be used to form a dihydroxy acid HMG CoA reductase inhibitor by subjecting olefin compound of formula-15a to acidic conditions such as using hydrochloric acid to remove the acetonide and form diol compound, which upon treating with an alkali base such as sodium hydroxide to form sodium salt then further treating with tertiarybutyl amine to form rosuvastatin tertiarybutyl amine compound of formula-16a, Formula-16a

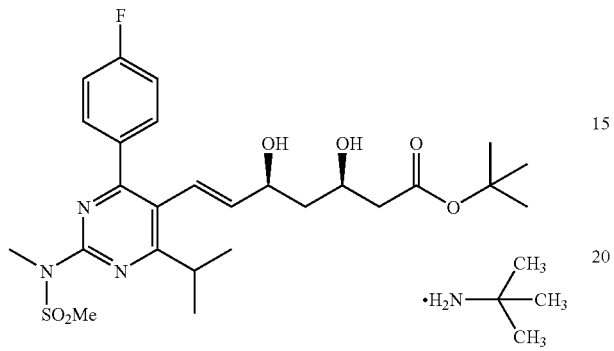

b) Converting the rosuvastatin tertiarybutyl amine compound of formula-16a into rosuvastatin calcium salt compound of formula-2a by treating the rosuvastatin tertiarybutyl amine compound of formula-16a with an alkali base such as sodium hydroxide, potassium hydroxide and lithium hydroxide and setting the pH of the reaction mixture to 9.1 by extracting the rosuvastatin tertiarybutyl amine with tertiary butyl acetate or by direct distillation followed by adding the aqueous phase of the reaction mixture to a solution of calcium chloride or calcium acetate in a suitable solvent such as water.

In accordance with the present invention, a preferred process is provided for preparing the preferred sulfone compound of formula 13a, Formula-13c

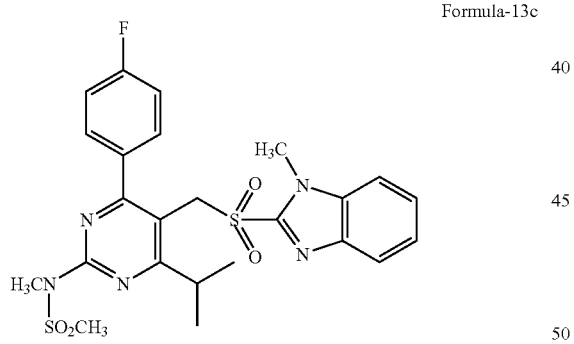

which comprises of the following steps a) Treating a solution of compound of Formula-18a.

Formula-18a

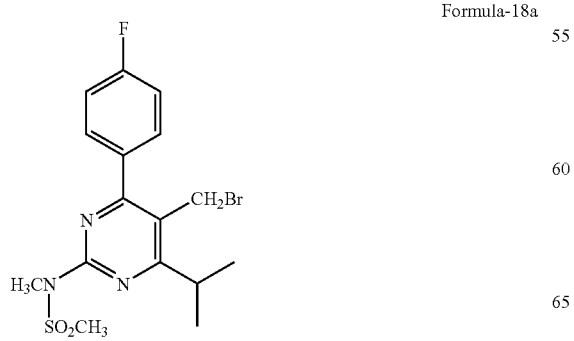

with benzimidazole-thiol compound of formula-19c in presence of sodium hydroxide in dimethyl formamide or in acetone, Formula-19c

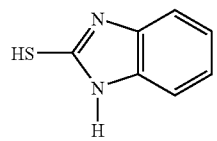

to provide a novel sulfide compound of formula-20c

Formula-20c

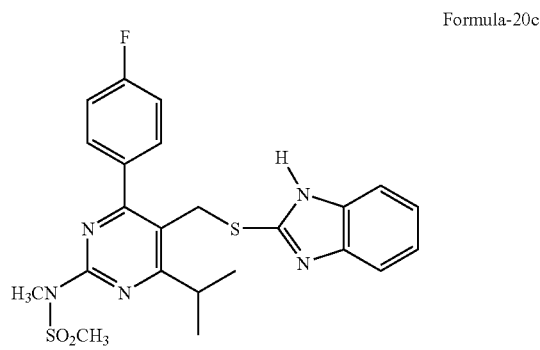

and methylating the compound of formula-20c using methylating agent like dimethyl sulfate to provide N-methyl sulfide compound of formula-27, Formula-27

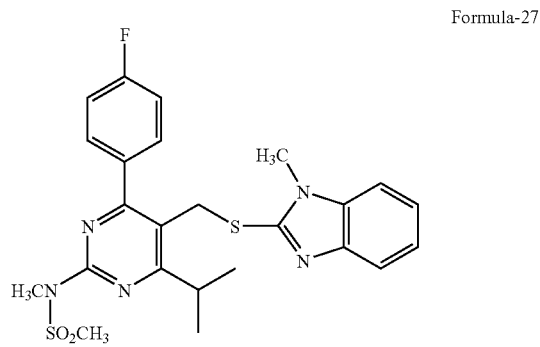

Formula-28

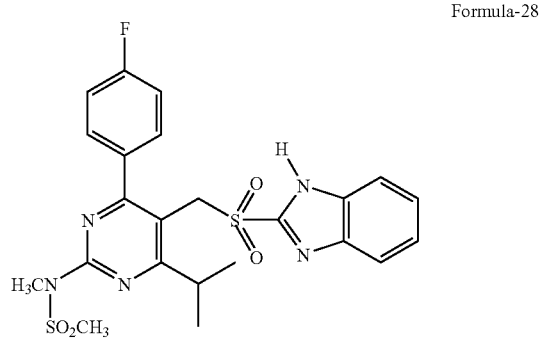

b) And oxidizing the sulfide compound of formula-27 with an oxidizing agent like metachloro perbenzoic acid, sodium hypochlorite, hydrogen peroxide, tertiary butyl hydrogen peroxide, cumene hydroperoxide, preferably hydrogen peroxdide in the presence of an appropriate catalyst like ammonium heptamolybdate in a single or biphasic system in a suitable solvent selected from alcoholic solvents like methanol, 2-proponol, ethanol, chlorosolvents like methylene chloride, chloroform, carbon tetra chloride or mixture thereof, preferably chlorosolvents, more preferably methylene chloride or oxidizing the sulfide compound of formula-20c with an oxidizing agent like metachloro perbenzoic acid, sodium hypochlorite, hydrogen peroxide, tertiary butyl hydrogen peroxide, cumene hydroperoxide, preferably hydrogen peroxdide in the presence of an appropriate catalyst like ammonium molybdate in a single or biphasic system in a suitable solvent selected from alcoholic solvents like methanol, 2-proponol, ethanol, chlorosolvents like methylene chloride, chloroform, carbon tetra chloride or mixture thereof, preferably chlorosolvents, more preferably methylene chloride and then methylating the obtained sulfone compound of formula-28, to provide the novel sulfone compound of formula-13a with benzimidazole-thiol compound of formula-19c in presence of sodium hydroxide in dimethyl formamide or acetone,

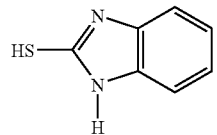

Formula-19c to provide a novel sulfide compound of formula-20c

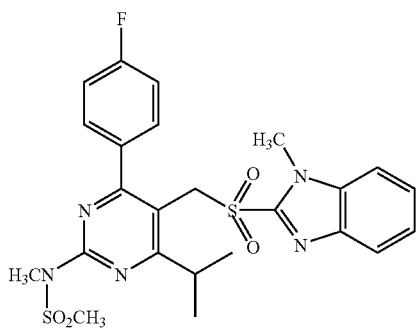

Formula-13c

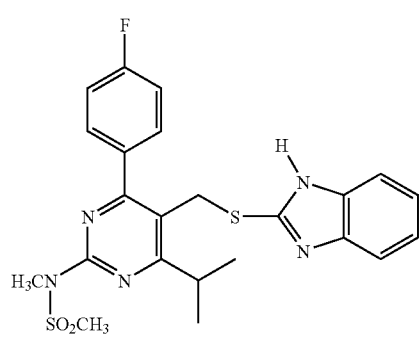

Formula-20c

In accordance with the present invention, a preferred process is provided for preparing the preferred sulfoxide compound of formula 17a, and methylating the compound of formula-20c using methylating agent to provide N-methyl sulfide compound of formula-27

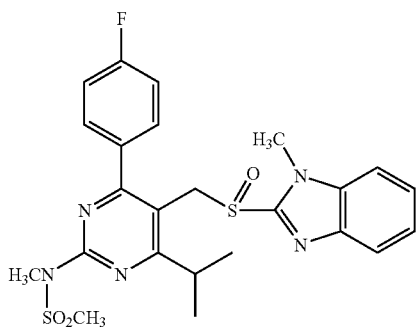

Formula-17a

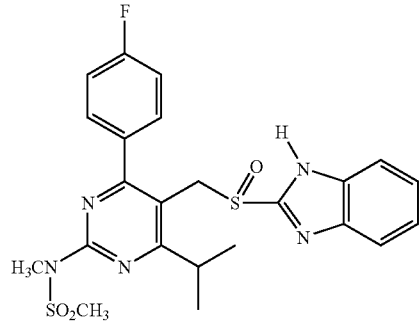

Formula-27

Which comprises of the following steps
a) Treating a solution of the compound of formula-18a

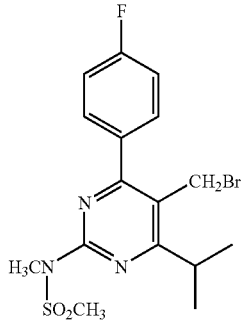

Formula-18a

Formula-29 b) And controlled oxidation of sulfide compound of formula-27 with an oxidizing agent like metachloro perbenzoic acid, sodium hypochlorite, hydrogen peroxide, tertiary butyl hydrogen peroxide, cumene hydroperoxide, preferably hydrogen peroxdide in the presence of an appropriate catalyst like ammonium molybdate in a single or biphasic system in a suitable solvent selected from alcoholic solvents like methanol, 2-proponol, ethanol, chlorosolvents like methylene chloride, chloroform, carbon tetra chloride or mixture thereof, preferably chlorosolvents, more preferably methylene chloride or controlled oxidation of sulfide compound of formula-20c with an oxidizing agent like metachloro perbenzoic acid, sodium hypochlorite, hydrogen peroxide, tertiary butyl hydrogen peroxide, cumene hydroperoxide, preferably hydrogen peroxdide in the presence of an appropriate catalyst like ammonium molybdate in a single or biphasic system in a suitable solvent selected from alcoholic solvents like methanol, 2-proponol, ethanol, chlorosolvents like methylene chloride, chloroform, carbon tetra chloride or mixture thereof, preferably chlorosolvents, more preferably methylene chloride and then methylating the obtained sulfoxide compound of formula-29, to provide novel sulfoxide compound of formula-17c

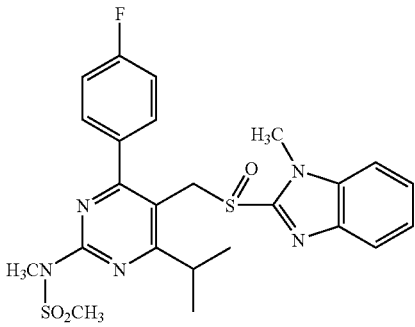

Formula-17c

The starting material compounds of general formula-13 can be prepared as per the prior art processes, Ref: U.S. Pat. No. 6,627,636; U.S. Pat. No. 5,763,675 (Pitavastatin); U.S. Pat. No. 5,354,772; U.S. Pat. No. 4,739,073 (Fluvastatin); WO 03/097614; US2004/0176401 and WO03/006439.

The starting material aldehyde compound of Formula-13 can be prepared as per the prior art processes, Ref: WO/49014; U.S. Pat. No. 6,844,437; US 20040049036 and in US 2006/0004200 and Tetrahedron Letters, Vol. 31, No. 18, pp 2545-2548, 1990

The process of the present invention may be employed to prepare pravastatin, atorvastatin, cerivastatin, fluvastatin, rosuvastatin, nisvastatin (pitavastatin), simvastatin, lovastatin and other dihydroxy acid or lactone HMG CoA reductase inhibitors.

Following are the impurities generally observed in the process for the preparation of Rosuvastatin calcium.

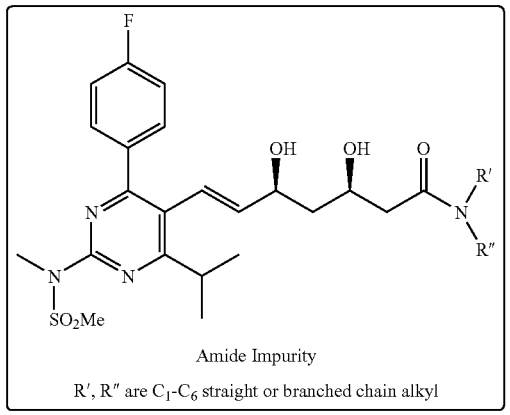

Amide Impurity
R', R" are $C_1$-$C_6$ straight or branched chain alkyl

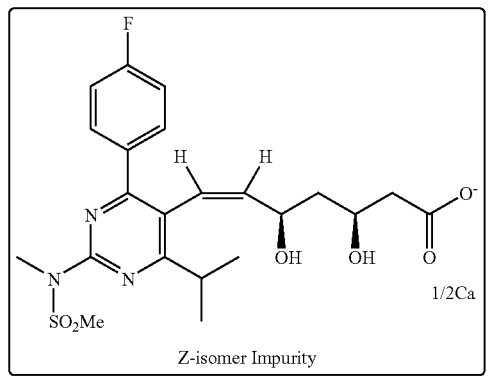

Z-isomer Impurity

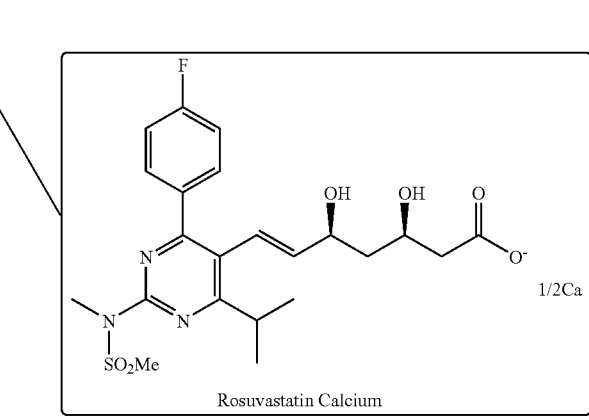

Rosuvastatin Calcium

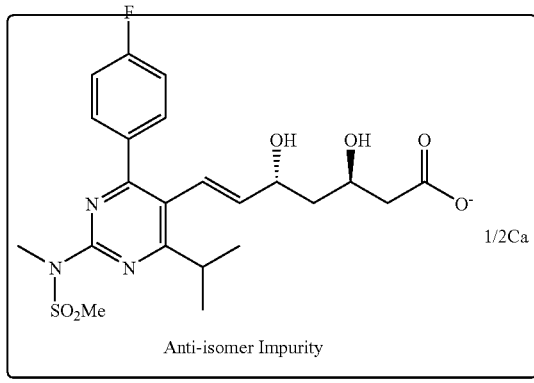
Anti-isomer Impurity
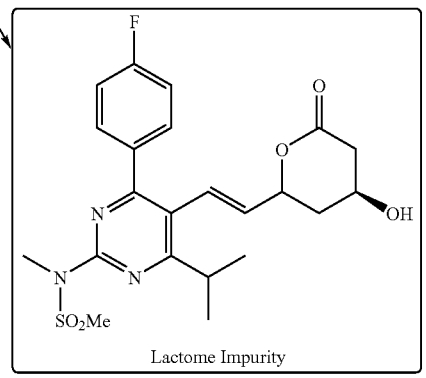
Lactome Impurity
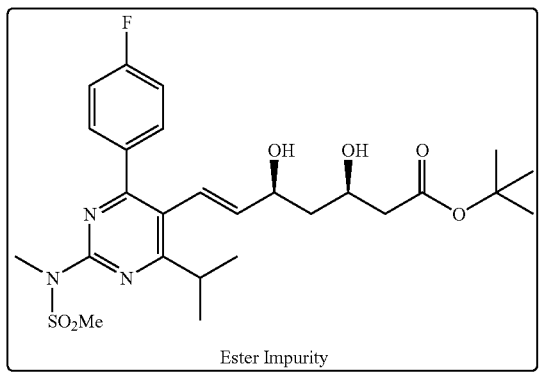
Ester Impurity
The present invention schematically represented by the following schemes
Scheme-1:
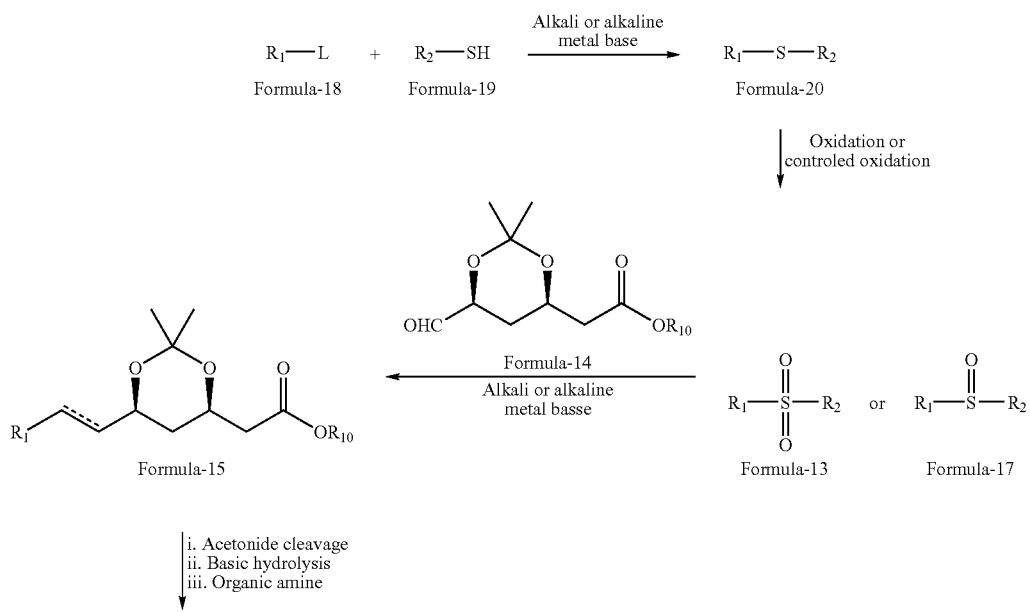

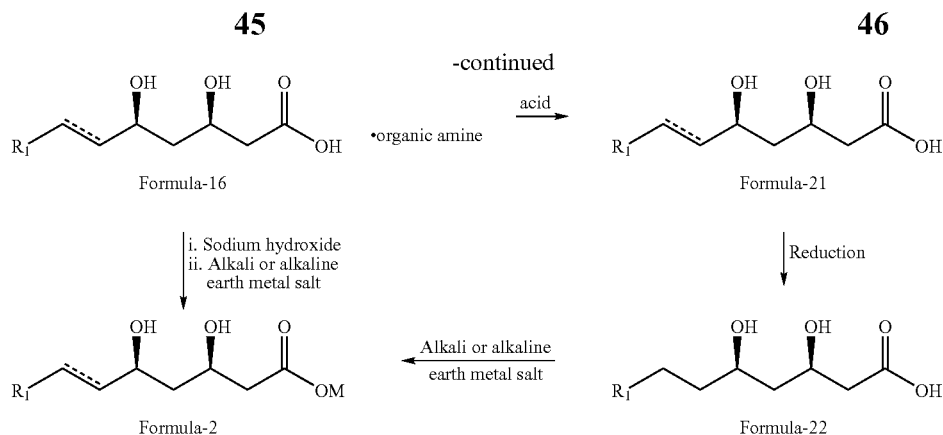
wherein M is H, $Na^+$, $K^+$, $Mg^{+2}$, $Ca^{+2}$ and $R_1$, $R_2$ and $R_{10}$ is defined as above '⇌' denotes single or double bond
Scheme-2:
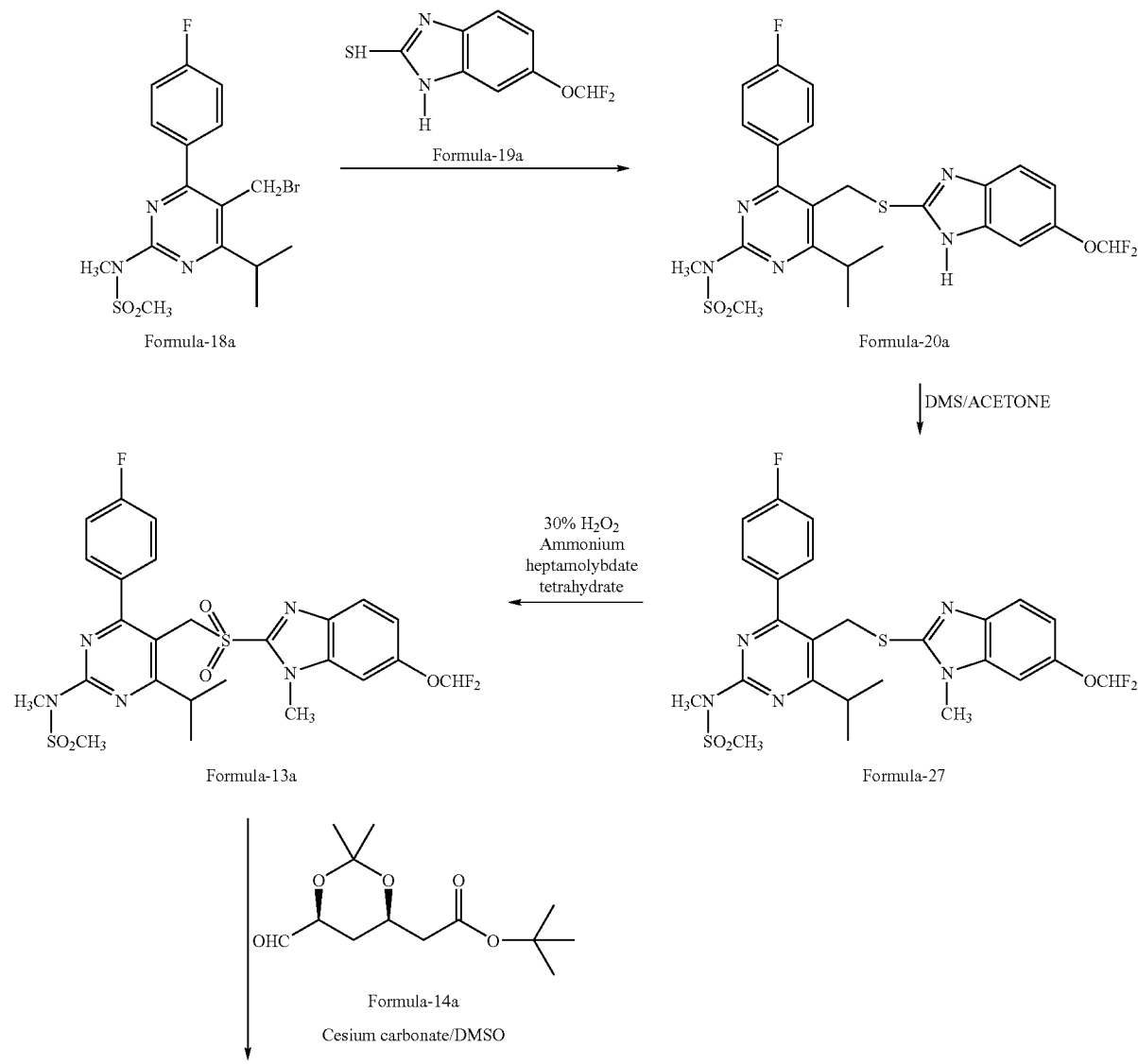

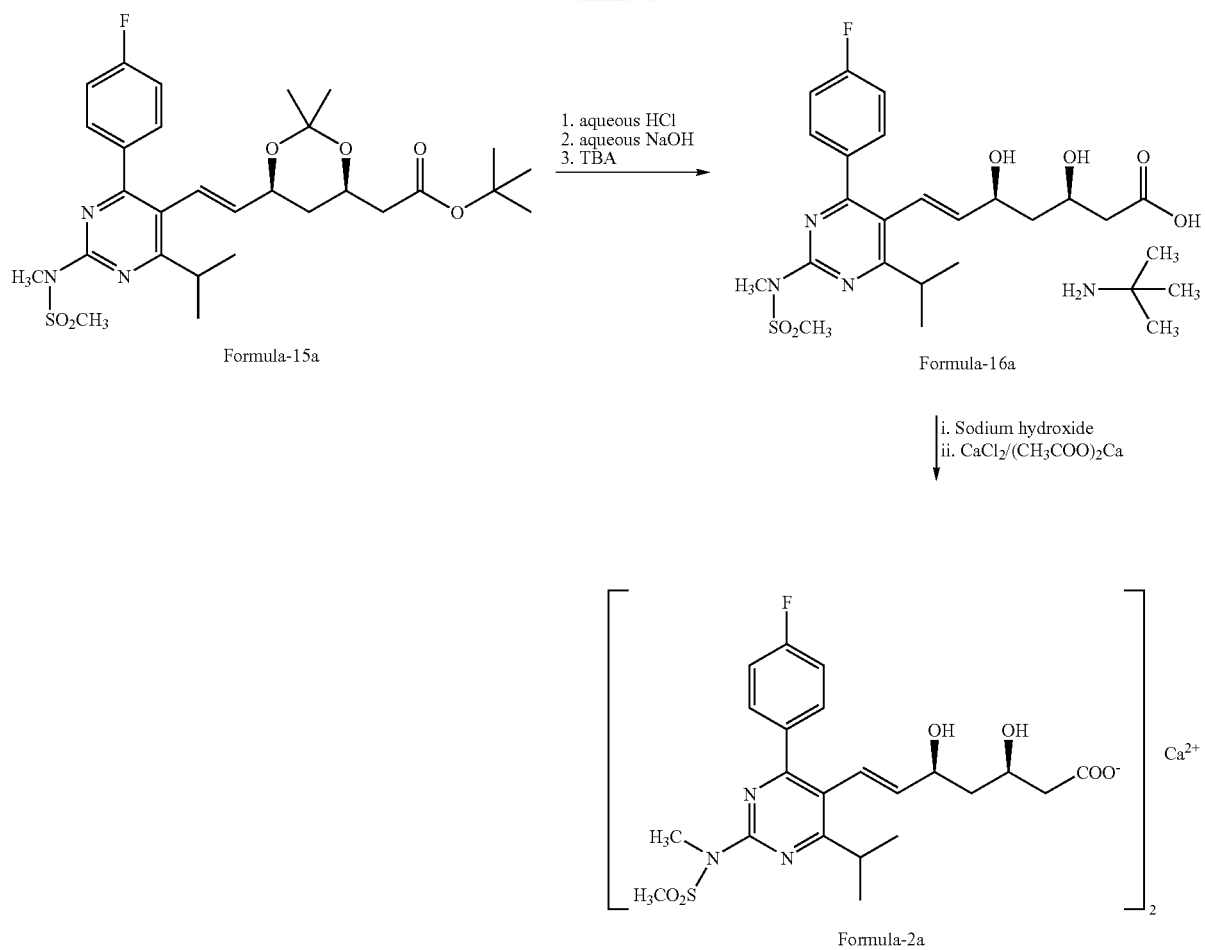
Scheme-3:
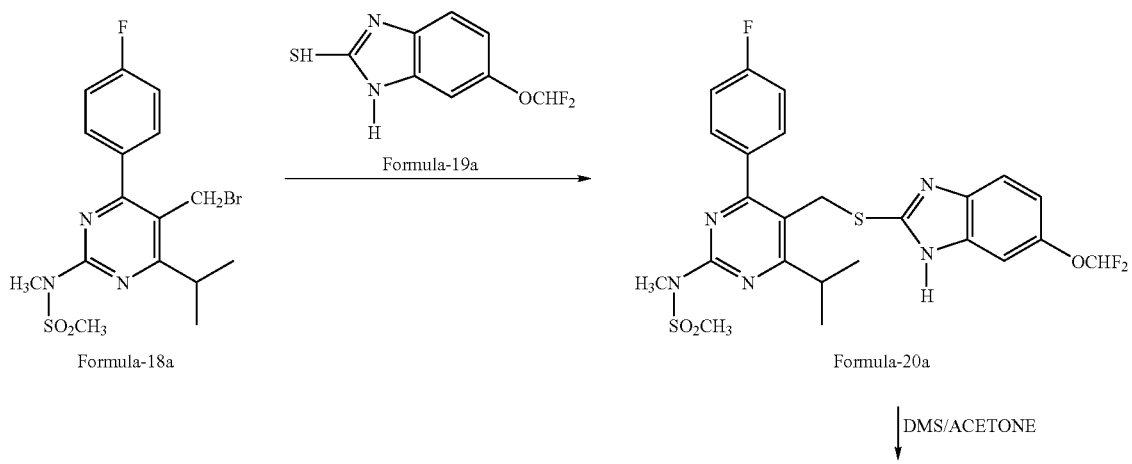

-continued
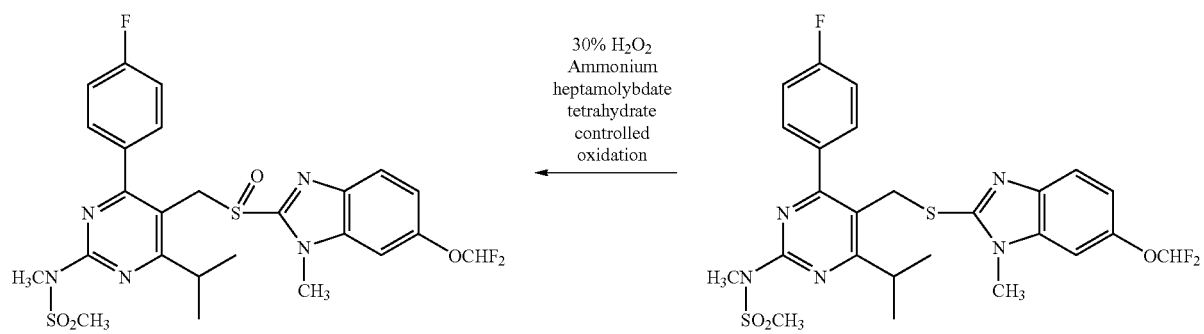
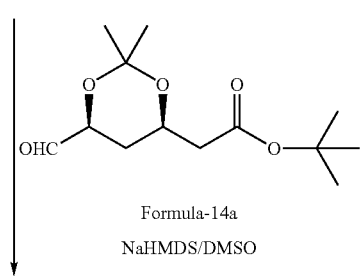
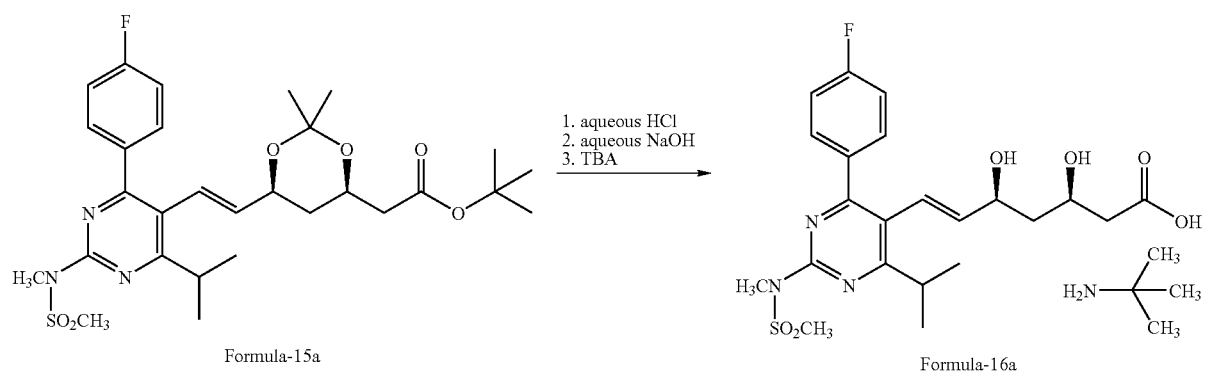
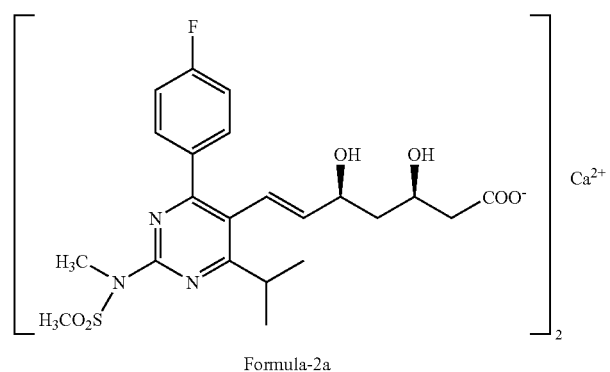

Scheme-4:
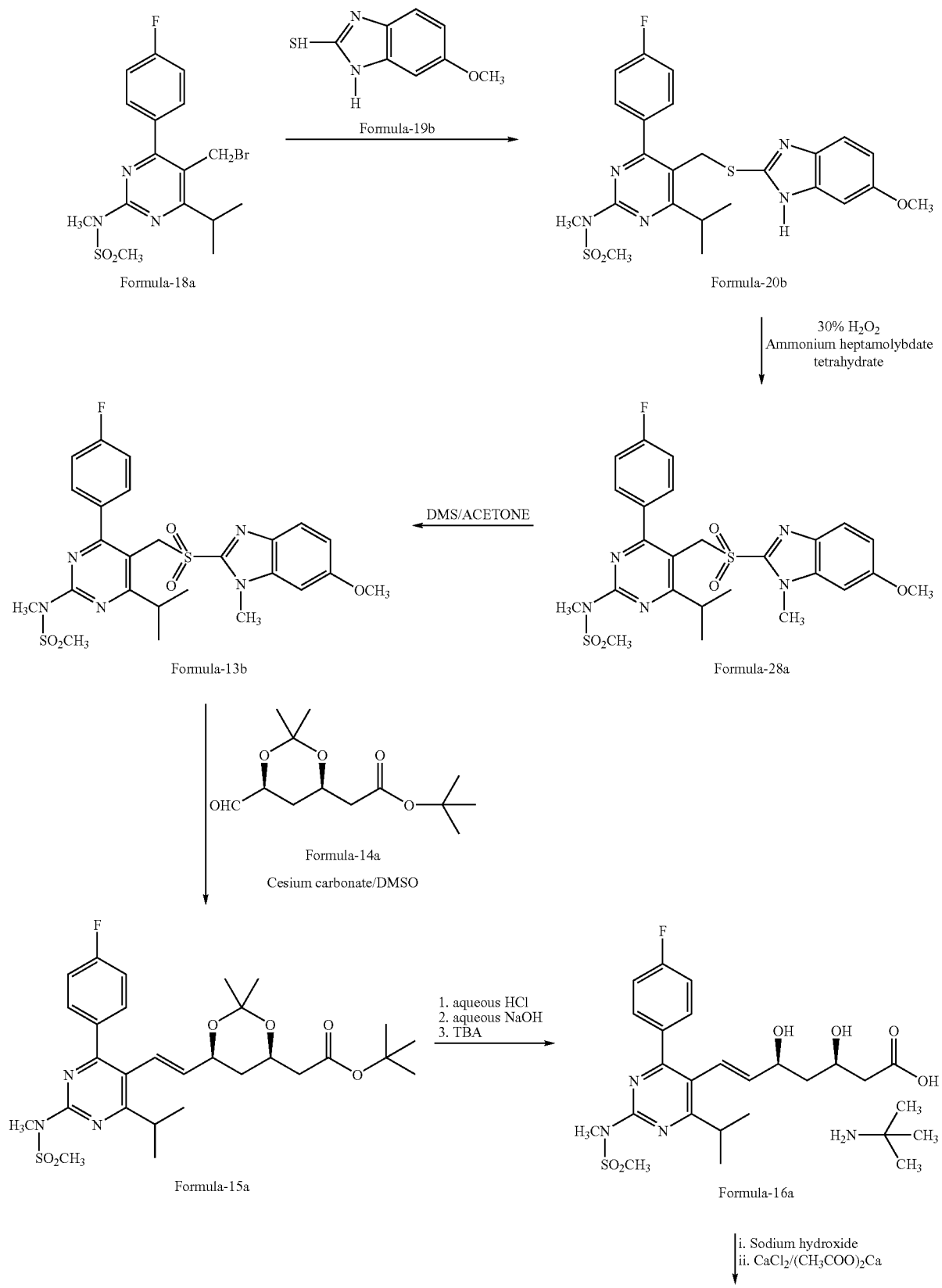

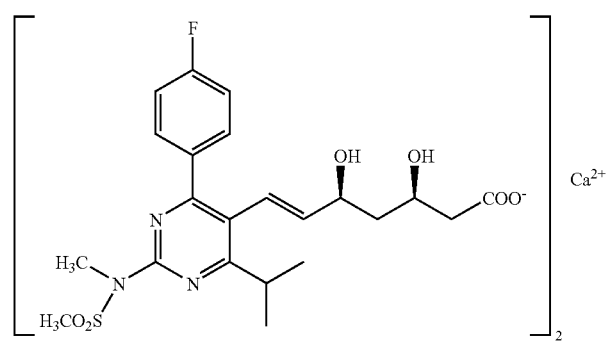
Formula-2a
Scheme-5:
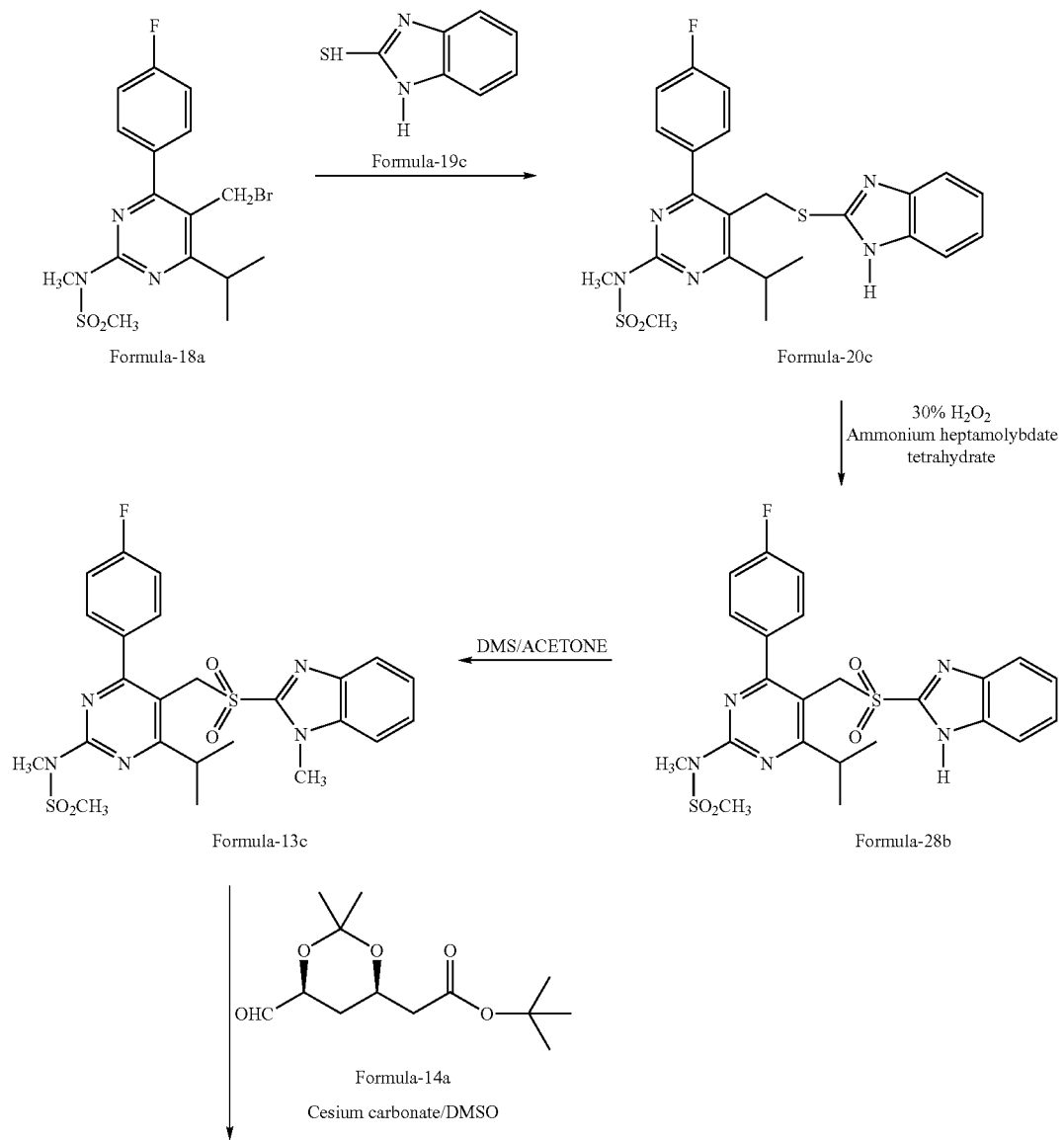

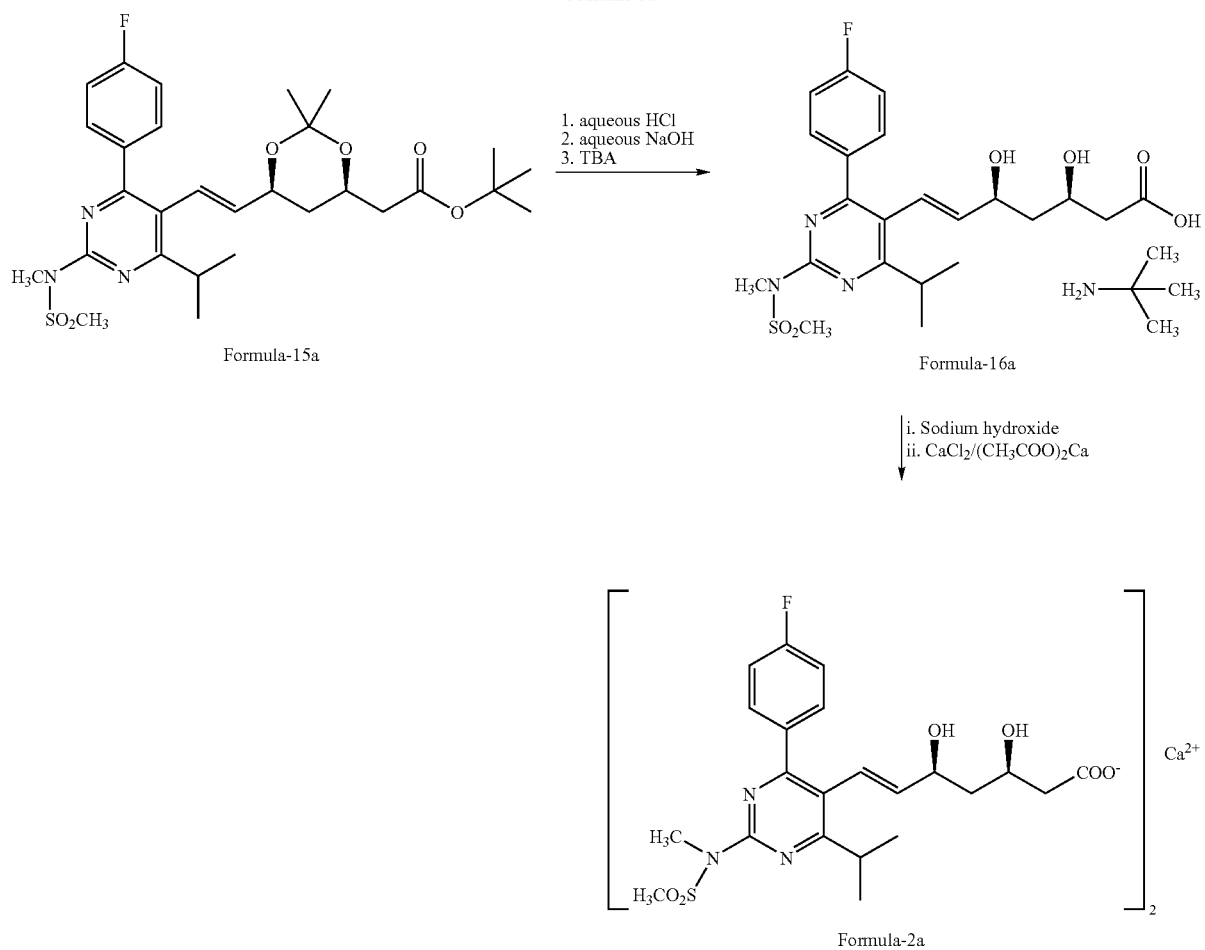
Scheme-6:
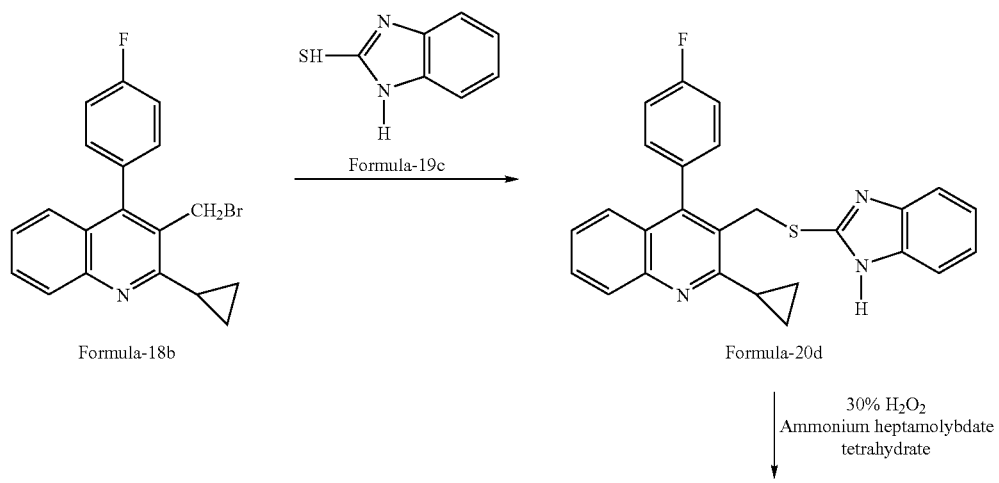

-continued
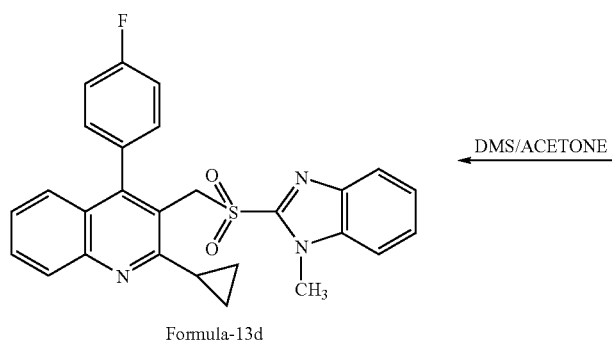# Formula-13d
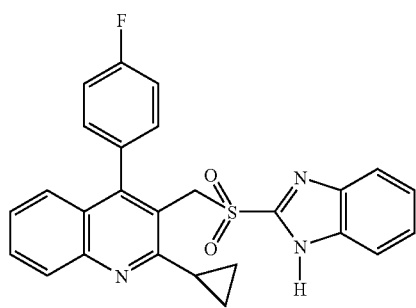# Formula-28c
DMS/ACETONE
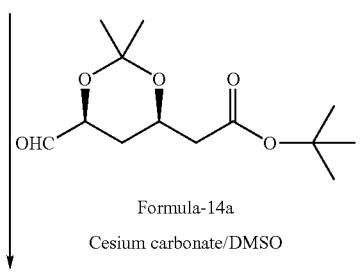# Formula-14a
Cesium carbonate/DMSO
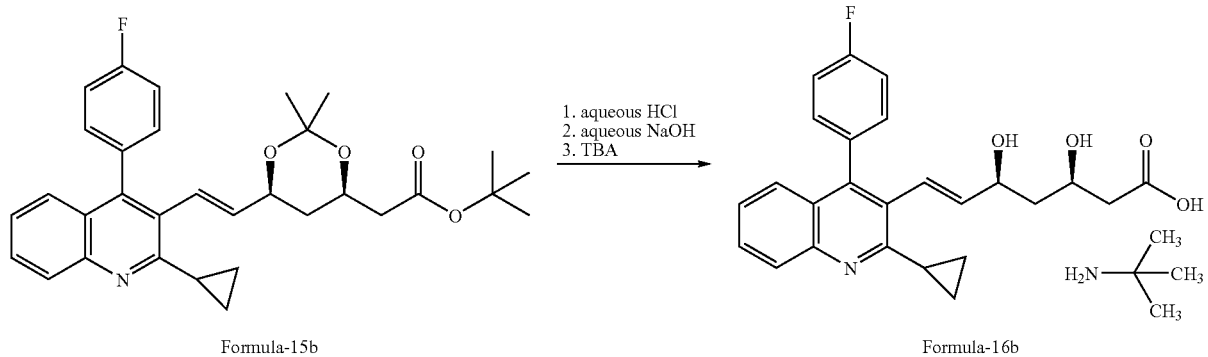
Formula-15b
1. aqueous HCl
2. aqueous NaOH
3. TBA
Formula-16b
i. Sodium hydroxide
ii. CaCl$_2$/(CH$_3$COO)$_2$Ca
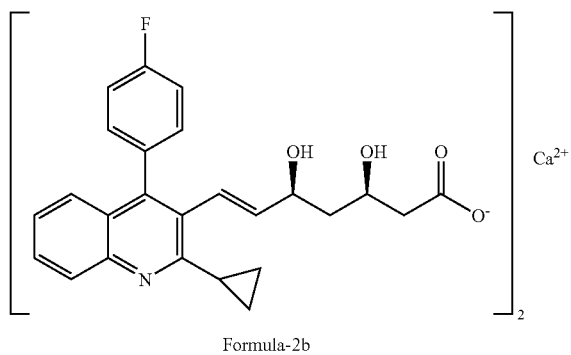
Formula-2b Scheme-7:
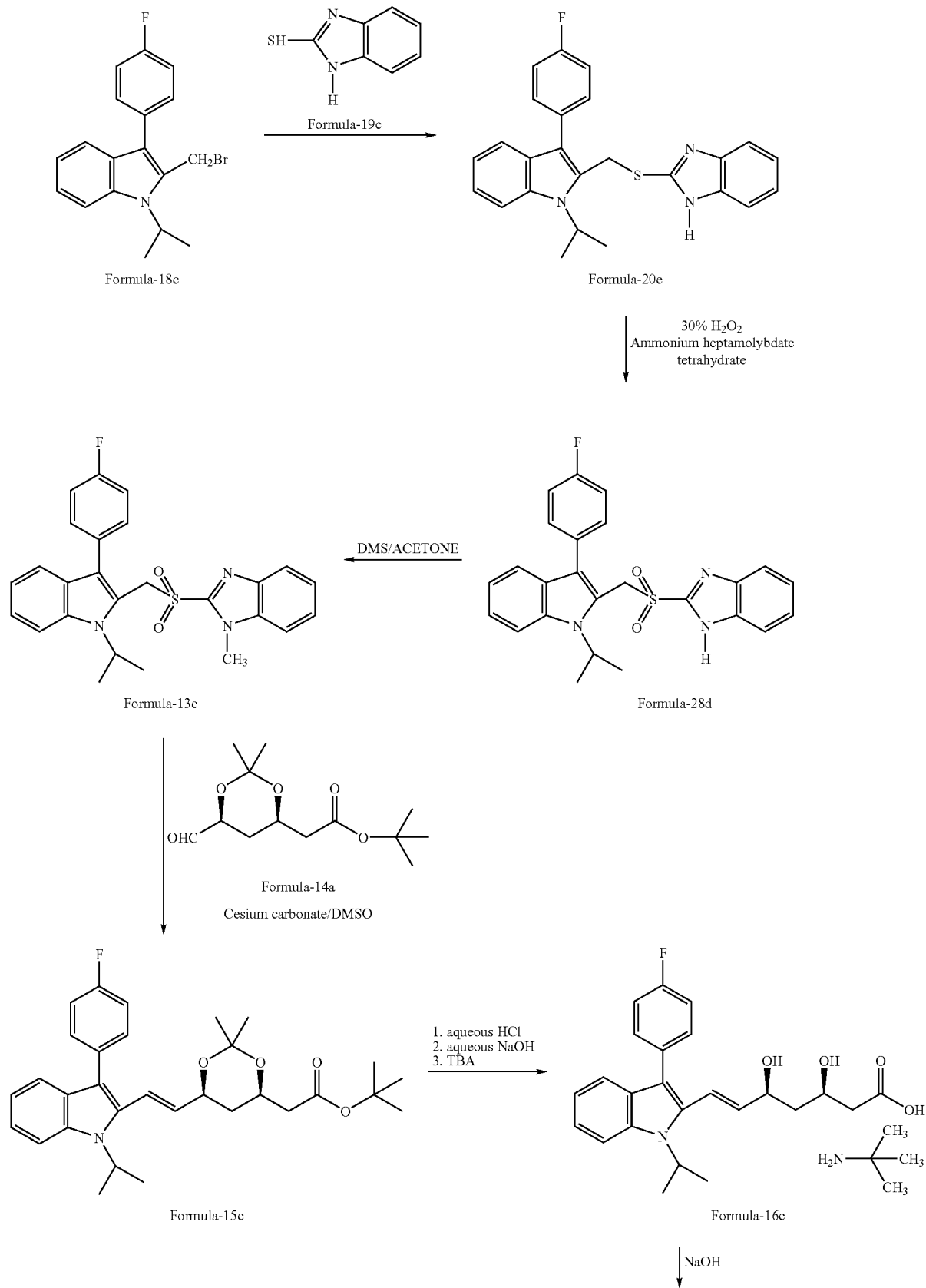

-continued
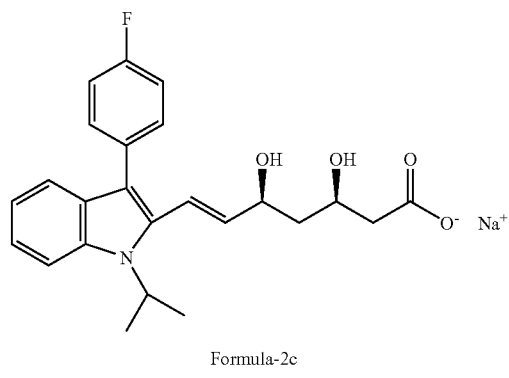 [SMILES: CC(C)n1c(/C=C/[C@@H](O)C[C@@H](O)CC(=O)[O-])c(-c2ccc(F)cc2)c2ccccc21 ; [Na+]]
Formula-2c
Scheme-8:
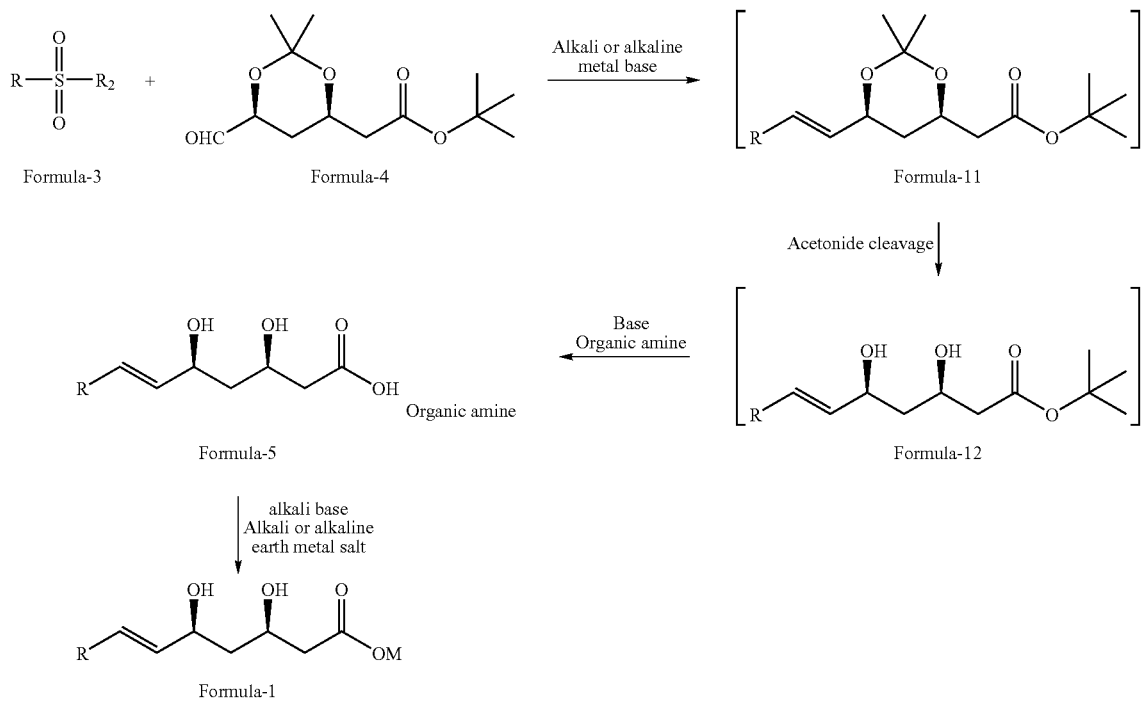
wherein $R_1$, $R_2$, Organic amine and M is defined as above
Scheme-9:
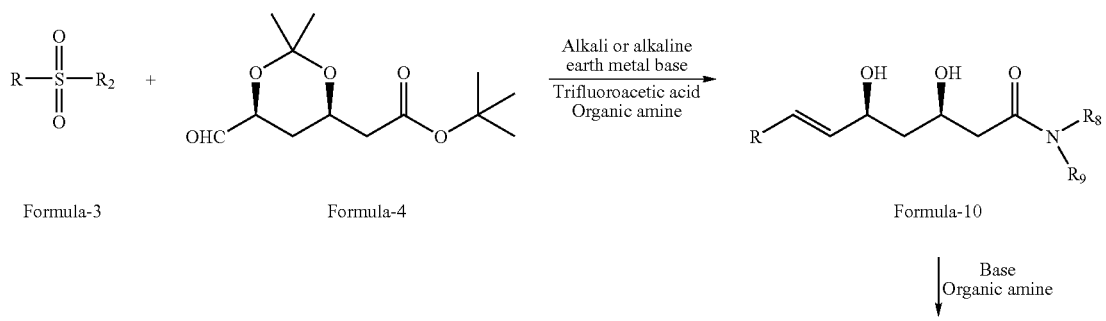

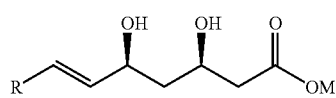
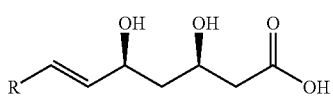
wherein R, $R_2$, $R_8$, $R_9$, organic amine and M is defined as above
Scheme-10:
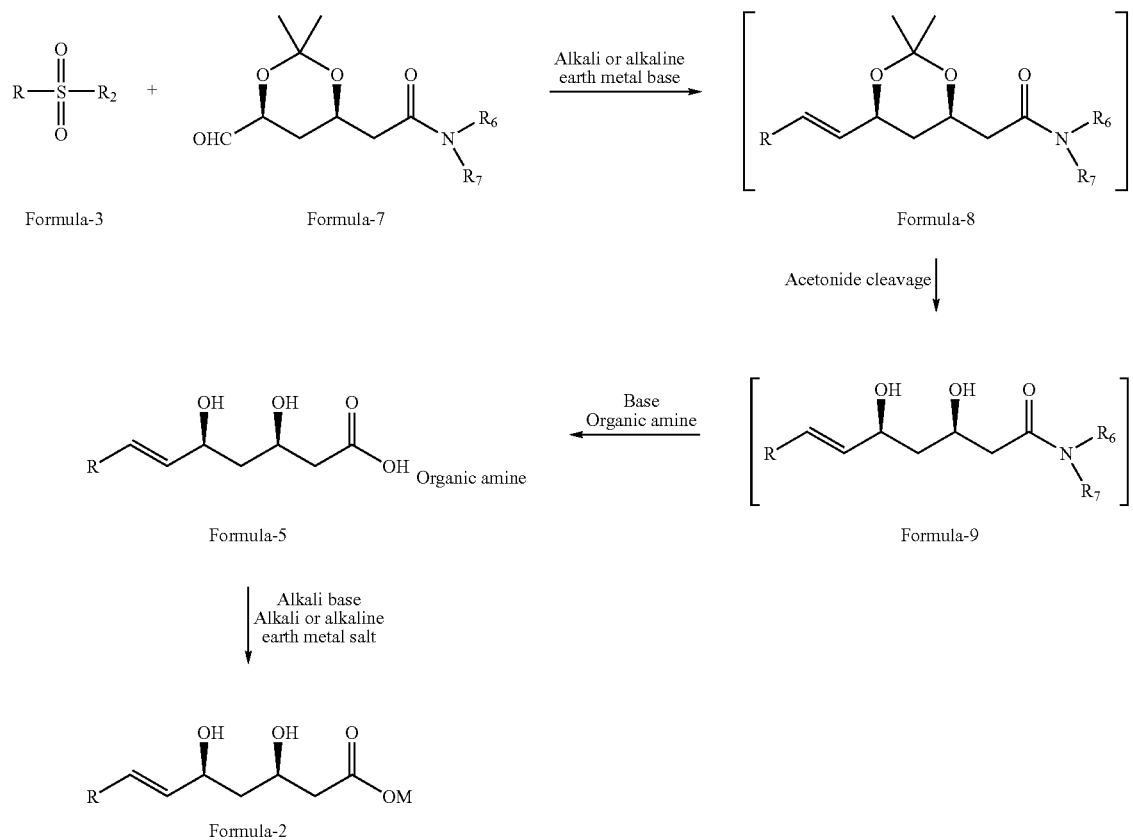
wherein R, $R_2$, $R_6$, $R_7$, Organic amine and M is defined as above
Scheme-11:
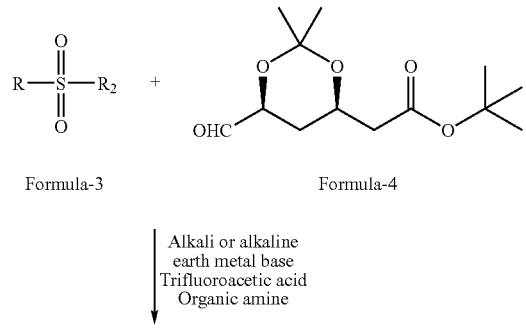
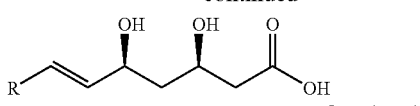
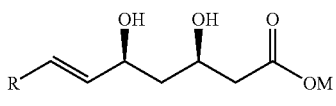
wherein R, $R_2$, organic amine and M is defined as above Scheme-12:
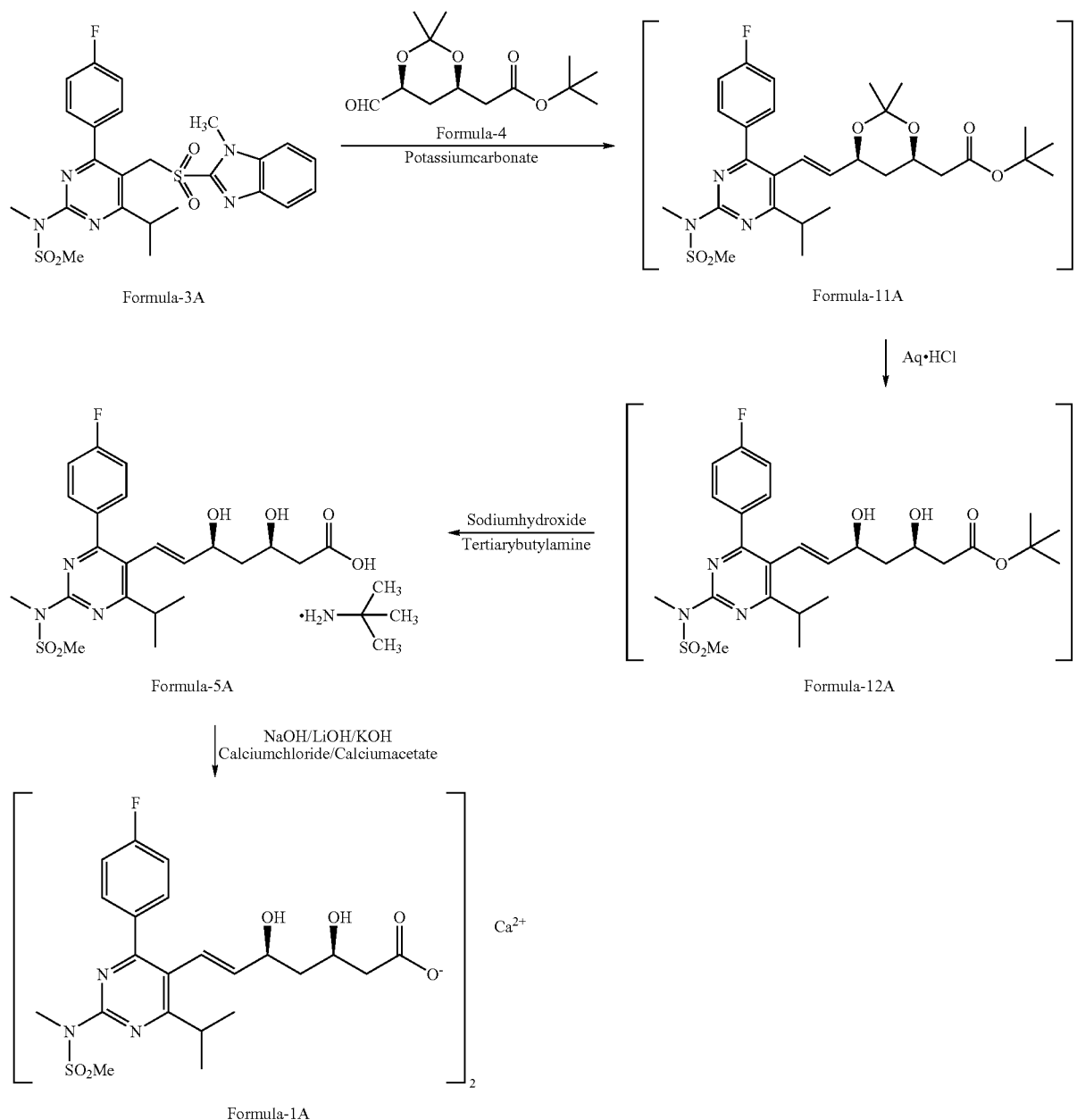
Scheme-13:
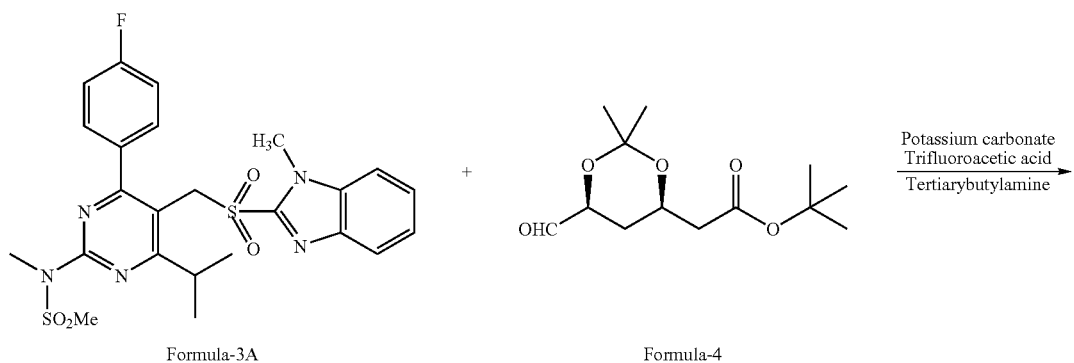

-continued
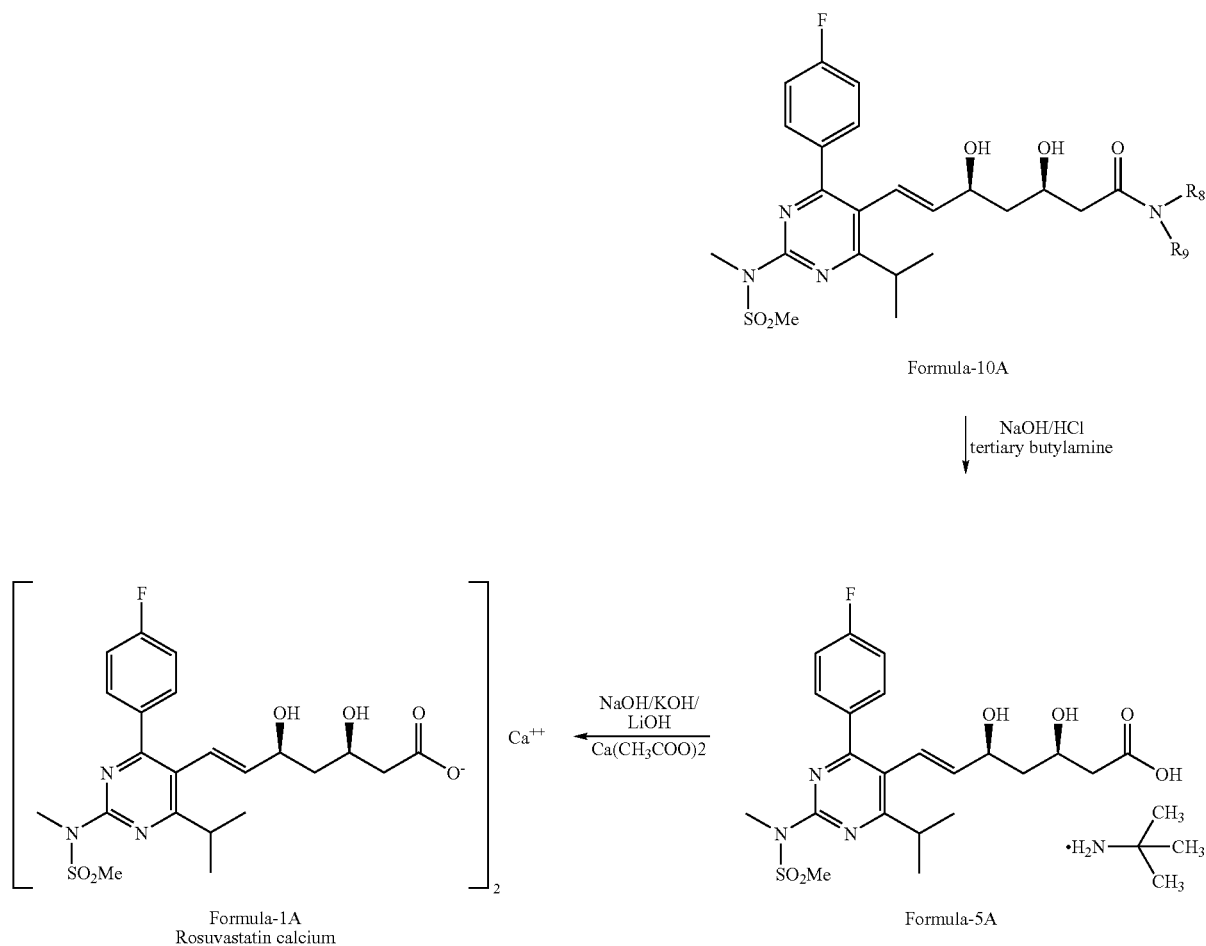
Scheme-14:
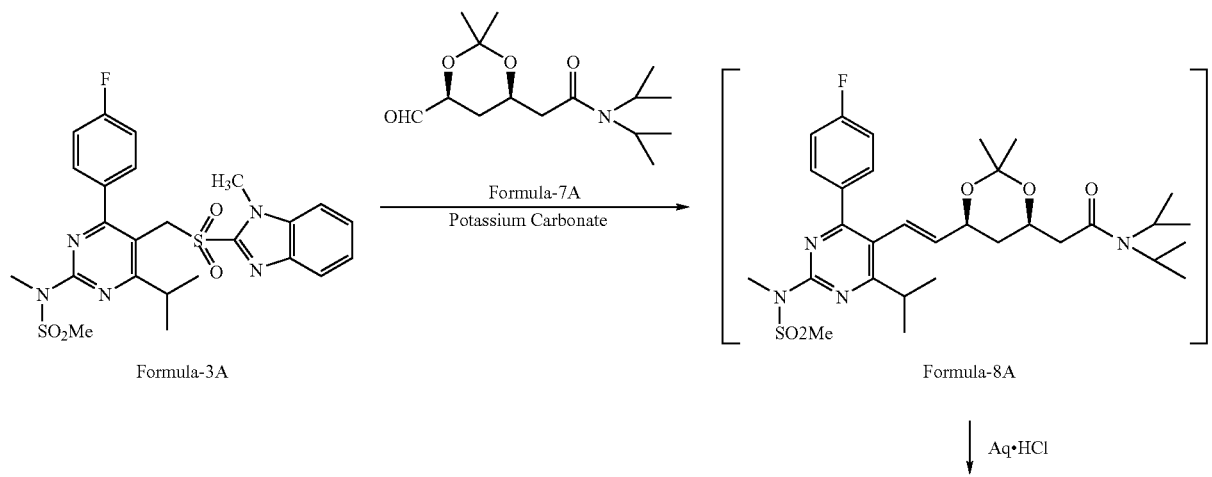

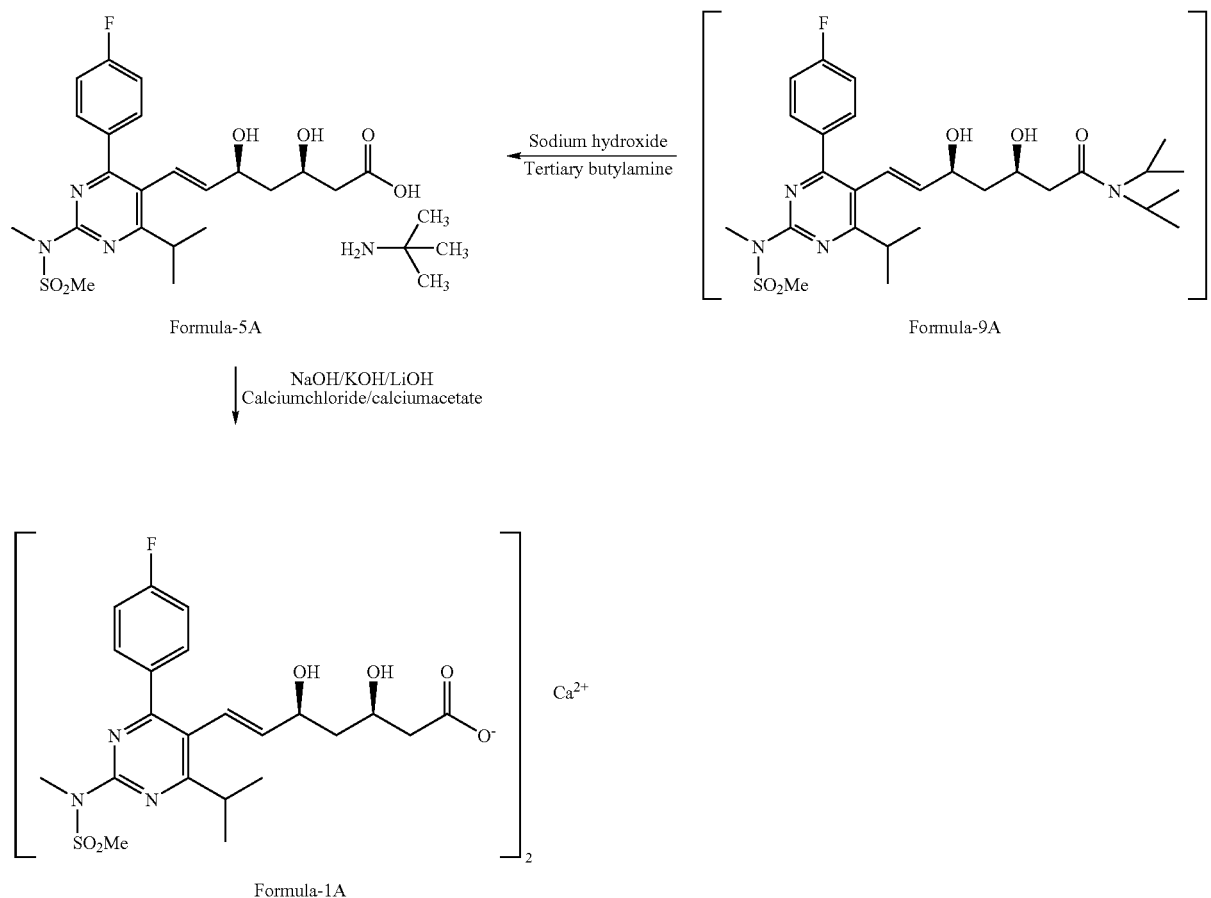
Scheme-15:
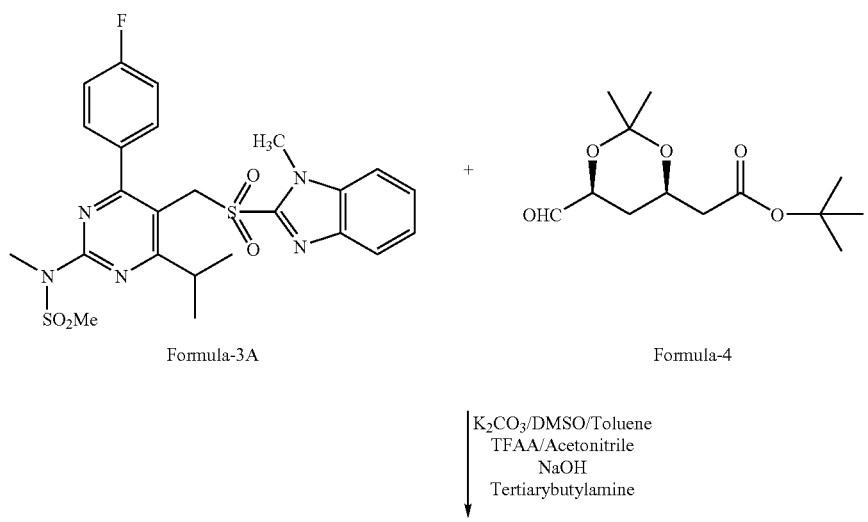

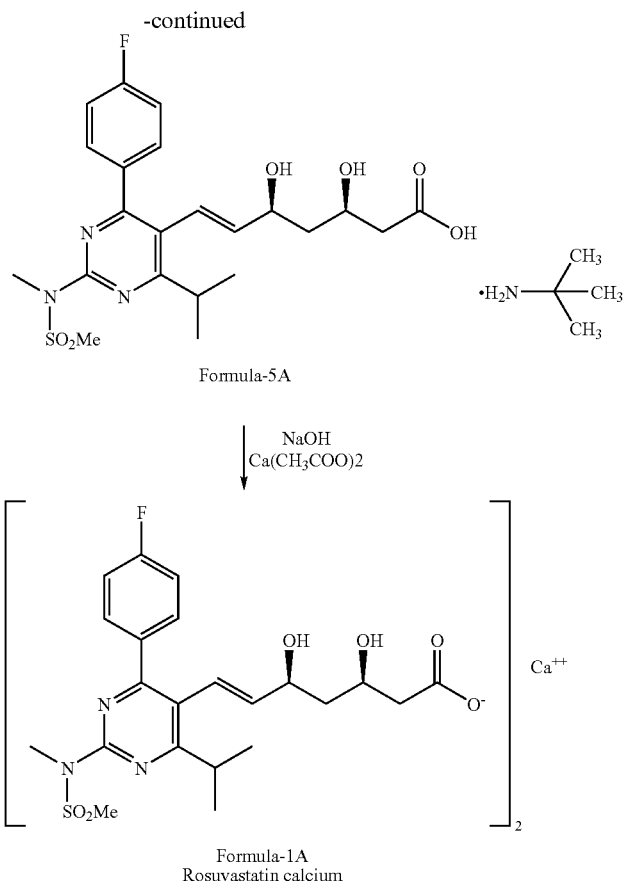
Formula-5A
↓ NaOH
  Ca(CH₃COO)₂
Formula-1A
Rosuvastatin calcium
The process for the preparation of amide compound of formula-7 schematically represented by the following scheme-16:
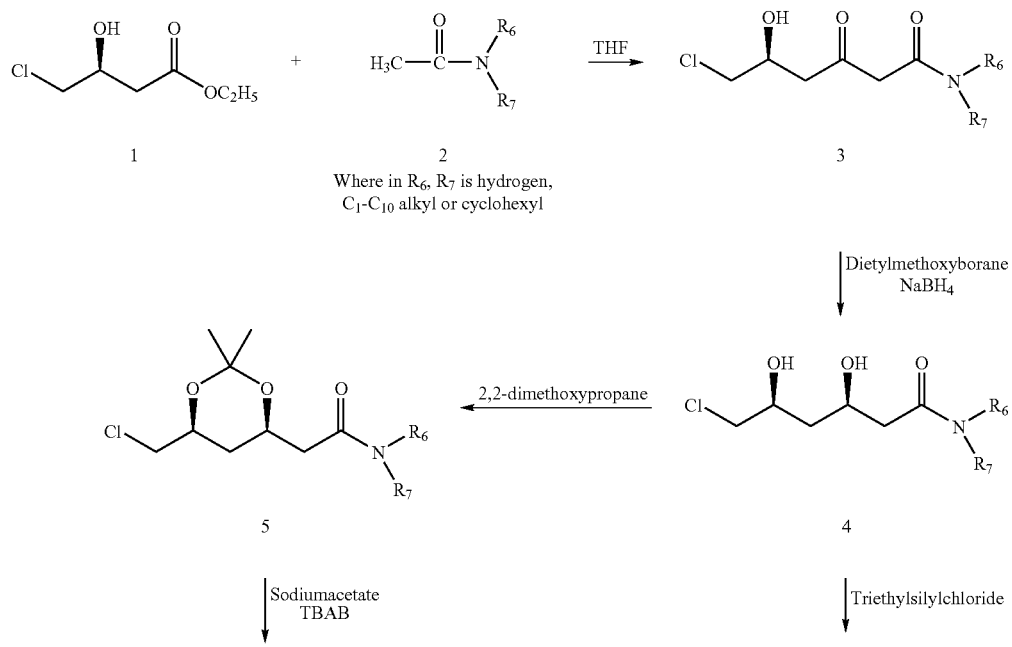
Scheme-16:
Where in $R_6$, $R_7$ is hydrogen, $C_1$-$C_{10}$ alkyl or cyclohexyl

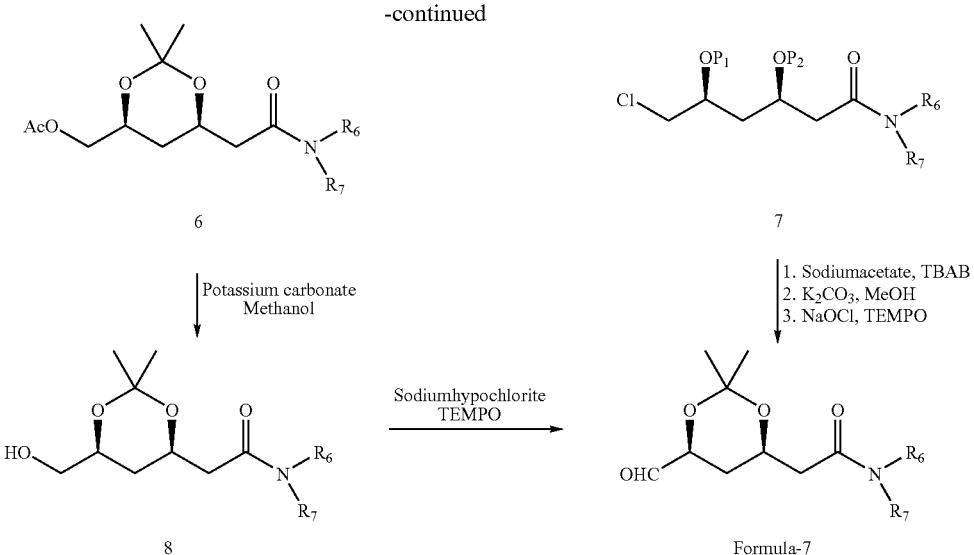

The processes described in the present invention were demonstrated in examples illustrated below. These examples are provided as illustration only and therefore should not be construed as limitation of the scope of the invention.

EXAMPLES

Example-1

Preparation of Sulfide compound of Formula-20a 47.56 grams of 5-(difluoromethoxy)-2-mercapto benzimidazole compound of formula-19a is added to a aqueous sodiumhydroxide solution (9.61 gm sodium hydroxide in 200 ml water) at 25 to 35° C. and stirred for 15 minutes, then added a solution of 400 ml of acetone and 100 grams of [4-(4-Fluoro phenyl)-6-isopropyl-2-(N-Methyl-N-methane sulphonyl amino pyrimidine-5-yl]methyl bromide compound of formula-18a and stirred for 2 hours at 25 to 30° C. Quenched the reaction mass with chilled water and filtered the obtained precipitate and dried the compound at 60-65° C. for 3 hours to get the title compound.

Yield: 119.5 grams; M.R: 165-170° C.

Example-2

Preparation of N-methylated Sulfide Compound of Formula-27a

A solution of 10 grams of sulfide compound of formula-20a prepared as per the example 1 and 100 ml of acetone is cooled to 0-5° C. under nitrogen atmosphere. Added 2.9 grams of potassium carbonate to the above solution then added 3.0 ml of dimethylsulfate to the above reaction mixture and stirred for 4 hours at 0-5° C. Quenched the reaction mixture with chilled water and filtered the precipitated compound. Dried the compound at 50-55° C. for 3 hours.

Yield: 8 grams; M.R: 158-165° C.

Mass spectrum: M+1 peak at 566

Example-3

Preparation of Sulfone Compound of Formula-13a

A solution of 24 grams of N-methylated sulfide compound of formula-27a prepared as per the example 2, 120 ml of methylene chloride and 1.0 grams of tetrabutyl ammonium bromide, is cooled to 0-5° C. Added a mixture of 72 ml of 30% hydrogen peroxide and 1.0 grams of ammonium heptamolybdate tetrahydrate. Stirred the mixture for 3 hours. Quenched the reaction mixture with chilled water and separated the organic layer and extracted the reaction mixture with methylene chloride twice. Washed the organic phase with 10% sodium sulfite solution and 5% sodium bicarbonate solution followed by washed with water. Separated the organic phase and distilled the solvent at below 60° C. under reduced pressure. The title compound is isolated using hexanes as a solvent. Dried the compound at 40-45° C. for 6 hours.

Yield: 24 grams. M.R: 145-154° C.

Example-4

Preparation of Sulfone Compound of formula-28a

A solution of 117 grams of sulfide compound of formula-20a prepared as per the example 1 and 585 ml of methylene chloride, is cooled to 0-5° C. Added a mixture of 240.6 ml of 30% hydrogen peroxide and 2.34 grams of ammonium heptamolybdate tetra hydrate. Stirred the mixture for 5 hours. Quenched the reaction mixture with chilled water and separated the organic layer and extracted the reaction mixture with methylene chloride twice. Washed the organic phase with 10% sodium sulfite solution and 5% sodium bicarbonate solution followed by washed with water. Separated the organic phase and distilled the solvent at below 60° C. under reduced pressure. The title compound is isolated using hexanes and heptane mix as a solvent medium. Dried the compound at 60-65° C. for 3 hours.

Yield: 122 grams. M.R: 105-135° C.

Example-5

Preparation of sulfone compound of Formula-13a

A solution of 120 grams of sulfone compound of formula-28a prepared as per the example 4 and 600 ml of acetone at 30-35° C. Added 31.24 grams of potassium carbonate to the above solution then added 21.39 ml of dimethylsulfate to the above reaction mixture and stirred for 4 hours at 30-35° C. Quenched the reaction mixture with chilled water and filtered the precipitated compound. Dried the compound at 50-55° C. for 6 hours.

Yield: 110 grams. M.R: 145-155° C.

Example-6

Preparation of Sulfoxide Compound of Formula-17a

A solution of 24 grams of N-methylated sulfide compound of formula-27a prepared as per the example 2 and 240 ml of methylene chloride is cooled to 0-5° C. Added a mixture of 36 ml of hydrogen peroxide and 1.0 grams of ammonium heptamolybdate tetrahydrate. Stirred the mixture for 3 hours. Quenched the reaction mixture with chilled water and separated the organic layer and extracted the reaction mixture with methylene chloride twice. Washed the organic phase with 10% sodium sulfite solution and 5% sodium bicarbonate solution followed by washed with water. Separated the organic phase and distilled the solvent at below 60° C. under reduced pressure. The title compound is isolated using hexanes as a solvent. Dried the compound at 40-45° C. for 6 hours.

Yield: 24 grams.
Mass spectrum: M+1 peak at 582.

Example-7

Preparation of Olefin Compound of Formula-15a 34.67 grams of potassium carbonate is added to a solution of 25 grams of sulfone compound of Formula-13a prepared as per example 3 and 125 ml of dimethyl sulfoxide at 25 to 35° C. Added 10.8 grams of Tertiary butyl 2-[(4R,6S)-6-formyl-2,2-dimethyl-1,3-dioxane-4-yl]acetate compound of formula-14a. Stirred for 13 hours at 60 to 65° C. Quenched the reaction mixture with chilled water slowly in 30 minutes. Extracted the reaction mixture twice with ethyl acetate. Separated and washed the organic phase with saturated sodium chloride solution. Distilled the solvent completely under reduced pressure at below 70° C. hexanes added to the residue and decanted twice then dissolved the residue in toluene and isolated the title compound using hexanes as a solvent. Dried the compound at 40-45° C. for 6 hours.

Yield: 13.5 grams. M.R: 148-155° C.

Example-8

Preparation of TBA Salt of Dihydroxy acid Compound of Formula-16a

A solution of 25 grams of olefin compound of formula 15a prepared as per example 7 and 250 ml of acetonitrile, is cooled to 23 to 28° C. Added 70.75 ml of 1.0% hydrochloric acid solution slowly to the above contents of the reaction. Stirred the reaction mixture for 4 hours at 23 to 28° C. Added 37.5 ml of 10% sodium hydroxide solution to the reaction mixture and stirred to 2 hours at 30-35° C. Adjust the pH of the reaction mixture to 3.5 to 4.5 with 10% hydrochloride. Separated the organic phase and cooled to 0-10° C. Added 8.66 grams of tertiarybutyl amine (TBA) to the contents and stirred for 1 hour at 0-5° C. Distilled the solvent completely and isolated the title compound using acetonitrile as a solvent. Dried the compound at 40-45° C. for 5 hours.

Yield: 18 grams.

Example-9

Preparation of Calcium Salt of Olefin Dihydroxy Compound of Formula-2a

A solution of 15 grams of TBA salt compound of formula-16a and 75 ml of water, is cooled to 25-30° C. Added 8.5 ml of 10% sodium hydroxide solution. Stirred for 1 hour. Adjusted the pH of the reaction mixture to 9.1 by extracting the reaction mixture thrice with tertiary butyl acetate. Added the aqueous phase of the reaction mixture to a solution of 2.55 grams of calcium chloride and 15 ml of water at 35 to 45° C. Filtered off the precipitated compound. Dried the compound at 40-45° C.

Yield: 12 grams; M.R: 145-150 (Decomposed);
Purity by HPLC is 99.50%

Example-10

Preparation of Sulfide Compound of Formula-20b 39.68 grams of 5-methoxy-2-mercapto benzimidazole compound of formula-19b is added to aqueous sodium hydroxide solution (9.61 gm sodium hydroxide in 200 ml water) at 25 to 35° C. and stirred for 15 minutes, then added a solution of 400 ml of acetone and 100 grams of [4-(4-Fluoro phenyl)-6-isopropyl-2-(N-Methyl-N-methane Sulphonyl amino pyrimidine-5yl]methyl bromide compound of formula-18a and stirred for 2 hours at 25 to 30° C. Quenched the reaction mass with chilled water filtered the obtained precipitate and dried the compound at 60-65° C. for 3 hours to get the title compound.

Yield: 110 grams. M.R: 159-163° C.

Example-11

Preparation of Sulfide Compound of Formula-20c 33.07 grams of 2-mercapto benzimidazole compound of formula-19c is added to an aqueous sodium hydroxide solution (9.61 gm of sodium hydroxide in 200 ml water) at 25 to 35° C. and stirred for 15 minutes, then added a solution of 400 ml of acetone and 100 grams of [4-(4-Fluoro phenyl)-6-isopropyl-2-(N-Methyl-N-methane Sulphonyl amino pyrimidine-5-yl]methyl bromide compound of formula-18a and stirred for 1.5 hours at 25 to 30° C. Quenched the reaction mass with chilled water filtered the obtained precipitate and dried the compound at 60-65° C. for 2 hours to get the title compound.

Yield: 106.0 grams. M.R: 188-195° C.

Example-12

Preparation of Sulfone Compound of Formula-28a

A solution of 108 grams of sulfide compound of formula-20b prepared as per the example 10, 540 ml of methylene chloride and 2.16 gr tetra butyl ammonium bromide. Added a mixture of 237.5 ml of 30% hydrogen peroxide and 2.16 grams of ammonium heptamolybdate tetrahydrate. Stirred the mixture for 4 hours. Quenched the reaction mixture with chilled water and separated the organic layer and extracted the reaction mixture with methylene chloride twice. Washed the organic phase with 10% sodium sulfite solution and 5% sodium bicarbonate solution followed by washed with water. Separated the organic phase and distilled the solvent at below 60° C. under reduced pressure. The title compound is isolated using hexanes as a solvent. Dried the compound at 60-65° C. for 3 hours.

Yield: 114 grams. M.R: 100-132° C.

Example-13

Preparation of Sulfone Compound of Formula-28b

A solution of 105 grams of sulfide compound of formula-20c prepared as per the example 11, 525 ml of methylene chloride and 2.1 grams tetrabutyl ammonium bromide. Added a mixture of 245.2 ml of 30% hydrogen peroxide and 2.1 grams of ammonium heptamolybdate tetrahydrate. Stirred the mixture for 3 hours. Quenched the reaction mixture with chilled water and separated the organic layer and extracted the reaction mixture with methylene chloride twice. Washed the organic phase with 10% sodium sulfite solution and 5% sodium bicarbonate solution followed by washed with water. Separated the organic phase and distilled the solvent at below 60° C. under reduced pressure. The title compound is isolated using hexanes as a solvent. Dried the compound at 60-65° C. for 4 hours.

Yield: 107 grams. M.R: 98-128° C.

Example-14

Preparation of N-methylated Sulfone Compound of Formula-13b

A solution of 3.0 grams of sulfone compound of formula-28a prepared as per the example 12 and 15 ml of acetone, is cooled to 0-5° C. under nitrogen atmosphere. Added 0.88 grams of potassium carbonate to the above solution then added 0.6 ml of dimethylsulfate to the above reaction mixture and stirred for 4 hours at 0-5° C. Quenched the reaction mixture with chilled water and filtered the precipitated compound. Dried the compound at 50-55° C. for 6 hours.

Yield: 1.7 grams. M.R: 122-130° C.

Example-15

Preparation of N-methylated Sulfone Compound of Formula-13c

A solution of 3.0 grams of sulfone compound of formula-28b prepared as per the example 13 and 15 ml of acetone, is cooled to 0-5° C. under nitrogen atmosphere. Added 0.93 grams of potassium carbonate to the above solution then added 0.63 ml of dimethylsulfate to the above reaction mixture and stirred for 4 hours at 0-5° C. Quenched the reaction mixture with chilled water and filtered the precipitated compound. Dried the compound at 50-55° C. for 6 hours.

Yield: 2.0 grams. M.R: 126-134° C.

Example-16

Preparation of Olefin Compound of Formula-15a 8.4 grams of cesium carbonate is added to a solution of 10 grams of sulfone compound of formula-13b prepared as per example 14 and 50 ml of dimethyl sulfoxide at 25 to 35° C. Added 4.5 grams of Tertiary butyl 2-[(4R,6S)-6-formyl-2,2-dimethyl-1,3-dioxane-4-yl]acetate compound of formula-14a. Stirred for 3 hours at 25 to 35° C. Quenched the reaction mixture with chilled water slowly in 30 minutes. Extracted the reaction mixture twice with ethyl acetate. Separated and washed the organic phase with saturated sodium chloride solution. Distilled the solvent completely under reduced pressure at below 70° C. hexanes added to the residue and decanted twice then dissolved the residue in toluene and isolated the title compound using hexanes as a solvent. Dried the compound at 40-45° C. for 6 hours.

Yield: 6.0 grams. M.R: 148-155° C. Purity by HPLC>96%

Example-17

Preparation of Olefin Compound of Formula-15a 8.4 grams of cesium carbonate is added to a solution of 10 grams of sulfone compound of Formula-13c prepared as per example 15 and 50 ml of dimethyl sulfoxide at 25 to 35° C. Added 4.5 grams of Tertiary butyl 2-[(4R,6S)-6-formyl-2,2-dimethyl-1,3-dioxane-4-yl]acetate compound of formula-14a. Stirred for 3 hours at 25 to 35° C. Quenched the reaction mixture with chilled water slowly in 30 minutes. Extracted the reaction mixture twice with ethyl acetate. Separated and washed the organic phase with saturated sodium chloride solution. Distilled the solvent completely under reduced pressure at below 70° C. hexanes added to the residue and decanted twice then dissolved the residue in toluene and isolated the title compound using hexanes as a solvent. Dried the compound at 40-45° C. for 6 hours.

Yield: 6.2 grams. M.R: 148-155° C.
Purity by HPLC>96%

Example-18

Preparation of Calcium Salt of Olefin Dihydroxy Compound of Formula-2a

A solution of 15 grams of TBA salt compound of formula-16a and 75 ml of water, is cooled to 25-30° C. Added 8.5 ml of 10% sodium hydroxide solution. Stirred for 1 hour. Adjusted the pH of the reaction mixture to 9.1 by extracting the reaction mixture thrice with tertiary butyl acetate. Added the aqueous phase of the reaction mixture to a solution of 4.3 grams of calcium acetate and 15 ml of water at 35 to 45° C. Filtered off the precipitated compound. Dried the compound at 40-45° C.

Yield: 12 grams; M.R: 145-150 (Decomposed);
Purity by HPLC is 99.50%

Example-19

Preparation of Calcium Salt of Olefin Dihydroxy Compound of Formula-2a

A solution of 12.5 grams of methyl amine salt compound of formula-16b and 65 ml of water, is cooled to 25-30° C. Added 9.5 ml of 10% sodium hydroxide solution. Stirred for 1 hour. Adjusted the pH of the reaction mixture to 9.1 by expelling the methyl amine traces. Extracted the reaction mixture thrice with tertiary butyl acetate. Added the aqueous phase of the reaction mixture to a solution of 2.79 grams of calcium acetate and 12.5 ml of water at 35 to 45° C. Filtered off the precipitated compound. Dried the compound at 40-45° C.

Yield: 9.5 grams
M.C: 4.0%

Example-20

Preparation of Calcium Salt of Olefin Dihydroxy Compound of Formula-2a

A solution of 10 grams of methyl amine salt compound of formula-16b and 50 ml of water, is cooled to 25-30° C. Added 7.8 ml of 10% sodium hydroxide solution. Stirred for 1 hour. Adjusted the pH of the reaction mixture to 9.1 by expelling the methyl amine traces. Extracted the reaction mixture thrice with tertiary butyl acetate. Added the aqueous phase of the reaction mixture to a solution of 1.701 grams of calcium chloride and 10 ml of water at 35 to 45° C. Filtered off the precipitated compound. Dried the compound at 40-45° C.
Yield: 8.7 grams.
HPLC Purity is 99%
Particle Size: D (v, 0.1) is 4.72 μm; D (v, 0.5) is 40.76 μm; D (v, 0.9) is 168.32 μm.

Example-21

Preparation of Sulfide Compound of Formula-20d

15 grams of 5-(difluoromethoxy)-2-mercapto benzimidazole compound of formula-19a is added to a 82.5 ml of 2.9% solution of sodium hydroxide at 25 to 35° C. and stirred for 15 minutes, then added a mixture of 175 ml of dimethylformamide and 25 gr of 3-(bromomethyl)-2-cyclopropyl-4-(4-fluorophenyl)quinoline compound of Formula-18b and stirred for 2 hours at 25 to 30° C. Quenched the reaction mass with chilled water filtered the obtained precipitate and dried the compound at 50-55° C. for 6 hours to get the title compound.
Yield: 32 grams. M.R: 117-125° C.

Example-22

Preparation of Sulfone Compound of Formula-28c

A solution of 25 grams of sulfide compound of formula-20d, 100 ml of methylene chloride and 1.0 grams of tetrabutyl ammonium bromide, is cooled to 0-5° C. Added a mixture of 56 ml of 30% hydrogen peroxide and 1.0 grams of ammonium heptamolybdate tetrahydrate. Stirred the mixture for 3 hours. Quenched the reaction mixture with chilled water and separated the organic layer and extracted the reaction mixture with methylene chloride twice. Washed the organic phase with 10% sodium sulfite solution and 5% sodium bicarbonate solution followed by washed with water. Separated the organic phase and distilled the solvent at below 60° C. under reduced pressure. The title compound is isolated using hexanes as a solvent. Dried the compound at 40-45° C. for 6 hours.
Yield: 23 grams. M.R: 150-160° C.

Example-23

Preparation of N-methylated Sulfone Compound of Formula-13d

A solution of 3.0 grams of sulfone compound of formula-28c prepared as per the example 22 and 15 ml of acetone, is cooled to 0-5° C. under nitrogen atmosphere. Added 0.93 grams of potassium carbonate to the above solution then added 0.63 ml of dimethylsulfate to the above reaction mixture and stirred for 4 hours at 0-5° C. Quenched the reaction mixture with chilled water and filtered the precipitated compound. Dried the compound at 50-55° C. for 6 hours.
Yield: 3.5 grams. M.R: 158-162° C.

Example-24

Preparation of Olefin Compound of Formula-15b

5.2 grams of cesium carbonate is added to a solution of 3.5 grams of sulfone compound of Formula-13d and 20 ml of dimethyl sulfoxide at 25 to 35° C. Added 1.68 grams of Tertiary butyl 2-[(4R,6S)-6-formyl-2,2-dimethyl-1,3-dioxane-4-yl]acetate compound of Formula-14a. Stirred for 3 hours at 25 to 35° C. Quenched the reaction mixture with chilled water slowly in 30 minutes. Extracted the reaction mixture twice with ethyl acetate. Separated and washed the organic phase with saturated sodium chloride solution. Distilled the solvent completely under reduced pressure at below 70° C. hexanes added to the residue and decanted twice then dissolved the residue in toluene and isolated the title compound using hexanes as a solvent. Dried the compound at 40-45° C. for 6 hours.
Yield: 1.2 grams. M.R: 115-121° C.

Example-25

Preparation of Sulfide Compound of Formula-20e

6.0 grams of 5-(difluoromethoxy)-2-mercapto benzimidazole compound of formula-19c is added to a 36 ml of 2.9% solution of sodium hydroxide at 25 to 35° C. and stirred for 15 minutes, then added a mixture of 30 ml of acetone and 10 grams of 2-(bromomethyl)-3-(4-fluorophenyl)-1-isopropyl-1H-indole compound of formula-18c and stirred for 2 hours at 25 to 30° C. Quenched the reaction mass with chilled water filtered the obtained precipitate and dried the compound at 50-55° C. for 6 hours to get the title compound.
Yield: 10 grams.

Example-26

Preparation of Sulfone Compound of Formula-28d

A solution of 10 grams of sulfide compound of formula-20e, 100 ml of methylene chloride and 0.5 grams of tetrabutyl ammonium bromide, is cooled to 0-5° C. Added a mixture of 14 ml of 30% hydrogen peroxide and 1 gram of ammonium heptamolybdate tetrahydrate. Stirred the mixture for 3 hours. Quenched the reaction mixture with chilled water and separated the organic layer and extracted the reaction mixture with methylene chloride twice. Washed the organic phase with 10% sodium sulfite solution and 5% sodium bicarbonate solution followed by washed with water. Separated the organic phase and distilled the solvent at below 60° C. under reduced pressure. The title compound is isolated using hexanes as a solvent. Dried the compound at 40-45° C. for 6 hours.
Yield: 6.0 grams.

Example-27

Preparation of N-methylated Sulfone Compound of Formula-13e

A solution of 5 grams of sulfone compound of formula-28d prepared as per the example 26 and 25 ml of acetone, is cooled to 0-5° C. under nitrogen atmosphere. Added 1.35 grams of potassium carbonate to the above solution then added 3.1 ml of dimethylsulfate to the above reaction mixture and stirred for 4 hours at 0-5° C. Quenched the reaction mixture with chilled water and filtered the precipitated compound. Dried the compound at 50-55° C. for 6 hours.

Yield: 3.0 grams.

Example-28

Preparation of Olefin Compound of Formula-15c 2.7 grams of potassium carbonate is added to a solution of 3.0 grams of sulfone compound of Formula-13e prepared as per example 27 and 10 ml of dimethyl sulfoxide at 25 to 35° C. Added 1.5 grams of Tertiary butyl 2-[(4R,6S)-6-formyl-2,2-dimethyl-1,3-dioxane-4-yl]acetate compound of Formula-14a. Stirred for 3 hours at 25 to 35° C. Quenched the reaction mixture with chilled water slowly in 30 minutes. Extracted the reaction mixture twice with ethyl acetate. Separated and washed the organic phase with saturated sodium chloride solution. Distilled the solvent completely under reduced pressure at below 70° C. hexanes added to the residue and decanted twice then dissolved the residue in toluene and isolated the title compound using hexanes as a solvent. Dried the compound at 40-45° C. for 6 hours.

Yield: 0.6 grams

Example-29

Preparation Tertiarybutyl Amine Salt of Rosuvastatin Compound of Formula-5A

A mixture of 23.1 Kgs. compound of formula-3A and 90 liters of dimethylsulfoxide and 48 Kgs. of potassium carbonate is heated to 70-75° C. Added a solution of 15 Kgs. of aldehyde compound of formula-4 in 90 liters of dimethylsulfoxide lot wise to the above reaction mixture. Stirred the reaction mixture for 4 hours at 70-75° C. Added 225 liters of toluene to the above reaction mixture. Stirred the reaction mixture for 45 minutes at 25-30° C. Filtered the byproduct and washed the byproduct with toluene. Added 240 liters of water followed by aqueous sodium chloride solution to the above reaction mixture. Stirred the reaction mixture for 15 minutes. Separated the organic and aqueous layer. Extracted the aqueous layer with toluene. Washed the total organic layer with water. Purified the organic layer with silica gel. Distilled the solvent completely under reduced pressure at below 70° C. Cooled the reaction mixture to 25-30° C. Dissolved the residue in 90 liters of acetonitrile and stirred the reaction mixture for 15 minutes at 25-30° C. Adjusted the pH of the reaction mixture to 1.4 with aqueous hydrochloric acid solution at 23-28° C. Stirred the reaction mixture for 4 hours at 23-28° C. Heated the reaction mixture to 30-35° C. Added sodium hydroxide solution (1.5 Kgs. in 60 liters of water) to the above reaction mixture at 30-35° C. Stirred the reaction mixture for 1.5 hours at 30-35° C. Distilled the solvent completely under reduced pressure at below 60° C. Cooled the reaction mixture to 25-30° C. Diluted the above reaction mixture with water. Washed the reaction mixture with tertiary butyl acetate. Added 90 liters of acetonitrile and 30 Kgs. of sodium chloride to the reaction mixture. Cooled the reaction mixture to 0-5° C. Adjusted the pH of the reaction mixture to 4.3 with 10% hydrochloric acid solution. Stirred the reaction mixture for 15 minutes. Separated the organic and aqueous layer. Cooled the organic layer to 0-10° C. Added 3.9 liters of tertiarybutyl amine to the above reaction mixture at 0-10° C. Raised the temperature to 25-35° C. Stirred the reaction mixture for 60 minutes. Distilled the solvent completely under reduced pressure at below 50° C. Added 30 liters of acetonitrile to the above crude then distilled the solvent completely under reduced pressure at below 50° C. Added 90 liters of acetonitrile to the above reaction mixture and cooled to 25-35° C. Stirred the reaction mixture for 1.5 hours at 25-35° C. Cooled the reaction mixture to 0-10° C. and stirred for 60 minutes. Filtered the precipitated solid and washed with acetonitrile. Added 90 liters of acetonitrile and 10.5 liters of isopropyl alcohol to the above obtained solid. Heated the reaction mixture slowly to reflux temperature of 70-75° C. Stirred the reaction mixture for 30 minutes at reflux. Cooled the reaction mixture to 25-30° C. in 1.5 hours. Stirred the reaction mixture for 30 minutes at 25-30° C. Filtered the precipitated solid and washed with acetonitrile. Dried the solid at 40-45° C. for 4 hours to get the title compound.

Yield: 11.8 Kgs.

Example-30

Preparation of Rosuvastatin Calcium Compound of Formula-1A

A solution of 12.5 Kgs of rosuvastatin tertiarybutyl amine compound of Formula-5A and 63 liters of water is cooled to 25-30° C. Added aqueous sodium hydroxide solution (0.9 Kgs. in 11 liters of water) to the reaction mixture. Stirred the reaction mixture for 1 hour. Adjusted the pH of the reaction mixture to 9.1 by extracting the reaction mixture thrice with tertiary butyl acetate. Added the aqueous phase of the reaction mixture to a solution of 2.1 Kgs. of calcium acetate in 12.5 liters of water at 35 to 45° C. Filtered the precipitated compound. Dried the compound at 40-45° C.

Yield: 10.6 Kgs.

M.C: 3.1%

Example-31

Preparation Tertiarybutyl Amine Salt of Rosuvastatin compound of Formula-5A

A mixture of 23.1 Kgs. compound of formula-3A and 90 liters of dimethylsulfoxide and 48 Kgs. of potassium carbonate is heated to 70-75° C. Added a solution of 15 Kgs. of aldehyde compound of formula-4 in 90 liters of dimethylsulfoxide lot wise to the above reaction mixture. Stirred the reaction mixture for 4 hours at 70-75° C. Added 225 liters of toluene to the above reaction mixture. Stirred the reaction mixture for 45 minutes at 25-30° C. Filtered the byproduct and washed the byproduct with toluene. Added 240 liters of water followed by aqueous sodium chloride solution to the above reaction mixture. Stirred the reaction mixture for 15 minutes. Separated the organic and aqueous layer. Extracted the aqueous layer with toluene. Washed the total organic layer with water. Distilled the solvent completely under reduced pressure at below 70° C. Cooled the reaction mixture to 25-30° C. Dissolved the residue in 90 liters of acetonitrile and stirred the reaction mixture for 15 minutes at 25-30° C. Adjusted the pH of the reaction mixture to 1.4 with aqueous hydrochloric acid solution at 23-28° C. Stirred the reaction mixture for 4 hours at 23-28° C. Heated the reaction mixture to 30-35° C. Added sodium hydroxide solution (1.5 Kgs. in 60 liters of water) to the above reaction mixture at 30-35° C. Stirred the reaction mixture for 1.5 hours at 30-35° C. Distilled the solvent completely under reduced pressure at below 60° C. Cooled the reaction mixture to 25-30° C. Diluted the above reaction mixture with water. Washed the reaction mixture with tertiary butyl acetate. Added 90 liters of acetonitrile and 30 Kgs. of sodium chloride to the reaction mixture.

Cooled the reaction mixture to 0-5° C. Adjusted the pH of the reaction mixture to 4.3 with 10% hydrochloric acid solution. Stirred the reaction mixture for 15 minutes. Separated the organic and aqueous layer. Cooled the organic layer to 0-10° C. Added 3.9 liters of tertiarybutyl amine to the above reaction mixture at 0-10° C. Raised the temperature to 25-35° C. Stirred the reaction mixture for 60 minutes. Distilled the solvent completely under reduced pressure at below 50° C. Added 30 liters of acetonitrile to the above crude then distilled the solvent completely under reduced pressure at below 50° C. Added 90 liters of acetonitrile to the above reaction mixture and cooled to 25-35° C. Stirred the reaction mixture for 1.5 hours at 25-35° C. Cooled the reaction mixture to 0-10° C. and stirred for 60 minutes. Filtered the precipitated solid and washed with acetonitrile. Added 90 liters of acetonitrile and 10.5 liters of isopropyl alcohol to the above obtained solid. Heated the reaction mixture slowly to reflux temperature of 70-75° C. Stirred the reaction mixture for 30 minutes at reflux. Cooled the reaction mixture to 25-30° C. in 1.5 hours. Stirred the reaction mixture for 30 minutes at 25-30° C. Filtered the precipitated solid and washed with acetonitrile. Dried the solid at 40-45° C. for 4 hours to get the title compound.

Yield: 12 Kgs.

Example-32

Preparation of Rosuvastatin Calcium Salt Compound of Formula-1A

An aqueous solution of lithium hydroxide (0.81 grams in 10 ml of water) was added to a solution of 10 grams of rosuvastatin tertiarybutyl amine in 50 ml of water at 25-35° C. Stirred the reaction mixture for 60 minutes at 25-35° C. Adjusted the pH of the reaction mixture to 9.1 by distillation at below 40° C. Added 10 ml of water to the above reaction mixture. Filtered the reaction mixture through filter paper and washed with water. Added aqueous solution of the reaction mixture to a solution of 1.82 grams of calcium acetate in 15 ml of water at 25-35° C. Stirred the reaction mixture for 45 minutes at 25-35° C. Filtered the solid and washed with water. Dried the solid at 50-60° C. to get the title compound.

Yield: 7 grams

Example-33

Preparation of Rosuvastatin Calcium Salt Compound of Formula-1A

An aqueous solution of potassium hydroxide (1.09 grams in 10 ml of water) was added to a solution of 10 grams of rosuvastatin tertiarybutyl amine in 50 ml of water at 25-35° C. Stirred the reaction mixture for 60 minutes at 25-35° C. Adjusted the pH of the reaction mixture to 9.1 by distillation at below 40° C. Added 10 ml of water to the above reaction mixture. Filtered the reaction mixture through filter paper and washed with water. Added aqueous solution of the reaction mixture to a solution of 1.82 grams of calcium acetate in 15 ml of water at 25-35° C. Stirred the reaction mixture for 45 minutes at 25-35° C. Filtered the solid and washed with water. Dried the solid at 50-60° C. to get the title compound.

Yield: 7 grams

Example-34

Preparation of Diisopropyl Amide Compound of Rosuvastatin of Formula-10A

A mixture of 0.77 grams of compound of Formula-3A, 10 ml of dimethylsulfoxide and 1.6 grams of potassium carbonate is heated to 70-75° C. Added a solution of aldehyde compound of Formula-4 in 10 ml of dimethylsulfoxide to the above reaction mixture. Stirred the reaction mixture for 8 hours at 70-75° C. Added 25 ml of toluene to the above reaction mixture at 25-30° C. Filtered the byproduct and washed with toluene. Added 80 ml of water to the filtrate. Added 10 ml saturated sodium chloride solution to the above mixture. Stirred the reaction mixture for 10 minutes. Separated the organic and aqueous layer. Extracted the aqueous layer with toluene. Washed the total organic layer with water. Added 100 gram of silica gel to the above organic layer. Stirred the reaction mixture 20 minutes at 25-35° C. Filtered the silica gel and washed with toluene. Added 100 gram of silica gel to the filtrate and stirred for 20 minutes at 25-35° C. Filtered off the silica gel and washed with toluene. Distilled the solvent completely under reduced pressure at below 70° C. Dissolved the residue in 30 ml of acetonitrile. Added 5.0 ml of trifluoroacetic acid slowly to the above reaction mixture at 0-10° C. Stirred the reaction mixture for 20 hours at 0-10° C. Raised the temperature of the reaction mixture to 30-35° C. Concentrated the reaction mixture. Added 6.0 grams of diisopropyl amine to the reaction mass. Heated the reaction mixture to reflux. Stirred the reaction mixture for 12 hours at reflux temperature. Concentrated the reaction mixture to get the title compound as residue.

Example-35

Preparation Tertiarybutyl Amine Salt of Rosuvastatin Compound of Formula-5A

Added aqueous sodium hydroxide solution to a mixture of 60 gram of diisopropyl compound of formula-10A in 250 ml of acetonitrile. Stirred the reaction mixture for 1.5 hours at 30-35° C. Distilled the solvent completely under reduced pressure at below 60° C. Added 200 ml of D.M water to the above reaction mixture and stirred for 15 minutes. Washed the above reaction mixture with tertiary butyl acetate. Added 300 ml of acetonitrile and 100 grams of sodium chloride to the reaction mixture at 25-30° C. Cooled the reaction mixture to 1-10° C. Adjusted the pH of the reaction mixture to 4.3 with aqueous hydrochloric acid. Stirred the reaction mixture for 10 minutes. Separated the organic and aqueous layer. Cooled the organic layer to 0-10° C. Added 13 ml of tertiary butyl acetate to the above reaction mixture at 0-10° C. Raised the temperature to 25-35° C. Stirred the reaction mixture for 60 minutes at 25-35° C. Distilled the solvent completely under reduced pressure at below 50° C. Added 300 ml of acetonitrile at below 50° C. Distilled the solvent completely under reduced pressure. Added 100 ml of acetonitrile to the above residue. Stirred the reaction mixture for 1.5 hours at 25-35° C. Cooled the reaction mixture to 0-10° C. Stirred the reaction mixture for 60 minutes at 0-10° C. Filtered the solid and washed the solid with acetonitrile. Added a mixture of 300 ml of acetonitrile and 35 ml isopropyl alcohol to the above obtained wet solid. Heated the reaction mixture to 70-75° C. Stirred the reaction mixture for 30 minutes at 70-75° C. Cooled the reaction mixture to 25-30° C. in 1.5 hours. Stirred the reaction mixture for 30 minutes at 25-30° C. Filtered the solid and washed the solid with acetonitrile. Dried the solid to get the title compound.

Yield: 40 grams

Example-36

Preparation of Tertiarybutyl Amine Salt of Rosuvastatin Compound of Formula-5A

Added 35 grams of potassium carbonate to a solution of 25 grams of sulfone compound of Formula-3A, 25 ml of dimethyl sulfoxide at 25 to 35° C. Added 11 grams of 2-((4R,6S)-6-formyl-2,2-dimethyl-1,3-dioxan-4-yl)-N,N-diisopropylacetamide compound of formula-7A to the above reaction mixture. Stirred the reaction mixture for 13 hours at 60 to 65° C. Quenched the reaction mixture with chilled water slowly in 30 minutes. Extracted the reaction mixture twice with ethyl acetate. Separated and washed the organic phase with saturated sodium chloride solution. Distilled the solvent completely under reduced pressure at below 70° C. Dissolved the residue in 135 ml of acetonitrile, is cooled to 23 to 28° C. Added 38.2 ml of 1.0% hydrochloric acid solution slowly to the above contents of the reaction. Stirred the reaction mixture for 4 hours at 23 to 28° C. Added 21 ml of 10% sodium hydroxide solution to the reaction mixture and stirred to 2 hours at 35-40° C. Adjust the pH of the reaction mixture to 3.5 to 4.5 with 10% hydrochloride. Separated the organic phase and cooled to 0-10° C. Added 4.75 grams of Tertiarybutyl amine to the contents and stirred for 1 hour at 0-5° C. Distilled the solvent completely and isolated the title compound using acetonitrile as a solvent. Dried the compound to get the title compound.

Yield: 43 grams

Example-37

Preparation of Rosuvastatin Calcium Compound of Formula-1A

A solution of 15 grams of Rosuvastatin tertiarybutyl amine salt compound of formula-5A and 75 ml of water is cooled to 25-30° C. Added 8.5 ml of 10% sodium hydroxide solution. Stirred for 1 hour. Adjusted the pH of the reaction mixture to 9.1 by extracting the reaction mixture thrice with tertiary butyl acetate. Added the aqueous phase of the reaction mixture to a solution of 2.55 grams of calcium chloride and 15 ml of water at 35 to 45° C. Filtered off the precipitated compound. Dried the compound at 40-45° C.

Yield: 12 grams
M.C: 3.5%

Example-38

Preparation of Tertiarybutyl Amine Salt of Rosuvastatin Compound of Formula-5A

A mixture of 77 grams of sulfone compound of formula-3A, 300 ml of dimethyl sulfoxide and 160 grams of potassium carbonate is heated to 70-75° C. Added a solution of 50 grams of aldehyde compound of formula-4 in 300 ml of dimethyl sulfoxide. Stirred the reaction mixture for 8 hours at 70-75° C. Added 750 ml of toluene to the above reaction mixture. Stirred the reaction mixture for 45 minutes at 25-30° C. Filtered the byproduct and washed with toluene. Added 800 ml of water to the filtrate followed by 100 ml of saturated sodium chloride solution. Stirred the reaction mixture for 10 minutes. Separated the organic and aqueous layers. Extracted the aqueous layer with toluene. Washed the total organic layer with water. Added 100 grams of silica gel to the organic layer. Stirred the reaction mixture for 20 minutes at 25-35° C. Filtered the silica gel and washed with toluene. Added 100 grams of silica gel to the filtrate. Stirred for 20 minutes at 25-35° C. Filtered the silica gel and washed with toluene. Distilled the solvent completely under reduced pressure at below 70° C. Added 500 ml of acetonitrile to the obtained crude. Added 50 ml of trifluoroacetic acid to the above reaction mixture at 0-10° C. Stirred the reaction mixture for 8 hours at 0-10° C. Raised the temperature to 30-35° C. Added aqueous sodium hydroxide solution (5 grams in 50 ml of water) to the reaction mixture. Stirred the reaction mixture for 1.5 hours at 25-30° C. Distilled the solvent completely under reduced pressure at below 50° C. Added 200 ml of water to the reaction mixture. Washed the reaction mixture with tertiary butyl acetate. Added 500 ml of acetonitrile to the above reaction mixture. Added 100 grams of sodium chloride to the above reaction mixture. Adjusted the pH of the reaction mixture to 4.8 with aqueous hydrochloric acid. Stirred the reaction mixture for 10 minutes. Separated the organic and aqueous layer. Cooled the organic layer to 0-10° C. Added 13 ml of tertiarybutyl amine to the organic layer at 0-10° C. Raised the reaction mixture temperature to 25-35° C. and stirred for 60 minutes. Distilled the solvent completely under reduced pressure at below 50° C. Added 100 ml of acetonitrile to the reaction mixture and distilled the solvent completely under reduced pressure. Added 300 ml of acetonitrile to the reaction mixture. Cooled the reaction mixture to 25-35° C. Stirred the reaction mixture for 1.5 hours at 25-35° C. Cooled the reaction mixture to 0-10° C. and stirred for 60 minutes at 0-10° C. Filtered the solid and washed the solid with acetonitrile. Added 300 ml of acetonitrile and 35 ml of isopropyl alcohol to the wet solid. Heated the reaction mixture to reflux at 70-75° C. Stirred the reaction mixture at reflux for 30 minutes. Cooled the reaction mixture to 25-30° C. in 1.5 hours. Stirred the reaction mixture for 30 minutes at 25-30° C. Filtered the solid and washed with acetonitrile. Dried the solid at 30-35° C. for 2 hours followed by 40-45° C. for another 4 hours to get the title compound.

Yield: 39 grams

Example-39

Preparation of Rosuvastatin Calcium Compound of Formula-1A

Added aqueous solution of sodium hydroxide (9 grams in 110 ml of water) to the solution of 125 grams of rosuvastatin tertiarybutyl amine salt compound of formula-5A in 630 ml of water at 20-30° C. Stirred the reaction mixture for 1.5 hours at 20-30° C. Extracted the reaction mixture twice with tertiary butyl acetate. Adjusted the pH of the reaction mixture to 9.1 by evaporating the aqueous reaction mixture with nitrogen under reduced pressure at below 40° C. Filtered the reaction mixture through micron filter and washed with water. The particle freed reaction mixture added to an aqueous solution of calcium acetate (21.4 grams in 125 ml of water) in 45 minutes at 25-30° C. Stirred the reaction mixture for 45 minutes at 25-30° C. Filtered the solid and washed with water at 25-30° C. Dried the solid at 25-35° C. for 6 hours followed by 40-45° C. for 5 hours to get the title compound.

Yield: 105 grams
Particle Size: D (v, 0.1) is 4.9 µm; D(v, 0.5) is 45.86 µm; D(v, 0.9) is 180.59 µm.
Particle Size after micronization: D (v, 0.1) is 2.46 µm; D(v, 0.5) is 12.85 µm; D(v, 0.9) is 46.43 µm.

Example-40

Preparation of Tertiarybutyl Amine Salt of Pitavastatin Compound of Formula-5C

A mixture of 50 grams of 2-cyclopropyl-4-(4-fluorophenyl)-3-methylquinoline compound of formula-3C, 195 ml of dimethyl sulfoxide and 104 grams of potassium carbonate is heated to 70-75° C. Added a solution of 32 grams of aldehyde compound of formula-4 in 195 ml of dimethyl sulfoxide.

Stirred the reaction mixture for 8 hours at 70-75° C. Added 487 ml of toluene to the above reaction mixture. Stirred the reaction mixture for 45 minutes at 25-30° C. Filtered the byproduct and washed with toluene. Added 520 ml of water to the filtrate followed by 65 ml of saturated sodium chloride solution. Stirred the reaction mixture for 10 minutes. Separated the organic and aqueous layers. Extracted the aqueous layer with toluene. Washed the total organic layer with water. Added 65 grams of silica gel to the organic layer. Stirred the reaction mixture for 20 minutes at 25-35° C. Filtered the silica gel and washed with toluene. Added 65 grams of silica gel to the filtrate. Stirred for 20 minutes at 25-35° C. Filtered the silica gel and washed with toluene. Distilled the solvent completely under reduced pressure at below 70° C. Added 325 ml of acetonitrile to the obtained crude. Added 32.5 ml of trifluoroacetic acid to the above reaction mixture at 0-10° C. Stirred the reaction mixture for 8 hours at 0-10° C. Raised the temperature to 30-35° C. Added aqueous sodium hydroxide solution (3.25 grams in 33 ml of water) to the reaction mixture. Stirred the reaction mixture for 1.5 hours at 25-30° C. Distilled the solvent completely under reduced pressure at below 50° C. Added 130 ml of water to the reaction mixture. Washed the reaction mixture with tertiary butyl acetate. Added 325 ml of acetonitrile to the above reaction mixture. Added 64 grams of sodium chloride to the above reaction mixture. Adjusted the pH of the reaction mixture to 4.9 with aqueous hydrochloric acid. Stirred the reaction mixture for 10 minutes. Separated the organic and aqueous layer. Cooled the organic layer to 0-10° C. Added 8 ml of tertiarybutyl amine to the organic layer at 0-10° C. Raised the reaction mixture temperature to 25-35° C. and stirred for 60 minutes. Distilled the solvent completely under reduced pressure at below 50° C. Added 65 ml of acetonitrile to the reaction mixture and distilled the solvent completely under reduced pressure. Added 195 ml of acetonitrile to the reaction mixture. Cooled the reaction mixture to 25-35° C. Stirred the reaction mixture for 1.5 hours at 25-35° C. Cooled the reaction mixture to 0-10° C. and stirred for 60 minutes at 0-10° C. Filtered the solid and washed the solid with acetonitrile. Added 195 ml of acetonitrile and 23 ml of isopropyl alcohol to the wet solid. Heated the reaction mixture to reflux at 70-75° C. Stirred the reaction mixture at reflux for 30 minutes. Cooled the reaction mixture to 25-30° C. in 1.5 hours. Stirred the reaction mixture for 30 minutes at 25-30° C. Filtered the solid and washed with acetonitrile. Dried the solid at 30-35° C. for 2 hours followed by 40-45° C. for another 4 hours to get the title compound.

Yield: 25 grams

Example-41

Preparation of Pitavastatin Calcium Compound of Formula-1C

Added a aqueous solution of sodium hydroxide (5.4 grams in 66 ml of water) to the solution of 75 grams of pitavastatin tertiarybutyl amine salt compound of Formula-5C in 370 ml of water at 20-30° C. Stirred the reaction mixture for 1.5 hours at 20-30° C. Extracted the reaction mixture twice with tertiary butyl acetate. Adjusted the pH of the reaction mixture to 9.2 by evaporating the aqueous reaction mixture with nitrogen under reduced pressure at below 40° C. Filtered the reaction mixture through micron filter and washed with water. The particle freed reaction mixture added to an aqueous solution of calcium acetate (13 grams in 75 ml of water) in 45 minutes at 25-30° C. Stirred the reaction mixture for 45 minutes at 25-30° C. Filtered the solid and washed with water at 25-30° C. Dried the solid at 25-35° C. for 6 hours followed by 40-45° C. for 5 hours to get the title compound.

Yield: 60 grams

Example-42

Preparation of Rosuvastatin Calcium Compound of Formula-1A

Added a aqueous solution of sodium hydroxide (9 grams in 110 ml of water) to the solution of 125 grams of rosuvastatin tertiarybutyl amine salt compound of formula-5A in 630 ml of water at 20-30° C. Stirred the reaction mixture for 1.5 hours at 20-30° C. Extracted the reaction mixture twice with tertiary butyl acetate. Adjusted the pH of the reaction mixture to 9.1 by evaporating the aqueous reaction mixture with nitrogen under reduced pressure at below 40° C. Filtered the reaction mixture through micron filter and washed with water. Distilled the filtrate to dryness under reduced pressure at below 30° C. to get the sodium salt of Rosuvastatin. Adding the aqueous solution of obtained sodium salt to an aqueous solution of calcium acetate (21.4 grams in 125 ml of water) in 45 minutes at 25-30° C. Stirred the reaction mixture for 45 minutes at 25-30° C. Filtered the solid and washed with water at 25-30° C. Dried the solid at 25-35° C. for 6 hours followed by 40-45° C. for 5 hours to get the title compound.

Yield: 101 grams; M.C: 3.2%

Particle Size: D (v, 0.1) is 4.78 µm; D(v, 0.5) is 42.32 µm; D(v, 0.9) is 175.32 µm.

Particle Size after micronization: D (v, 0.1) is 2.53 µm; D(v, 0.5) is 10.54 µm; D(v, 0.9) is 34.14 µm.

We claim:

1. A method for the preparation of a compound of Formula-1,

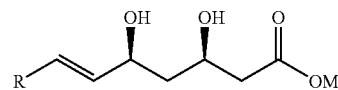

wherein R is

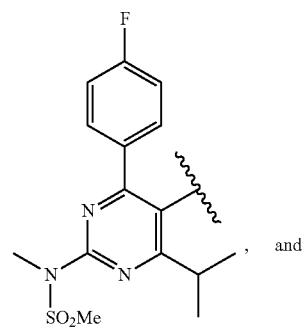

, and

M is $Ca^{+2}$, the method comprising:
a) reacting a compound represented by the following structural formula

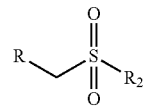

wherein R is defined as above and $R_2$ is

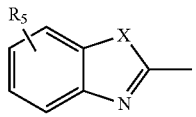

wherein:
$R_5$ is H, alkyl, alkoxy, haloalkyl, monohaloalkyloxy, or dihaloalkyloxy; and
X is N-alkyl;
with a compound of Formula-4

Formula-4

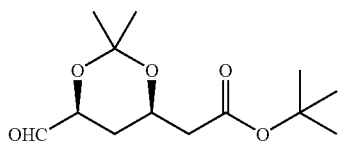

in the presence of an alkali or alkaline earth metal base in a polar aprotic solvent to give a condensed product, which is reacted in-situ with trifluoroacetic acid in a second solvent then hydrolyzed under basic conditions in aqueous acetonitrile then reacted with an organic amine base in a third solvent to give a compound which is purified in a fourth solvent and, optionally, dried to give a compound of Formula-5, Formula-5

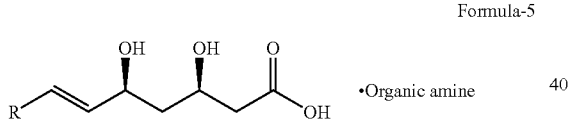

wherein R is defined as above and organic amine is selected from methyl amine, ethyl amine, tertiarybutyl amine, diisopropyl amine, dicyclohexyl amine, isobutyl amine, n-butylamine, (+/−) 2-butyl amine, phenyl ethyl amine, morpholine and pyrrolidine;

b) treating the compound Formula-5 with an alkali base to obtain a reaction mixture containing a compound of Formula-6:

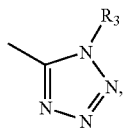

i

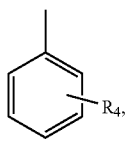

j

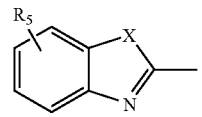

k wherein R is defined as above and M is $Na^+$, $K^+$ or $Li^+$, and adjusting the pH of the reaction mixture to 8.0 to 9.2 by washing the reaction mixture with tertiary butyl acetate or by directly distilling the reaction mixture;

c) optionally, isolating from the reaction mixture the compound of Formula-6; and d) adding the aqueous phase of the reaction mixture from step (b) or an aqueous solution of the isolated compound of Formula-6 from step (c) to a solution of calcium chloride or calcium acetate in a solvent to give the compound of Formula-1.

2. A method for the preparation of a compound of Formula-1,

Formula-1

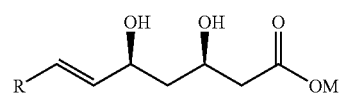

wherein R is

Formula-A

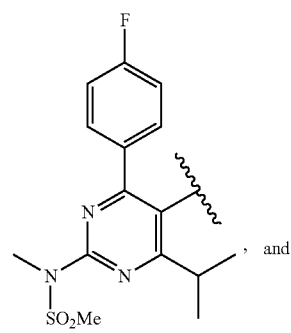

, and

M is $Ca^{+2}$,
the method comprising:
a) reacting a compound represented by the following structural formula

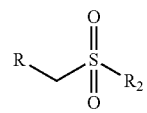

wherein R is defined as above and $R_2$ is

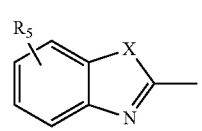

wherein:
R$_5$ is H, alkyl, alkoxy, haloalkyl, monohaloalkyloxy, or dihaloalkyloxy; and
X is N-alkyl;
with a compound of Formula-7

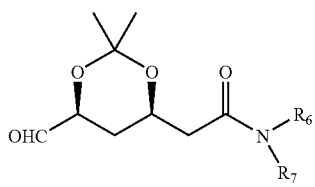

Formula-7 wherein R$_6$ and R$_7$ are C$_1$-C$_{10}$ straight- or branched-chain alkyl, cycloalkyl or cycloalkyl with one heteroatom,
in the presence of an alkali or alkaline earth metal base in a polar aprotic solvent to provide a compound of Formula-8,

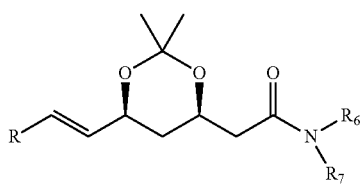

Formula-8 wherein R, R$_6$, and R$_7$ are defined as above,
which is reacted in-situ with acid in a solvent to give a compound of Formula-9,

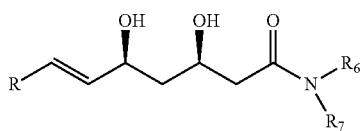

Formula-9 wherein R, R$_6$, and R$_7$ are defined as above,
which, upon treating with an alkali base forms a corresponding alkali salt then further treating with organic amine base, gives a compound of Formula-5, and, optionally, drying the compound of Formula-5,

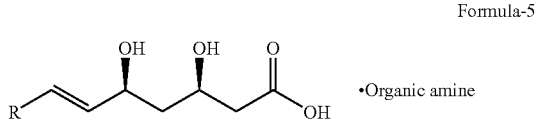

Formula-5 wherein R is defined as above and organic amine is selected from methyl amine, ethyl amine, tertiary-butyl amine, diisopropyl amine, dicyclohexyl amine, isobutyl amine, n-butylamine, (+/−) 2-butyl amine, phenyl ethyl amine, morpholine and pyrrolidine;
b) treating the compound of Formula-5 with an alkali base to obtain a reaction mixture containing a compound of Formula-6:

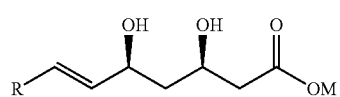

Formula-6 wherein R is defined as above and M is Na$^+$, K$^+$ or Li$^+$, and adjusting the pH of the reaction mixture to 8.0 to 9.2 by washing the reaction mixture with tertiary butyl acetate or directly distilling the reaction mixture;
c) optionally, isolating from the reaction mixture the compound of Formula-6; and
d) adding the aqueous phase of the reaction mixture from step (b) or an aqueous solution of the isolated compound of Formula-6 from step (c) to a solution of calcium chloride or calcium acetate in a solvent to give the compound of Formula-1.

3. A method for the preparation of a compound of Formula-1,

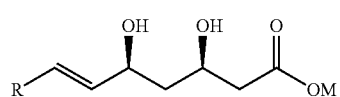

Formula-1 wherein R is

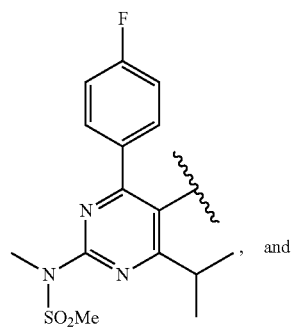

Formula-A

M is Ca$^{+2}$,
the method comprising:
a) reacting a compound represented by the following structural formula

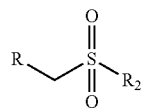

wherein R is defined as above and R$_2$ is

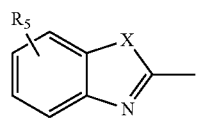

wherein:
R$_5$ is H, alkyl, alkoxy, haloalkyl, monohaloalkyloxy, or dihaloalkyloxy; and
X is N-alkyl;

with a compound of Formula-4

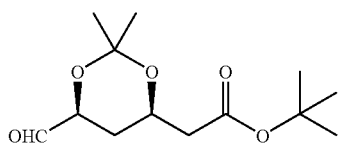

Formula-4 in the presence of an alkali or alkaline earth metal base in a polar aprotic solvent to provide a condensed compound, which is reacted in-situ with trifluoroacetic acid to give a lactone compound, which is further reacted with organic amine $HNR_8R_9$ to give a compound of Formula-10,

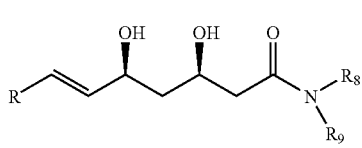

Formula-10 wherein R is defined as above and $R_8$ and $R_9$ are $C_1$-$C_{10}$ straight- or branched-chain alkyl, cycloalkyl or cycloalkyl with one heteroatom;

b) reacting the compound of Formula-10 with an alkali base followed by an organic amine base to give a compound of Formula-5, and, optionally, drying the compound of Formula-5,

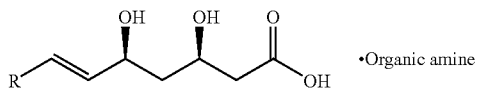

Formula-5 wherein R is defined as above and organic amine is selected from methyl amine, ethyl amine, tertiarybutyl amine, diisopropyl amine, dicyclohexyl amine, isobutyl amine, n-butylamine, (+/−) 2-butyl amine, phenyl ethyl amine, morpholine and pyrrolidine;

c) treating the compound of Formula-5 with an alkali base to obtain a reaction mixture containing a compound of Formula-6:

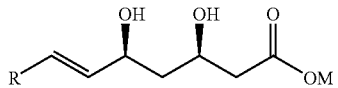

Formula-6 wherein R is defined as above and M is $Na^+$, $K^+$ or $Li^+$, and adjusting the pH of the reaction mixture to 8.0 to 9.2 by washing the reaction mixture with tertiary butyl acetate or directly distilling the reaction mixture;

d) optionally, isolating from the reaction mixture the compound of Formula-6; and e) adding the aqueous phase of the reaction mixture from step (c) or an aqueous solution of the isolated compound of Formula-6 from step (d) to a solution of calcium chloride or calcium acetate in a solvent to give the compound of Formula-1.

4. A method for the preparation of a compound of Formula-1,

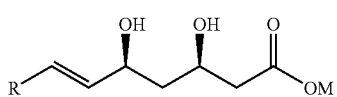

Formula-1 wherein R is

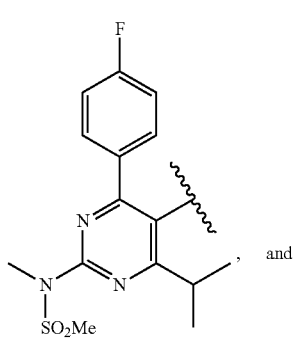

Formula-A

, and

M is $Ca^{+2}$, the method comprising:

a) reacting a compound represented by the following structural formula

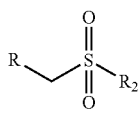

wherein R is defined as above and $R_2$ is

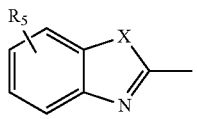

wherein:
  $R_5$ is H, alkyl, alkoxy, haloalkyl, monohaloalkyloxy, or dihaloalkyloxy; and
  X is N-alkyl;
with a compound of Formula-4

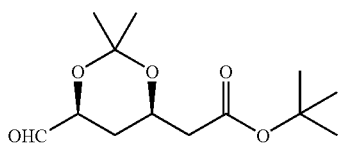

Formula-4 the presence of an alkali or alkaline earth metal base in a polar aprotic solvent to provide a compound of Formula-11, Formula-11

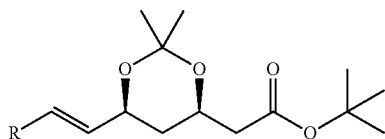

wherein R is defined as above,
which is reacted in-situ with acid in a solvent to give a compound of Formula-12, Formula-12

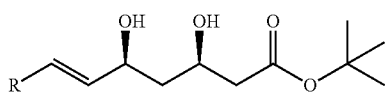

wherein R is defined as above,
which, upon treating with an alkali base then further treating with an organic amine base, gives a compound of Formula-5, and, optionally, drying the compound of Formula-5, Formula-5

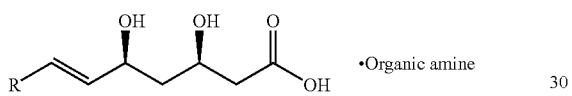

wherein R is defined as above and organic amine is selected from methyl amine, ethyl amine, tertiarybutyl amine, diisopropyl amine, dicyclohexyl amine, isobutyl amine, n-butylamine, (+/−) 2-butyl amine, phenyl ethyl amine, morpholine and pyrrolidine;
b) treating the compound of Formula-5 with an alkali base to obtain a reaction mixture containing a compound of Formula-6:

Formula-6

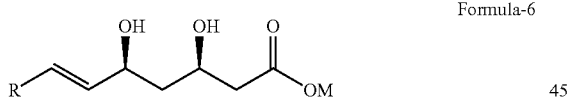

wherein R is defined as above and M is $Na^+$, $K^+$ or $Li^+$,
and adjusting the pH of the reaction mixture to 8.0 to 9.2 by washing the reaction mixture with tertiary butyl acetate or directly distilling the reaction mixture;
c) optionally, isolating from the reaction mixture the compound of Formula-6; and
d) adding the aqueous phase of the reaction mixture from step (b) or an aqueous solution of the isolated compound of Formula-6 from step (c) to a solution of calcium chloride or calcium acetate in a solvent to give the compound of Formula-1.

5. A process for the preparation of a compound of Formula-2,

Formula-2

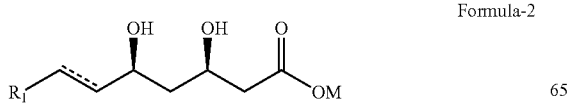

wherein:
$R_1$ is

Formula-a

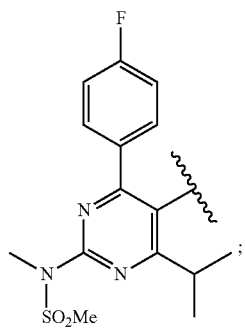

"⚡" denotes single or double bond; and
M is $Na^+$, $K^+$, $Mg^{+2}$, or $Ca^{+2}$,
the method comprising;
a) reacting a compound represented by the following structural formula:

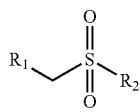

wherein $R_1$ is defined as above and $R_2$ is

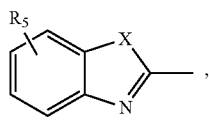

wherein:
$R_5$ is H, alkyl, alkoxy, haloalkyl, monohaloalkoxy, or dihaloalkoxy; and
X is N-alkyl;
with a compound of Formula-14

Formula-14

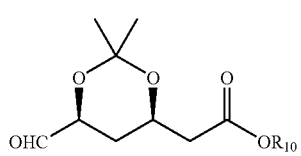

wherein $R_{10}$ is alkyl, cycloalkyl, arylalkyl, aryl or carbonylbenzyloxy,
in the presence of an alkali or alkaline earth metal base in a polar aprotic solvent to provide a compound of Formula-15, Formula-15

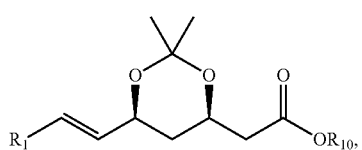

wherein $R_1$ and $R_{10}$ are defined as above;

b) subjecting the compound of Formula-15 to acidic conditions to form a diol, hydrolyzing the diol under basic conditions to form a hydrolyzed product, then treating the hydrolyzed product with an organic amine base to give a compound of Formula-16,

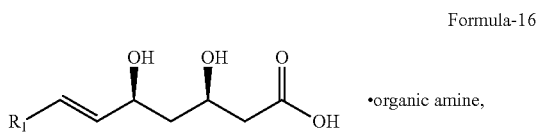

Formula-16

·organic amine, wherein $R_1$ is defined as above and the organic amine is selected from methyl amine, ethyl amine, tertiarybutyl amine, diisopropyl amine, dicyclohexyl amine, isobutyl amine, n-butylamine, (+/−) 2-butyl amine, phenyl ethyl amine, morpholine and pyrrolidine;

c) optionally, treating the compound of Formula-16 with an acid to give a compound of Formula-21,

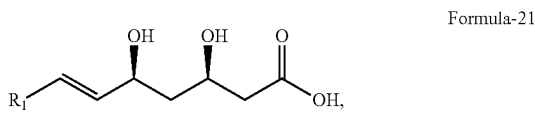

Formula-21 wherein $R_1$ is defined as above, and hydrogenating the compound of Formula-21 to provide a compound of Formula-22,

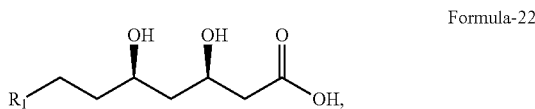

Formula-22 wherein $R_1$ is defined as above; and d) treating the compound of Formula-16 with an alkali base then an alkali or alkaline earth metal salt in a solvent or treating the compound of Formula-22 with an alkali or alkaline earth metal salt in a solvent to obtain the compound of Formula-2.

6. The method of claim 1, wherein:
in step a), the alkali or alkaline earth metal base is sodium hydroxide, potassium hydroxide, potassium carbonate, sodium carbonate, lithium carbonate, or cesium carbonate; the polar aprotic solvent is dimethylformamide, dimethylsulfoxide, dimethylacetamide, or toluene, or a mixture thereof; the solvent is acetonitrile; the third solvent is methanol, ethanol, isopropyl alcohol, or acetonitrile, or a mixture thereof; or the organic amine is tertiarybutyl amine or n-butylamine;
in step b), the alkali base is sodium hydroxide, potassium hydroxide, or lithium hydroxide; or
in step d), the solvent is water.

7. The method of claim 2, wherein:
in step a), the alkali or alkaline earth metal base is sodium hydroxide, potassium hydroxide, potassium carbonate, sodium carbonate, lithium carbonate, or cesium carbonate; the polar aprotic solvent is dimethylformamide, dimethylsulfoxide, or dimethylacetamide, or a mixture thereof; the acid is hydrochloric acid, acetic acid, or sulfuric acid; the alkali base is sodium hydroxide, potassium hydroxide or lithium hydroxide; or the organic amine is tertiarybutyl amine or n-butylamine;
in step b), the alkali base is sodium hydroxide, potassium hydroxide, or lithium hydroxide; or
in step d), the solvent is water.

8. The method of claim 3, wherein:
in step a), the alkali or alkaline earth metal base is sodium hydroxide, potassium hydroxide, potassium carbonate, sodium carbonate, lithium carbonate, or cesium carbonate; or the polar aprotic solvent is dimethylformamide, dimethylsulfoxide, or dimethylacetamide, or a mixture thereof;
in step b), the alkali base is sodium hydroxide, potassium hydroxide, or lithium hydroxide; or the organic amine is tertiarybutyl amine or n-butylamine;
in step c), the alkali base is sodium hydroxide, potassium hydroxide, or lithium hydroxide; or
in step e), the solvent is water.

9. The method of claim 4, wherein:
in step a), the alkali or alkaline earth metal base is sodium hydroxide, potassium hydroxide, potassium carbonate, sodium carbonate, lithium carbonate, or cesium carbonate; the polar aprotic solvent is dimethylformamide, dimethylsulfoxide, or dimethylacetamide, or a mixture thereof; the acid is hydrochloric acid, acetic acid, or sulfuric acid; the alkali base is sodium hydroxide, potassium hydroxide or lithium hydroxide; or the organic amine is tertiarybutyl amine or n-butylamine;
in step b), the alkali base is sodium hydroxide, potassium hydroxide or lithium hydroxide; or
in step d), the solvent is water.

10. The process of claim 5, wherein:
in step a), the alkali or alkaline earth metal base is sodium hydroxide, potassium hydroxide, potassium carbonate, sodium carbonate, lithium carbonate, or cesium carbonate; or the polar aprotic solvent is dimethylformamide, dimethylsulfoxide, or dimethylacetamide, or a mixture thereof;
in step b), the compound of Formula-15 is subjected to hydrochloric acid, acetic acid, or sulfuric acid; the diol is hydrolyzed with sodium hydroxide; or the organic amine is tertiarybutyl amine or n-butylamine; or
in step e), the alkali base is sodium hydroxide; the alkali or alkaline earth metal salt is calcium chloride, calcium acetate, or sodium hydroxide; or the solvent is water.

* * * * *

UNITED STATES PATENT AND TRADEMARK OFFICE
CERTIFICATE OF CORRECTION

PATENT NO. : 8,455,640 B2  Page 1 of 1
APPLICATION NO. : 12/226932
DATED : June 4, 2013
INVENTOR(S) : Manne Satyanarayana Reddy, Srinivasan Thirumalai Rajan and Maramreddy Sahadeva Reddy It is certified that error appears in the above-identified patent and that said Letters Patent is hereby corrected as shown below:

In column 89, Claim 1, lines 55-65 delete:

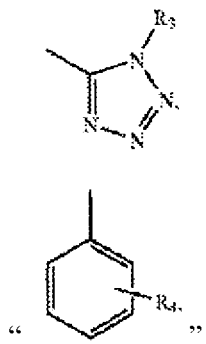

and insert:

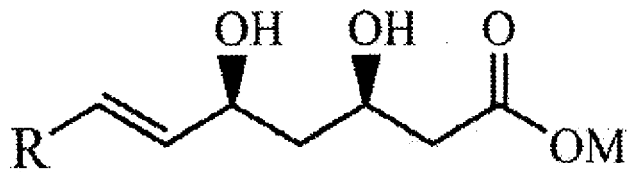

In column 90, Claim 1, lines 1-8 delete:

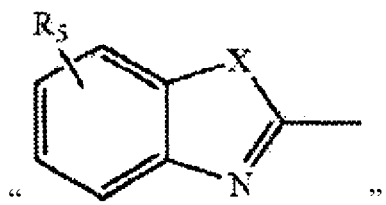

Signed and Sealed this
Seventeenth Day of September, 2013

Teresa Stanek Rea
*Deputy Director of the United States Patent and Trademark Office*